United States Patent [19]

Brunner et al.

[11] Patent Number: 6,103,667
[45] Date of Patent: Aug. 15, 2000

[54] PHENYLPYRAZOLE HERBICIDES

[75] Inventors: Hans-Georg Brunner, Lausen, Switzerland; Milan Karvas, Bratislava, Slovakia; Kurt Nebel, Hochwald, Switzerland; Georg Pissiotas, Lörrach, Germany

[73] Assignee: Novartis Corporation, Summit, N.J.

[21] Appl. No.: 08/765,161

[22] PCT Filed: Jun. 4, 1996

[86] PCT No.: PCT/EP96/02417

§ 371 Date: Dec. 12, 1996

§ 102(e) Date: Dec. 12, 1996

[87] PCT Pub. No.: WO97/00240

PCT Pub. Date: Jan. 3, 1997

[30] Foreign Application Priority Data

Jun. 15, 1995 [CH] Switzerland ............................. 1770/95
Dec. 4, 1995 [CH] Switzerland ............................. 3426/95

[51] Int. Cl.$^7$ ...................... C07D 231/18; C07D 405/12; A01N 43/56
[52] U.S. Cl. ................... 504/282; 548/366.1; 548/370.1; 548/370.4
[58] Field of Search ............................. 548/366.1, 370.1, 548/370.4; 504/282

[56] References Cited

U.S. PATENT DOCUMENTS 5,032,165  7/1991  Miura et al. ................................. 71/92

FOREIGN PATENT DOCUMENTS

| 1316175 | 4/1993 | Canada. |
|---|---|---|
| 75130761 | 10/1975 | Japan. |
| 2300173 | 9/1988 | Japan. |
| 3093774 | 4/1991 | Japan. |
| 3163063 | 7/1991 | Japan. |
| 1488285 | 10/1977 | United Kingdom. |
| 9202509 | 2/1992 | WIPO. |
| 9615115 | 5/1996 | WIPO. |

OTHER PUBLICATIONS

Derwent Abstract 91–159355/22 Apr. 1991 (Abstract of JP3093774).
Derwent Abstract 91–031992/05 Dec. 1990 (Abstract of JP2300173).
Derwent Abstract 91–249443 Aug. 1991 (Abstract of JP 3163063).
Chem. Abst. vol. 85(1), No. 56 20s (1976) of JP–A–75 130761.
Chem. Ber. 92, 2593 (1959).
Acta Chem. Scard. 16, 2395 (1962).
Chemical Substances, 9th Collective Index, vol. 76–85, 1972–1976, p. 3332ICS, RN: [59309–89–6], [59309–96–5] and [59309–89–6].

*Primary Examiner*—Mukund J. Shah
*Assistant Examiner*—Bruck Kifle
*Attorney, Agent, or Firm*—William A. Teoli, Jr.; John D. Peabody, III

[57] ABSTRACT

Compounds of formula I

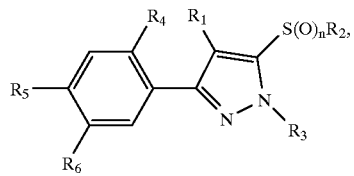

(I)

wherein the substituents $R_1$ and $R_6$ and n are as defined in claim 1, and the salts and stereoisomers of the compounds of formula I have good pre- and post-emergence selective herbicidal properties.

The preparation of those compounds and their use as herbicidal active ingredients are described.

19 Claims, No Drawings

PHENYLPYRAZOLE HERBICIDES

The present invention relates to novel, herbicidally active phenylpyrazole derivatives, to processes for their preparation, to compositions comprising those compounds, and to their use in controlling weeds, especially in crops of useful plants or in the inhibition of plant growth.

Pyrazole compounds having herbicidal action are known and are disclosed, for example, in EP-A-0 361 114, JP-A-03 093 774, JP-A-02 300 173 and JP-A-03 163 063.

Novel phenylpyrazole derivatives having herbicidal and growth-inhibiting properties have now been found.

The present invention therefor relates to compounds of formula I

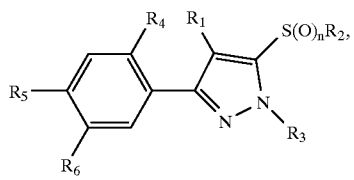
(I)

wherein $R_1$ is $C_1$–$C_4$alkyl;

$R_2$ is $C_1$–$C_4$alkyl, $C_1$–$C_4$haloalkyl, $C_3$- or $C_4$-alkenyl, $C_3$- or $C_4$-haloalkenyl or $C_3$- or $C_4$-alkynyl;

n is 0, 1 or 2;

$R_3$ is hydrogen, $C_1$–$C_4$alkyl, $C_1$–$C_4$haloalkyl, $C_3$- or $C_4$-alkenyl, $C_3$- or $C_4$-haloalkenyl, $C_3$- or $C_4$-alkynyl, —$CH_2$—COOH, —$CH_2$COO—$C_1$–$C_4$alkyl or —$CH_2$CN;

$R_4$ is hydrogen, fluorine, chlorine or bromine;

$R_5$ is hydrogen, methyl, trifluoromethyl, cyano, nitro, amino or $C_1$–$C_4$haloalkoxy;

$R_6$ is hydrogen, halogen, cyano, $NHR_{10}$, $NR_{10}R_{11}$ or $SO_2Cl$;

$R_{10}$ and $R_{11}$ are each independently of the other $C_1$–$C_8$alkyl, $C_3$–$C_8$alkenyl, $C_3$–$C_8$alkynyl, $C_3$–$C_6$cycloalkyl, $C_1$–$C_8$haloalkyl, $C_3$–$C_8$haloalkenyl, $C_1$–$C_4$alkylcarbonyl, $C_1$–$C_4$haloalkylcarbonyl, $C_1$–$C_4$alkylsulfonyl, $C_1$–$C_4$haloalkylsulfonyl, benzoyl, benzoyl mono- to tri-substituted by $C_1$–$C_4$alkyl, $C_1$–$C_4$haloalkyl or by halogen, benzyl, or benzyl mono- or tri-substituted by $C_1$–$C_4$alkyl, $C_1$–$C_4$haloalkyl or by halogen; or $R_6$ is $OR_{20}$;

$R_{20}$ is hydrogen, $C_1$–$C_8$alkyl, $C_3$–$C_8$alkenyl, $C_3$–$C_8$alkynyl, $C_1$–$C_8$haloalkyl,

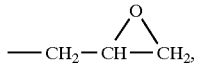

$C_3$–$C_8$haloalkenyl, $C_3$–$C_6$cycloalkyl,

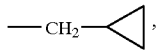, $C_1$–$C_4$alkoxy-$C_1$–$C_4$alkyl, $C_1$–$C_4$alkylamino-$C_1$–$C_4$alkyl, di-$C_1$–$C_4$alkylamino-$C_1$–$C_4$alkyl, $C_1$–$C_4$alkoxy-$C_1$–$C_4$alkoxy-$C_1$–$C_4$alkyl, $C_1$–$C_4$alkylthio-$C_1$–$C_4$alkyl, phenyl, benzyl, pyridyl, pyrimidinyl, pyrazinyl, pyridazinyl, those aromatic and heteroaromatic rings being unsubstituted or mono- or tri-substituted by $C_1$–$C_4$alkyl, $C_1$–$C_4$haloalkyl or by halogen; or $R_{20}$ is $C_1$–$C_8$alkyl-$COXR_{21}$ or $CH(C_6H_5)COXR_{21}$;

X is oxygen, sulfur or $NR_{22}$;

$R_{21}$ is hydrogen, $C_1$–$C_8$alkyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl, mono- to tri-substituted by $C_1$–$C_4$alkyl, $C_1$–$C_4$haloalkyl or by halogen, benzyl, or benzyl mono- or tri-substituted by $C_1$–$C_4$alkyl or by halogen; and $R_{22}$ is hydrogen, $C_1$–$C_8$alkyl or $C_3$–$C_8$alkenyl; or $R_6$ is $S(O)_m R_{30}$;

m is 0, 1 or 2;

$R_{30}$ is hydrogen, $C_1$–$C_8$alkyl, $C_3$–$C_8$alkenyl, $C_3$–$C_8$alkynyl, $C_1$–$C_8$haloalkyl, $C_3$–$C_8$haloalkenyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl mono- or tri-substituted by $C_1$–$C_4$alkyl, $C_1$–$C_4$haloalkyl or by halogen, benzyl, benzyl mono- to tri-substituted by $C_1$–$C_4$alkyl, $C_1$–$C_4$haloalkyl or by halogen, or $C_1$–$C_4$alkyl-$COVR_{31}$;

V is oxygen, sulfur or $NR_{32}$;

$R_{31}$ is hydrogen, $C_1$–$C_8$alkyl, $C_3$–$C_8$alkenyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl mono- to tri-substituted by $C_1$–$C_4$alkyl, $C_1$–$C_4$haloalkyl or by halogen, benzyl, or benzyl mono- to tri-substituted by $C_1$–$C_4$alkyl, $C_1$–$C_4$haloalkyl or by halogen; and $R_{32}$ is hydrogen, $C_1$–$C_8$alkyl or $C_3$–$C_8$; or $R_6$ is $COR_{40}$;

$R_{40}$ is hydrogen, chlorine, $C_1$–$C_8$alkyl, $C_3$–$C_8$alkenyl, $C_3$–$C_8$alkynyl, $C_1$–$C_8$haloalkyl, $C_3$–$C_8$haloalkenyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl mono- to tri-substituted by $C_1$–$C_4$alkyl, $C_1$–$C_4$haloalkyl or by halogen, benzyl, or benzyl mono- to tri-substituted by $C_1$–$C_4$alkyl, $C_1$–$C_4$haloalkyl or by halogen; or $R_6$ is $COYR_{50}$;

Y is oxygen, sulfur, $NR_{51}$ or $NOR_{54}$;

$R_{50}$ is hydrogen, $C_1$–$C_8$alkyl, $C_3$–$C_8$alkynyl, $C_1$–$C_8$haloalkyl,

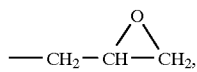

$C_3$–$C_8$haloalkenyl, $C_3$–$C_6$cycloalkyl,

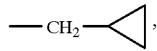, $C_1$–$C_4$alkoxy-$C_1$–$C_4$alkyl, $C_1$–$C_4$alkylthio-$C_1$–$C_4$alkyl, phenyl, phenyl mono- to tri-substituted by $C_1$–$C_4$alkyl, $C_1$–$C_4$haloalkyl or by halogen, benzyl, benzyl mono- to tri-substituted by $C_1$–$C_4$alkyl, $C_1$–$C_4$haloalkyl or by halogen, $C_1$–$C_4$alkyl-$COZR_{52}$, $C_3$–$C_6$cycloalkyl-$COZR_{52}$, $C_1$–$C_4$alkyl-CO—$C_1$–$C_4$alkyl or $C_1$–$C_4$cyanoalkyl;

Z is oxygen, sulfur, $NR_{53}$ or $NOR_{55}$;

$R_{52}$ is hydrogen, $C_1$–$C_8$alkyl, $C_3$–$C_8$alkenyl, $C_3$–$C_8$alkynyl, $C_1$–$C_8$haloalkyl,

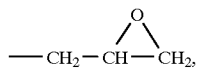

$C_3$–$C_8$haloalkenyl, $C_3$–$C_6$cycloalkyl,

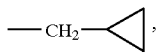

$C_1$–$C_4$alkoxy-$C_1$–$C_4$alkyl, $C_1$–$C_4$alkoxy-$C_1$–$C_4$alkoxy-$C_1$–$C_4$alkyl, $C_1$–$C_4$alkylthio-$C_1$–$C_4$alkyl, phenyl, phenyl mono- to tri-substituted by $C_1$–$C_4$alkyl, $C_1$–$C_4$haloalkyl or by halogen, benzyl, or benzyl mono- to tri-substituted by $C_1$–$C_4$alkyl, $C_1$–$C_4$haloalkyl or by halogen;

$R_{51}$ and $R_{53}$ are each independently of the other $C_1$–$C_8$alkyl, $C_3$–$C_8$alkenyl, $C_3$–$C_8$alkynyl, $C_1$–$C_8$haloalkyl, $C_1$–$C_4$alkylcarbonyl, $C_1$–$C_4$haloalkylcarbonyl, $C_1$–$C_4$alkylsulfonyl, $C_1$–$C_4$haloalkylsulfonyl, benzoyl, benzoyl mono- to tri-substituted by $C_1$–$C_4$alkyl, $C_1$–$C_4$haloalkyl or by halogen, benzyl, or benzyl mono- to tri-substituted by $C_1$–$C_4$alkyl, $C_1$–$C_4$haloalkyl or by halogen;

$R_{54}$ and $R_{55}$ are each independently of the other $C_1$–$C_4$alkyl; or $R_6$ is

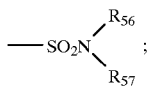

$R_{56}$ is hydrogen, $C_1$–$C_8$alkyl, $C_3$–$C_8$alkenyl or $C_3$–$C_8$alkynyl;

$R_{57}$ is hydrogen, $C_1$–$C_8$alkyl, $C_3$–$C_8$alkenyl or $C_3$–$C_8$alkynyl or $C_1$–$C_4$alkylcarbonyl; or $R_6$ is $C_1$–$C_8$-B, $C_1$–$C_8$haloalkyl-B, $C_2$–$C_8$alkenyl-B, $C_2$–$C_8$alkynyl-B, $C_2$–$C_8$haloalkenyl-B, $C_1$–$C_4$alkoxy-$C_1$–$C_4$alkyl-B or $C_1$–$C_4$alkylthio-$C_1$–$C_4$alkyl-B; and B is hydrogen, —$COZR_{52}$, cyano or $C_1$–$C_4$alkyl-C(O)—, and the salts and stereoisomers of the compound of formula I.

The present invention relates also to compounds of formula I wherein $R_1$ is $C_1$–$C_4$alkyl;

$R_2$ is $C_1$–$C_4$alkyl, $C_1$–$C_4$haloalkyl, $C_3$- or $C_4$-alkenyl, $C_3$- or $C_4$-haloalkenyl or $C_3$- or $C_4$-alkynyl;

n is 0, 1 or 2;

$R_3$ is hydrogen, $C_1$–$C_4$alkyl, $C_1$–$C_4$haloalkyl, $C_3$- or $C_4$-alkenyl, $C_3$- or $C_4$-haloalkenyl, $C_3$- or $C_4$-alkynyl, —$CH_2$—COOH, —$CH_2$COO—$C_1$–$C_4$alkyl or —$CH_2$CN;

$R_4$ is hydrogen, fluorine, chlorine or bromine;

$R_5$ is hydrogen, methyl, trifluoromethyl, cyano, nitro, amino or $C_1$–$C_4$haloalkoxy;

$R_6$ is hydrogen, halogen, $C_1$–$C_5$alkyl, $C_1$–$C_5$haloalkyl, $C_2$–$C_5$alkenyl, $C_2$–$C_5$haloalkenyl, $C_2$–$C_5$alkynyl, $C_2$–$C_5$haloalkynyl, cyano, $NHR_{10}$ or $NR_{10}R_{11}$;

$R_{10}$ and $R_{11}$ are each independently of the other $C_1$–$C_8$alkyl, $C_3$–$C_8$alkenyl, $C_3$–$C_8$alkynyl, $C_3$–$C_6$cycloalkyl, $C_1$–$C_8$haloalkyl, $C_3$–$C_8$haloalkenyl, $C_1$–$C_4$alkylcarbonyl, $C_1$–$C_4$haloalkylcarbonyl, $C_1$–$C_4$alkylsulfonyl, $C_1$–$C_4$haloalkylsulfonyl, benzoyl, benzoyl mono- to tri-substituted by $C_1$–$C_4$alkyl, $C_1$–$C_4$haloalkyl or by halogen, benzyl, or benzyl mono- or tri-substituted by $C_1$–$C_4$alkyl, $C_1$–$C_4$haloalkyl or by halogen; or $R_6$ is $OR_{20}$;

$R_{20}$ is hydrogen, $C_1$–$C_8$alkyl, $C_3$–$C_8$alkenyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, benzyl, pyridyl, pyrimidinyl, pyrazinyl, pyridazinyl, those aromatic and heteroaromatic rings being unsubstituted or mono- to tri-substituted by $C_1$–$C_4$alkyl, $C_1$–$C_4$haloalkyl or by halogen, or $C_1$–$C_8$alkyl-$COXR_{21}$;

X is oxygen, sulfur or $NR_{22}$;

$R_{21}$ is hydrogen, $C_1$–$C_8$alkyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl, mono- to tri-substituted by $C_1$–$C_4$alkyl, $C_1$–$C_4$haloalkyl or by halogen, benzyl, or benzyl mono- or tri-substituted by $C_1$–$C_4$alkyl or by halogen; and $R_{22}$ is hydrogen, $C_1$–$C_8$alkyl or $C_3$–$C_8$alkenyl; or $R_6$ is $S(O)_mR_{30}$;

m is 0, 1 or 2;

$R_{30}$ is hydrogen, $C_1$–$C_8$alkyl, $C_3$–$C_8$alkenyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl mono- to tri-substituted by $C_1$–$C_4$alkyl, $C_1$–$C_4$haloalkyl or by halogen, benzyl, benzyl mono- to tri-substituted by $C_1$–$C_4$alkyl, $C_1$–$C_4$haloalkyl or by halogen, or $C_1$–$C_4$alkyl-$COVR_{31}$;

V is oxygen, sulfur or $NR_{32}$;

$R_{31}$ is hydrogen, $C_1$–$C_8$alkyl, $C_3$–$C_8$alkenyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl mono- to tri-substituted by $C_1$–$C_4$alkyl, $C_1$–$C_4$haloalkyl or by halogen, benzyl, or benzyl mono- to tri-substituted by $C_1$–$C_4$alkyl, $C_1$–$C_4$haloalkyl or by halogen; and $R_{32}$ is hydrogen, $C_1$–$C_8$alkyl or $C_3$–$C_8$; or $R_6$ is $COR_{40}$;

$R_{40}$ is hydrogen, $C_1$–$C_8$alkyl, $C_3$–$C_8$alkenyl, $C_3$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl mono- to tri-substituted by $C_1$–$C_4$alkyl, $C_1$–$C_4$haloalkyl or by halogen, benzyl, or benzyl mono- to tri-substituted by $C_1$–$C_4$alkyl, $C_1$–$C_4$haloalkyl or by halogen; or $R_6$ is $COYR_{50}$;

Y is oxygen, sulfur, $NR_{51}$ or $NOR_{54}$;

$R_{50}$ is hydrogen, $C_1$–$C_8$alkyl, $C_3$–$C_8$alkenyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl mono- to tri-substituted by $C_1$–$C_4$alkyl, $C_1$–$C_4$haloalkyl or by halogen, benzyl, benzyl mono- to tri-substituted by $C_1$–$C_4$alkyl, $C_1$–$C_4$haloalkyl or by halogen, or $C_1$–$C_4$alkyl-$COZR_{52}$;

Z is oxygen, sulfur, $NR_{53}$ or $NOR_{55}$;

$R_{52}$ is hydrogen, $C_1$–$C_8$alkyl, $C_3$–$C_8$alkenyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl mono- to tri-substituted by $C_1$–$C_4$alkyl, $C_1$–$C_4$haloalkyl or by halogen, benzyl, or benzyl mono- to tri-substituted by $C_1$–$C_4$alkyl, $C_1$–$C_4$haloalkyl or by halogen;

$R_{51}$ and $R_{53}$ are each independently of the other $C_1$–$C_8$alkyl, $C_3$–$C_8$alkenyl, $C_3$–$C_8$alkynyl, $C_1$–$C_8$haloalkyl, $C_1$–$C_4$alkylcarbonyl, $C_1$–$C_4$haloalkylcarbonyl, $C_1$–$C_4$alkylsulfonyl, $C_1$–$C_4$haloalkylsulfonyl, benzoyl, benzoyl mono- to tri-substituted by $C_1$–$C_4$alkyl, $C_1$–$C_4$haloalkyl or by halogen, benzyl, or benzyl mono- to tri-substituted by $C_1$–$C_4$alkyl, $C_1$–$C_4$haloalkyl or by halogen;

$R_{54}$ and $R_{55}$ are each independently of the other $C_1$–$C_4$alkyl; or $R_6$ is $C_1$–$C_4$alkyl$COZR_{52}$, $C_1$–$C_4$haloalkyl$COZR_{52}$, $C_2$–$C_4$alkenyl$COZR_{52}$, $C_2$–$C_4$alkynyl$COZR_{52}$ or $C_2$–$C_4$haloalkenyl$COZR_{52}$, and the salts and stereoisomers of the compound of formula I.

The present invention relates also to compounds of formula I wherein $R_1$ is $C_1$–$C_4$alkyl;

$R_2$ is $C_1$–$C_4$alkyl, $C_1$–$C_4$haloalkyl, $C_3$- or $C_4$-alkenyl, $C_3$- or $C_4$-haloalkenyl or $C_3$- or $C_4$-alkynyl;

n is 0, 1 or 2;

$R_3$ is $C_1$–$C_4$alkyl, $C_1$–$C_4$haloalkyl, $C_3$- or $C_4$-alkenyl or $C_3$- or $C_4$-alkynyl;

$R_4$ is hydrogen, fluorine, chlorine or bromine;

$R_5$ is hydrogen, methyl, trifluoromethyl, cyano, nitro, amino or $C_1$–$C_4$haloalkoxy;

$R_6$ is hydrogen, halogen, cyano, $NHR_{10}$, $NR_{10}R_{11}$;

$R_{20}$ is hydrogen, $C_1$–$C_8$alkyl, $C_3$–$C_8$alkenyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, benzyl, pyridyl, pyrimidinyl, pyrazinyl, pyridazinyl, those aromatic and heteroaromatic rings being unsubstituted or mono- to tri-substituted by $C_1$–$C_4$alkyl, $C_1$–$C_4$haloalkyl or by halogen, or $C_1$–$C_8$alkyl-$COXR_{21}$;

X is oxygen, sulfur or $NR_{22}$;

$R_{21}$ is hydrogen, $C_1$–$C_8$alkyl, $C_3$–$C_8$alkynyl, $C_3$–$C_8$alkenyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl, mono- to tri-substituted by $C_1$–$C_4$alkyl, $C_1$–$C_4$haloalkyl or by halogen, benzyl, or benzyl mono- or tri-substituted by $C_1$–$C_4$alkyl or by halogen; and $R_{22}$ is hydrogen, $C_1$–$C_8$alkyl or $C_3$–$C_8$alkenyl; or $R_6$ is $S(O)_m R_{30}$;

m is 0, 1 or 2;

$R_{30}$ is hydrogen, $C_1$–$C_8$alkyl, $C_3$–$C_8$alkenyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl mono- to tri-substituted by $C_1$–$C_4$alkyl, $C_1$–$C_4$haloalkyl or by halogen, benzyl, benzyl mono- to tri-substituted by $C_1$–$C_4$alkyl, $C_1$–$C_4$haloalkyl or by halogen, or $C_1$–$C_4$alkyl-$COVR_{31}$;

V is oxygen, sulfur or $NR_{32}$;

$R_{31}$ is hydrogen, $C_1$–$C_8$alkyl, $C_3$–$C_8$alkenyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl mono- to tri-substituted by $C_1$–$C_4$alkyl, $C_1$–$C_4$haloalkyl or by halogen, benzyl, or benzyl mono- to tri-substituted by $C_1$–$C_4$alkyl, $C_1$–$C_4$haloalkyl or by halogen; and $R_{32}$ is hydrogen, $C_1$–$C_8$alkyl or $C_3$–$C_8$; or $R_6$ is $COR_{40}$;

$R_{40}$ is hydrogen, $C_1$–$C_8$alkyl, $C_3$–$C_8$alkenyl, $C_3$–$C_8$alkynyl, $C_3$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl mono- to tri-substituted by $C_1$–$C_4$alkyl, $C_1$–$C_4$haloalkyl or by halogen, benzyl, or benzyl mono- to tri-substituted by $C_1$–$C_4$alkyl, $C_1$–$C_4$haloalkyl or by halogen; or $R_6$ is $COYR_{50}$;

Y is oxygen, sulfur, $NR_{51}$ or $NOR_{54}$;

$R_{50}$ is hydrogen, $C_1$–$C_8$alkyl, $C_3$–$C_8$alkenyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl mono- to tri-substituted by $C_1$–$C_4$alkyl, $C_1$–$C_4$haloalkyl or by halogen, benzyl, benzyl mono- to tri-substituted by $C_1$–$C_4$alkyl, $C_1$–$C_4$haloalkyl or by halogen, or $C_1$–$C_4$alkyl-$COZR_{52}$;

Z is oxygen, sulfur, $NR_{53}$ or $NOR_{55}$;

$R_{52}$ is hydrogen, $C_1$–$C_8$alkyl, $C_3$–$C_8$alkenyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl mono- to tri-substituted by $C_1$–$C_4$alkyl, $C_1$–$C_4$haloalkyl or by halogen, benzyl, or benzyl mono- to tri-substituted by $C_1$–$C_4$alkyl, $C_1$–$C_4$haloalkyl or by halogen;

$R_{51}$ and $R_{53}$ are each independently of the other $C_1$–$C_8$alkyl, $C_3$–$C_8$alkenyl, $C_3$–$C_8$alkynyl, $C_1$–$C_8$haloalkyl, $C_1$–$C_4$alkylcarbonyl, $C_1$–$C_4$haloalkylcarbonyl, $C_1$–$C_4$alkylsulfonyl, $C_1$–$C_4$haloalkylsulfonyl, benzoyl, benzoyl mono- to tri-substituted by $C_1$–$C_4$alkyl, $C_1$–$C_4$haloalkyl or by halogen, benzyl, or benzyl mono- to tri-substituted by $C_1$–$C_4$alkyl, $C_1$–$C_4$haloalkyl or by halogen;

$R_{54}$ and $R_{55}$ are each independently of the other $C_1$–$C_4$alkyl; or $R_6$ is $C_1$–$C_4$alkyl$COZR_{52}$, $C_1$–$C_4$haloalkyl$COZR_{52}$, $C_2$–$C_4$alkenyl$COZR_{52}$, $C_2$–$C_4$alkynyl$COZR_{52}$ or $C_2$–$C_4$haloalkenyl$COZR_{52}$, and the salts and stereoisomers of the compound of formula I.

In the above definitions, unless otherwise indicated halogen is to be understood as being fluorine, chlorine, bromine and iodine, preferably fluorine, chlorine and bromine.

The alkyl, alkenyl and alkynyl groups may be straight-chained or branched, and this applies also to the alkyl, alkenyl and alkynyl moiety of alkylcarbonyl, haloalkyl, haloalkoxy, haloalkylcarbonyl, haloalkylphenyl, alkoxyalkyl, alkoxyalkoxyalkyl, alkylthio, alkenylthio, alkynylthio, alkylsulfonyl, alkylsulfonyl, haloalkylsulfonyl, alkenylsulfonyl, alkynylsulfonyl, alkylphenyl, alkylamino, dialkylamino, alkylaminocarbonyl-alkyl, alkylthio-alkoxycarbonyl, alkylthiocarbonyl-alkyl, alkenylthiocarbonyl, alkynylthiocarbonyl, haloalkoxycarbonyl-alkyl, alkylcarbonyl, alkenyloxycarbonyl, alkynyloxycarbonyl and alkoxycarbonyl-alkyl groups.

Examples of alkyl groups that may be mentioned are methyl, ethyl, n-propyl, isopropyl, n-butyl, isobutyl, sec-butyl, tert-butyl, and the various isomeric pentyl, hexyl, heptyl and octyl radicals, preferably alkyl groups having from 1 to 4 carbon atoms.

Examples of alkenyls that may be mentioned are vinyl, allyl, methallyl, 1-methylvinyl, but-2-en-1-yl, pentenyl, 2-hexenyl, 3-heptenyl and 4-octenyl, preferably alkenyl radicals having a chain length of from 3 to 5 carbon atoms.

Example of alkynyls that may be mentioned are ethynyl, propargyl, 1-methylpropargyl, 3-butynyl, but-2-yn-1-yl, 2-methylbutyn-2-yl, but-3-yn-2-yl, 1-pentynyl, pent-4-yn-1-yl and 2-hexynyl, preferably alkynyl radicals having a chain length of from 2 to 4 carbon atoms.

Suitable as haloalkyl are alkyl groups mono- or poly-substituted, especially mono- to tri-substituted, by halogen, with halogen being in particular iodine and especially fluorine, chlorine and bromine, for example fluoromethyl, difluoromethyl, trifluoromethyl, chloromethyl, dichloromethyl, trichloromethyl, 2,2,22-trifluoroethyl, 2-fluoroethyl, 2-chloroethyl and 2,2,2-trichloroethyl.

Suitable as haloalkenyl are alkenyl groups mono- or polysubstituted by halogen, with halogen being in particular bromine, iodine and especially fluorine and chlorine, for example 3-fluoropropenyl, 3-chloropropenyl, 3-bromopropenyl, 2,3,3-trifluoropropenyl, 2,3,3-trichloropropenyl, 4,4,4-trifluoro-but-2-en-1-yl and 4,4,4-trichloro-but-2-en-1-yl. Of the $C_2$–$C_5$alkenyl radicals mono-, di- or tri-substituted by halogen, preference is given to those having a chain length of 3 or 4 carbon atoms. The alkenyl groups may be substituted with halogen at saturated or unsaturated carbon atoms.

Haloalkenyl in the definition of $R_6$ as haloalkenylCOZR$_{52}$ is, for example, 1,2-dichloroethenyl or 1,2-dibromoethenyl.

Suitable as haloakynyl are, for example, alkynyl groups mono- or poly-substituted by halogen, with halogen being bromine, iodine and especially fluorine and chlorine, for example 3-fluoropropynyl, 3-chrloropropynyl, 3-bromopropynyl, 3,3,3-trifluoropropynyl and 4,4,4-trifluoro-but-2-yn-1-yl.

Carboxyalkyl is, for example, carboxymethyl, carboxyethyl, carboxyeth-1-yl and carboxypropyl.

Alkoxyalkyl is, for example, methoxymethyl, ethoxymethyl, propoxymethyl, methoxyethyl, ethoxyethyl, propryethyl, butoxyethyl, methoxypropyl, ethoxypropyl or propoxypropyl.

Alkoxy is, for example, methoxy, ethoxy, n-propoxy, isopropoxy, n-butoxy, isobutoxy, sec-butoxy and tert-butoxy.

Alkenyloxy is, for example, allyloxy, methallyloxy and but-2-en-1-yloxy.

Alkynyloxy is, for example, propargyloxy and 1-methylpropargyloxy.

Alkoxycarbonyl is, for example, methoxycarbonyl, ethoxycarbonyl, n-propoxycarbonyl, isopropoxycarbonyl and n-butoxycarbonyl, preferably methoxycarbonyl and ethoxycarbonyl.

Alkenyloxycarbonyl is, for example, allyloxycarbony, methallyloxycarbonyl, but-2-en-1-yl-oxycarbonyl, pentenyloxycarbonyl, 2-hexenyloxycarbonyl and 3-heptenyloxycarbonyl.

Alkynyloxycarbonyl is, for example, propargyloxycarbonyl, 3-butynyloxycarbonyl, but-2-yn-1-yl-oxycarbonyl and 2-methylbutyn-2-yl-oxycarbonyl.

Alkylamino is, for example, methylamino, ethylamino and the isomeric propylamino and butylamino.

Dialkylamino is, for example, dimethylamino and the isomeric dipropylamino and dibutylamino.

Alkenylamino is, for example, allylamino, methallylamino and but-2-en-1-yl-amino.

Alkynylamino is, for example, propargylamino and 1-methylpropargylamino.

Cycloalkyl radicals that come into consideration as substituents are, for example, cyclopropyl, cyclobutyl, cyclopentyl and cyclohexyl.

Alkoxyalkoxycarbonyl is, for example, methoxymethoxycarbonyl, ethoxymethoxycarbonyl, ethoxyethoxycarbonyl, propoxymethoxycarbonyl, propoxyethoxycarbonyl, propoxypropoxycarbonyl, butoxyethoxycarbonyl and butoxybutoxycarbonyl.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy.

Haloalkylamino is, for example, chloroethylamino, trifluoroethylamino and 3-chloropropylamino.

Di(haloalkyl)amino is, for example, di(chloroethyl)amino.

Alkylthioalkyl is, for example, methylthioethyl, ethylthioethyl, methylthiopropyl and ethylthiopropyl.

Alkenylthiocarbonyl is, for example allylthiocarbonyl, methallylthiocarbonyl, but-2-en-1-yl-thiocarbonyl.

Phenyl, benzyl or benzoyl as part of a substituent such as phenoxy, phenoxycarbonyl, phenoxycarbonylalkyl, benzoylamino or benzylamino is unsubstituted or substituted. The substituents may then be in the ortho- meta- or para-position. Substituents are, for example, $C_1$–$C_4$alkyl, halogen, $C_1$–$C_4$haloalkyl, cyano, nitro, hydroxy, $C_1$–$C_4$alkoxy, $C_1$–$C_4$haloalkoxy, amino, $C_1$–$C_4$alkylamino, di-$C_1$–$C_4$alkylamino, carboxyl, $C_1$–$C_4$alkoxycarbonyl, carbamoyl, $C_1$–$C_4$alkylaminocarbonyl or di-$C_1$–$C_4$alkylaminocarbonyl.

Corresponding meanings can be assigned also to the substituents in combined definitions, for example cycloalkyl-oxy, cycloalkyl-thio, cycloalkylcarbonyl, cycloalkyl-oxycarbonylalkyl, phenylalkyl, phenylalkenyl, alkoxycarbonylaklyl, alkenyloxycarbonylalkyl, alkynyloxycarbonyl-alkyl, haloalkoxycarbonyl-alkyl, alkylaminocarbonyl-alkyl, alkenylaminocarbonyl-alkyl, alkynylaminocarbonyl-alkyl, dialkylaminocarbonyl-alkyl, alkoxyalkylamino, alkoxyalkylaminocarbonyl-alkyl, dialkoxyalkylamino, alkoxyalkoxycarbonyl, alkoxyalkoxycarbonyl-alkyl, alkylaminocarbonyl, alkylthiocarbonyl, alkylthio-alkyl, , alkylthiocarbonyl-alkyl and haloalkoxycarbonyl-alkyl, and also for the combined definitions of the hydroxamic acid derivatives, such as, for example, for $R_6$=CON($R_{50}$)OR$_{54}$ or $R_6$=COY-$C_1$–$C_4$alkyl-CON($R_{52}$)OR$_{55}$.

Salts of the compounds of formula I with acidic hydrogen, especially the derivatives with carboxylic acid groups (for example carboxy-substituted alkyl and phenyl groups) are, for example, alkali metal salts, for example sodium and potassium salts; alkaline earth metal salts, for example calcium and magnesium salts; ammonium salts, that is to say unsubstituted ammonium salts and mono- or poly-substituted ammonium salts, for example triethylammonium and methylammonium salts; or salts with other organic bases.

Of the alkali metal and alkaline earth metal hydroxides as salt-forming agents, special mention should be made, for example, of the hydroxides of lithium, sodium, potassium, magnesium or calcium, but especially those of sodium or potassium.

Examples of amines suitable for ammonium salt formation are both ammonia and primary, secondary and tertiary $C_1$–$C_{18}$alkylamines, $C_1$–$C_4$hydroxyalkylamines and $C_2$–$C_4$alkoxyalkylamines, for example methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, thiomorpholine, N-methylmorpholine, N-methyl-thiomorpholine, piperidine, pyrrolidine, indoline, quinuclidine and azepine; primary arylamines, for example anilines, methoxyanilines, ethosyanilines, o,m,p-toluidines, phenylenediamines, benzidines, naphthylamines and o,m,p-chloroanilines; but especially triethylamine, isopropylamine and diisopropylamine.

Salts of the compounds of formula I with basic groups, especially the derivatives with amino groups, for example alkylamino, dialkylamino or alkenylamino, are, for example, salts with inorganic and organic acids, for example hydrochloric acids, such as hydrofluoric acid, hydrochloric acid, hydrobromic acid or hydroiodic acid, and also sulfuric acid, phosphoric acid, nitric acid and organic acids, such as acetic acid, trifluoroacetic acid, trichloroacetic acid, propionic acid, glycolic acid, thiocyanic acid, citric acid, benzoic acid, axalic acid, formic acid, benzenesulfonic acid, p-toluenesulfonic acid, methanesulfonic acid and salicylic acid.

The possible present of at least one asymmetric carbon or sulfur atom in the compounds of formula I, for example in the substituent $R_6=OR_{20}$ wherein $R_{20}$ is a branched alkyl, alkenyl, haloalkyl or alkoxyalkyl group, or $R_6=S(O)_m R_{30}$ wherein, for example, m=1 and/or $R_{30}$ is a branched alkyl, alkenyl, haloalkyl or alkoxyalkyl group, means that the compounds can occur both as optically active individual isomers and in the form of racemic mixtures. In the present invention, the compounds of formula I are to be understood as including both the pure optical antipodes and the racemates or diasteroisomers.

If an aliphatic C=C double bond is present, geometric isomerism may occur. The present invention relates also to those isomers.

Preference is given to compounds of formula I wherein $R_5$ is chlorine, bromine, methyl, trifluoromethyl or cyano.

Preference is given also to compounds of formula I wherein $R_6$ is hydrogen, halogen, $OR_{20}$, $S(O)_m R_{30}$ or $COYR_{50}$.

Compounds of formula I wherein n is 0 or 2 are also preferred.

Compounds of formula I wherein $R_1$ is methyl are also preferred.

Preference is also given to compounds of formula I wherein $R_2$ is methyl.

Also preferred are compounds of formula I wherein $R_3$ is methyl or ethyl.

Compounds of formula I wherein $R_3$ is methyl are especially preferred.

In a group of very especially preferred compounds of formula I, $R_4$ is fluorine.

In a further very especially preferred group of compounds of formula I, $R_4$ is hydrogen.

In another very especially preferred group of compounds of formula I, $R_4$ is chlorine.

In a further group of very especially preferred compounds of formula I, $R_4$ is chlorine; and $R_6$ is $OR_{20}$ wherein $R_{20}$ is as defined for formula I.

A group of very especially preferred compounds of formula I comprises compounds wherein $R_4$ is fluorine; and $R_6$ is $OR_{20}$ wherein $R_{20}$ is as defined for formula I.

Further groups of very especially preferred compounds of formula I comprise compounds wherein $R_4$ is chlorine; and $R_6$ is $S(O)_m R_{30}$ wherein $R_{30}$ and m are as defined for formula I.

In other groups of very especially preferred compounds of formula I, $R_4$ is fluorine; and $R_6$ is $S(O)_m R_{30}$ wherein $R_{30}$ and m are as defined for formula I.

A further group of very especially preferred compounds of formula I comprises compounds wherein $R_4$ is chlorine; and $R_6$ $COR_{40}$, $COYR_{50}$, $C_1$–$C_4$alkylCOZR$_{52}$, $C_1$–$C_4$haloalkylCOZR$_{52}$, $C_2$–$C_4$alkenylCOZR$_{52}$, $C_2$–$C_4$alkynylCOZR$_{52}$ or $C_2$–$C_4$haloalkenylCOZR$_{52}$ wherein $R_{40}$, $R_{50}$, $R_{52}$, Y and Z are as defined for formula I.

A further group of very especially preferred compounds of formula I comprises compounds wherein $R_4$ is fluorine; and $R_6$ $COR_{40}$, $COYR_{50}$, $C_1$–$C_4$alkylCOZR$_{52}$, $C_1$–$C_4$haloalkylCOZR$_{52}$, $C_2$–$C_4$alkenylCOZR$_{52}$, $C_2$–$C_4$alkynylCOZR$_{52}$ or $C_2$–$C_4$haloalkenylCOZR$_{52}$ wherein $R_{40}$, $R_{50}$, $R_{52}$, Y and Z are as defined for formula I.

In a further group of compounds of formula I that are likewise very especially preferred, $R_5$ is chlorine; and $R_6$ is —$COYR_{50}$.

Another group of likewise very especially preferred compounds of formula I comprises compounds wherein $R_5$ is chlorine; and $R_6$ is $C_1$–$C_4$alkyl-B or $C_1$–$C_4$haloalkyl-B.

The compounds of formula I

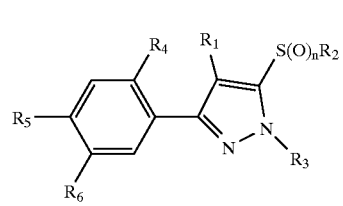

(I)

wherein $R_1$ to $R_6$ and n are as defined for formula I can be prepared by means of processes known per se, for example by cyclising a compound of formula III

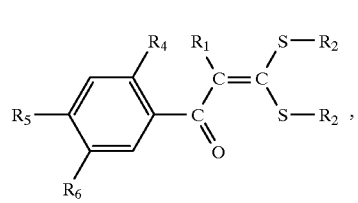

(III)

wherein $R_1$, $R_2$ and $R_4$ to $R_6$ are as defined, a) with hydrazine optionally in the presence of a suitable solvent to form a compound of formula IIa

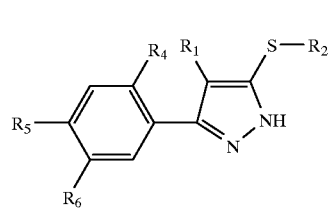

(IIa)

and then reacting that compound in the presence of a compound of formula Xa containing a corresponding $C_1$–$C_4$alkyl, $C_1$–$C_4$haloalkyl, $C_3$- or $C_4$-alkenyl or $C_3$- or $C_4$-alkynyl group $R_3$—$L_1$ (Xa), the radical $R_3$ in the compounds of formula Xa being as defined for formula I and $L_1$ being a leaving group, preferably chlorine, bromine, iodine, $CH_3SO_2O$— or

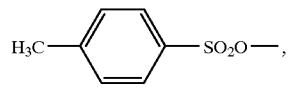

optionally in the presence of a suitable solvent to form a compound of formula I

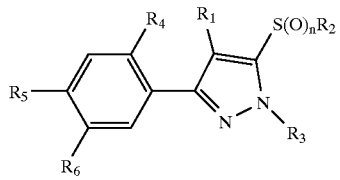
(I)

wherein n is 0, and then oxidising that compound; or b) with a compound of formula XI

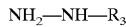
(XI), wherein $R_3$ is as defined, optionally in the presence of a suitable solvent, to form a compound of formula I

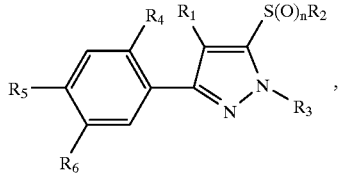
(I)

wherein $R_1$ to $R_6$ are as defined, and n is 0, and the oxidising that compound.

The process according to the invention for the preparation of a compound of formula II

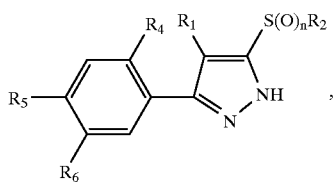
(II)

wherein $R_1$, $R_2$, $R_4$ to $R_6$ and n are as defined for formula I, is carried out analogously to known processes and comprises halogenating a compound of formula IV

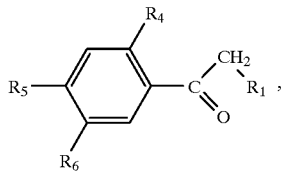
(IV)

optionally in the presence of a solvent and a base, for example acetic acid and sodium acetate, to form a compound of formula XII

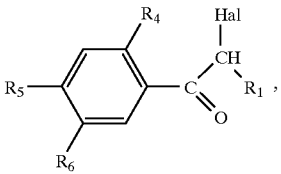
(XII)

$R_1$ and $R_4$ to $R_6$ in the compounds of formulae IV and XII being as defined and Hal being halogen, especially chlorine and bromine, and cyclising that compound of formula XII with a compound of formula XIII

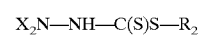
(XIII), wherein $R_2$ is as defined, optionally in the presence of a solvent, for example an alcohol, for example ethanol, and a base, for example an alcoholate, for example an ethanolate, to form a compound of formula XIV

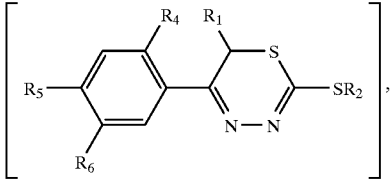
(XIV)

which is not isolated, and then subjecting that compound to a ring contraction (extrusion reaction) (n=0) thermally or by acid catalysis, for example with 2N hydrochloric acid, and then oxidising the product (n=1 or 2).

The formation of the pyrazole rings of the compounds of formula I wherein n is 0, 1 or 2 is illustrated in more detail in Reaction Schemes 1,2 and 10 below.

Reaction Scheme 1

Route a):

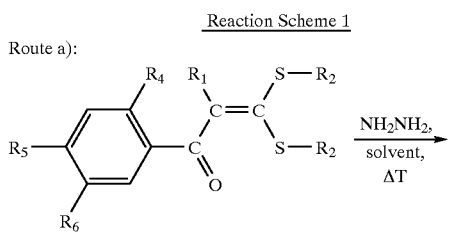

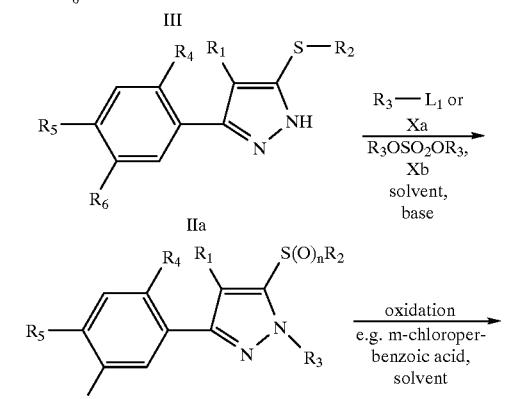

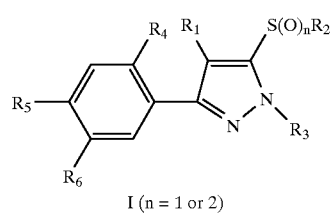

I (n = 1 or 2)

Route b):

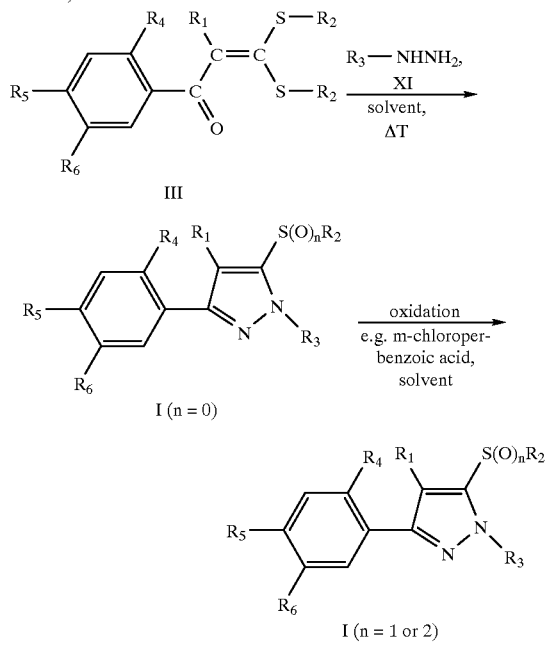

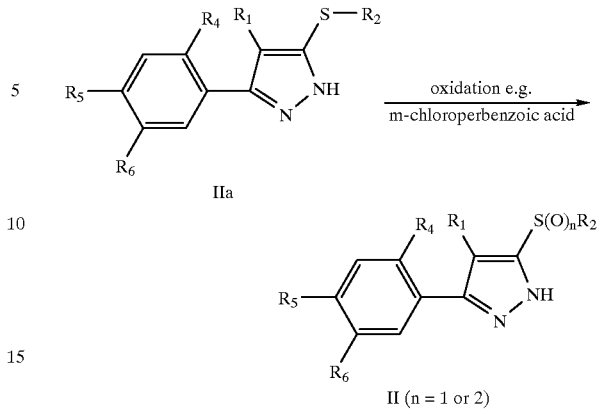

IIa

II (n = 1 or 2)

The formation of the pyrazole rings of formula IIa that are unsubstituted at the nitrogen atoms (Reaction Scheme 1, Route a)) is carried about by reaction of the compounds of formula III with hydrazine or hydrazine hydrate optionally in the presence of a suitable solvent at elevated temperature, preferably with hydrazine hydrate in alcoholic solution at elevated temperature.

For the formation of the pyrazole rings that are substituted at the nitrogen atom (Reaction Scheme 1, Route b)), the procedure is analogous to that indicated under Reaction Scheme 1, Route a), with a compound of formula XI, for example N-alkylhydrazine, preferably N-methylhydrazine, being used as reagent.

The formation of the pyrazole rings of formulae II and IIa that are unsubstituted at the nitrogen atoms (Reaction Scheme 2) can be carried out, for example, also by halogenation of the compounds of formula IV preferably with chlorine or bromine optionally in the presence of a suitable solvent and a base, for example acetic acid and sodium acetate, subsequent cyclisation with a compound of formula XIII optionally in a solvent, for example an alcohol, preferably ethanol, and in the presence of a base, for example an alcoholate preferably an ethanolate, and ring contraction (extrusion reaction) analogously to known procedures, as described, for example, in Chem Ber. 92, 2593 (1959) or Acta Chem. Scand. 16, 2395 (1962). That method, described in Reaction Scheme 2, is suitable for the preparation of derivatives of formulae IIa and II that are substituted by halogen, especially by fluorine and chlorine, at the phenyl ring.

In certain cases it is advantageous to prepare the N-alkyl-substituted pyrazole derivatives, especially the N-methyl-substituted pyrazole derivatives, via N-alkylation of the corresponding unsubstituted pyrazoles of formula II (or IIa). Reaction Scheme 3 illustrates this.

Reaction Scheme 2

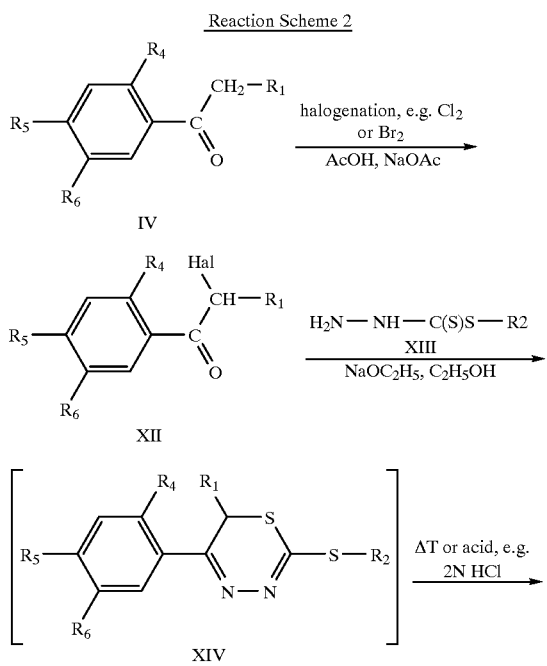

Reaction Scheme 3

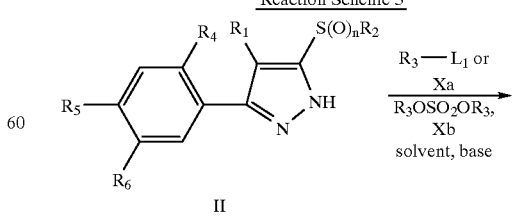

-continued

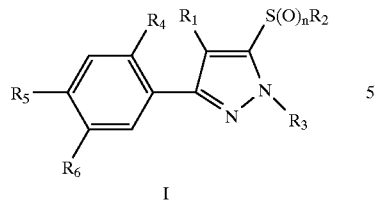

I

In this Reaction Schemes 1, Route b), and 3, the radical $R_3$ in the hydrazine derivative of formula XI and in the alkylating agents of formulae Xa and Xb is as defined for formula I, and $L_1$ is a leaving group, for example chlorine, bromine, iodine $CH_3SO_2O$— or

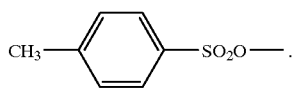

The N-alkylation of the pyrazole rings in the compounds of formulae II and IIa in Reaction Schemes 1 and 3 is carried out at room temperature or at slightly elevated temperatures in the presence of a solvent, for example acetone, methyl ethyl ketone, N,N-dimethylformamide, N-methylpyrrolidone or dimethyl sulfoxide, a base, for example potassium carbonate, sodium carbonate, sodium hydroxide or potassium hydroxide, and an alkylating agent of formula Xa, Xb, preferably methyl iodide or dimethyl sulfate.

The selection of the suitable preparation method and the corresponding reaction conditions is made in accordance with the properties (reactivites of the substituents in the intermediates in question.

The subsequent oxidation of the compounds of formula I wherein n is 0 (Reaction Schemes 1 and 2) is carried out, for example, with peracids, for example m-chloroperbenzoic acid, or hydrogen peroxide in the presence of a suitable solvent, for example dichloromethane chloroform or carbon tetrachloride, at temperatures of from −40° C. to the reflux temperature of the solvent in question, preferably from 0° C. to 35° C. The degree of oxidation at the sulfur atom can be controlled by the amount of oxidising agent: in the case of an equimolar amount of oxidising agent, compounds of formula I wherein n is 1 are obtained and is the case of an excess (at least 2 mol) of oxidising agent, compounds of formula I wherein n is 2 are obtained.

The starting compound of formula III in Reaction Scheme 1 can be prepared analogously to known procedures, for example in accordance with the method given in Reaction Scheme 4 below:

Reaction Scheme 4

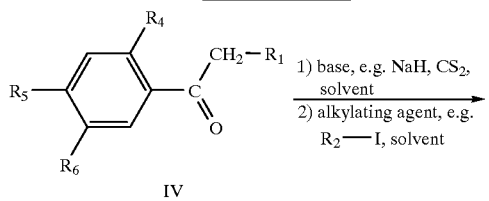

IV

-continued

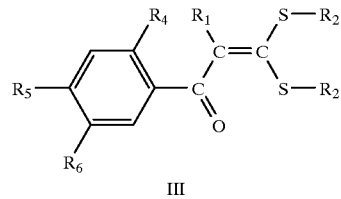

III

The reaction in Reaction Scheme 4 is carried out, for example, analogously to WO 92/02509, according to which the phenylcarbonyl derivative of formula IV is allowed to react in the presence of a base, for example sodium hydride or potassium tertubtanolate, and an oprotic solvent, for example tetrahydrofuran, with carbon disulfide at temperatures of from 0° C. to 80° C., and immediately afterwards an alkylating agent, for example $R_2$-Hal or $R_2OSO_2OR_2$ wherein $R_2$ is as defined for formula I and Hal is halogen, especially chlorine, bromine or iodine, is added at temperatures of from 0° C. to the reflux temperature of the solvent used.

The compounds of formula XIII in Reaction Scheme 2 can be prepared in accordance with known methods (for example Chem. ber. 92, 2593 (1959) or Acta Chem. Scand. 16, 2395 (1962)), for example by reaction of hydrazine or hydrazine hydrate with carbon disulfide and subsequent alkylation with the reagent $R_2$-Hal or $R_2$ $OSO_2OR_2$ wherein $R_2$ is as defined for formula I and Hal is halogen, especially chlorine or bromine, in the presence of a base. Suitable solvents are, for example, alcohols, for example ethanol, and suitable bases are, for example, alcoholates, for example sodium methanolate or sodium ethanolate, or potassium or sodium hydroxide.

The starting compound of formula IV in Reaction Scheme 4 can be prepared analogously to known procedures, for example in accordance with Methods a), b), c) and d) given in Reaction Scheme 5 below.

Reaction Scheme 5

Method a):

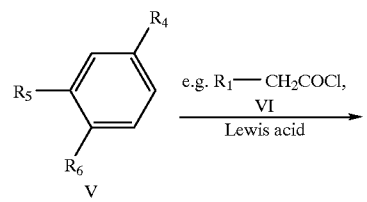

V

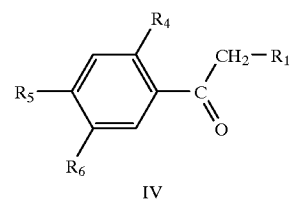

IV

Method b):

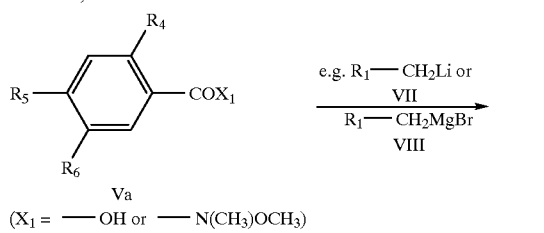

Method c):

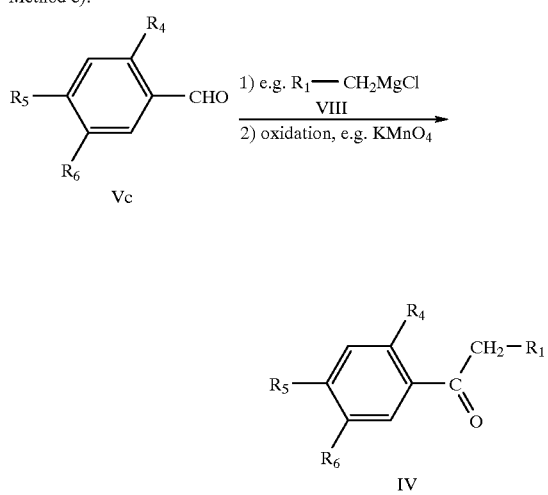

Method d):

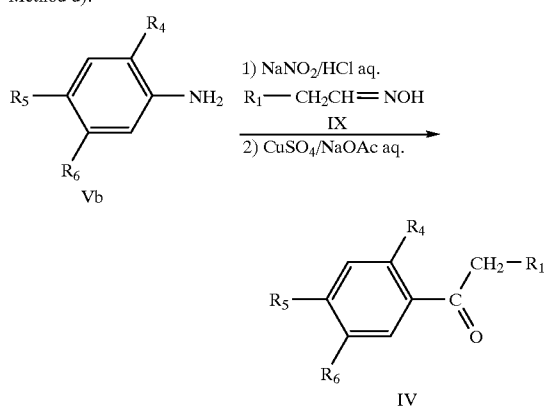

In Reaction Scheme 5, the radicals $R_1$, $R_4$, $R_5$ and $R_6$ are as defined for formula I, it being necessary to note that not all substituent definitions are compatible with all the procedures indicated. The selection of the suitable preparation method is made in accordance with the properties (reactivites) of the substituents in the intermediates in question.

The reaction according to Method a) in Reaction Scheme 5 is carried out analogously to 'Vogel's Textbook of Practical Organic Chemistry', Longman 1989, page 1006 ff. In that reaction the aromatic compound of formula V is allowed to react in the presence of a carboxylic acid derivative, for example a carboxylic acid chloride of formula VI and an acid, for example a Lewis acid such as aluminium chloride, with or without a solvent at temperatures of from 0° C. to 150° C.

The reaction according to Method b) in Reaction Scheme 5 is carried out, for example, starting from the carboxylic acid derivatives of formula Va wherein $X_1$ is —OH or —N(CH$_3$)OCH$_3$ with an alkylithium compound of formula VII or a grignard compound (alkylmagnesium chloride or bromide) of formula VIII in an inert solvent, preferably diethyl ether at temperatures of from –100° C. to 50° C., analogously to Organic Reactions 18, 1 (1970), Organic Synthesis 49, 81 (1969) and 'Comprehensive Organic Transformations', Editor R. C. Larock, VCH 1989, page 685.

The reaction according to Method c) in Reaction Scheme 5 is carried out analogously to 'Advanced Organic Chemistry', Editor J. March, McGraw-Hill Book Company, New York, 1985, pages 816 ff. and 1057 ff., starting from an aldehyde of formula Vc by means of a Grignard reagent of formula VIII, for example alkylmagnesium chloride or bromide, or by means of alkyllithium in an inert solvent, preferably diethyl ether, at temperatures of from –80° C. to 25° C. and subsequent oxidation of the alcohol to the ketone. Suitable oxidising agents are, for example, potassium permanganate, pyridinium dichromate and sodium dichromate.

The reaction according to Method d) in Reaction Scheme 5 is carried out analogously to J. Chem. Soc. 1954, 1297. The amines of formula Vb are accordingly first diazotised to form the corresponding diazonium salts and allowed to react with an aldehydeoxime of formula IX. Subsequent hydrolysis, for example with aqueous sodium acetate and copper sulfate, yields the corresponding methyl ketone of formula IV.

The starting compounds of formulae V, Va, Vb, Vc, VI, VII, VIII, IX and XI in Reaction Schemes 1, Route b), and 5 are known or can be prepared in accordance with known procedures.

The phenylpyrazole derivatives of formula II are novel and have been developed especially for the synthesis of the compounds of formula I. They are therefore also a subject of the present invention.

A large number of known standard procedures is available for the preparation of the phenylpyrazoles of formula I substituted in the 5-position of the phenyl ring ($R_6$), the selection of the suitable preparation processes being made in accordance with the properties (reactivites) of the substituents in the intermediates in question. Some examples are given in Reaction Schemes 6 to 9.

The preparation of the phenylpyrazole derivatives of formula I that are O-substituted in the 5-position of the phenyl rings, wherein $R_6$=$OR_{20}$, starting from the methoxy- or benzyloxy-substituted derivatives of formula $I_1$ or $I_2$, respectively, is illustrated in Reaction Scheme 6.

Reaction Scheme 6

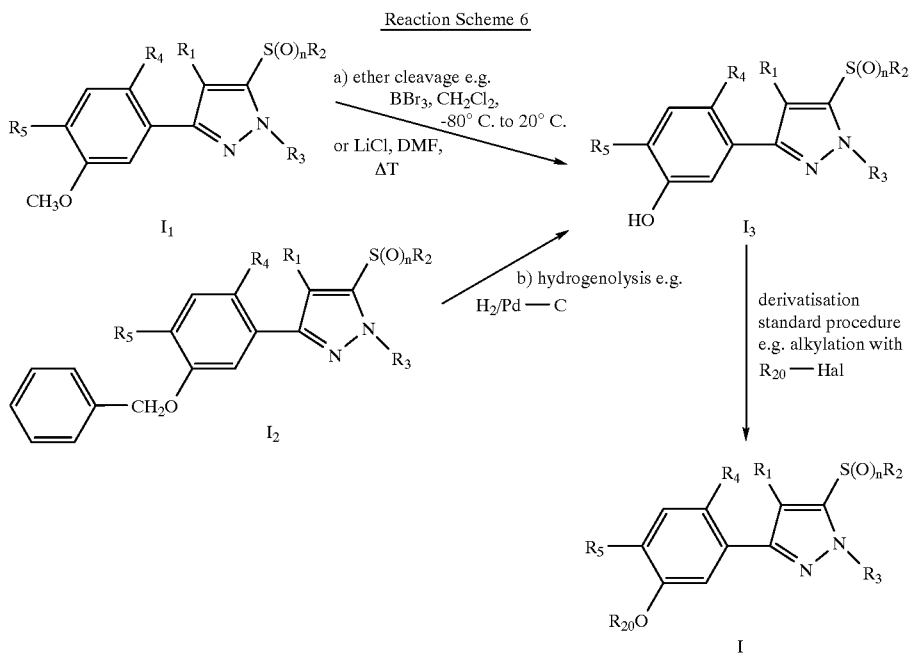

The phenolpyrazole derivatives of formula $I_3$ in Reaction Scheme 6 can be obtained, for example, a) from the compounds of formula $I_1$ via ether cleavage by means of lithium chloride in N,N-dimethylformamide (DMF) at elevated temperature, as described, for example, in Synthesis 1989, 287, or by means of boron tribromide in dichloromethane at temperatures of from −80° C., to 20° C., as described, for example, in Org. Synth., Collect. Vol. V, 412, 1973; or b) from the compounds of formula $I_2$ via hydrogenolysis by means of hydrogen in the presence of a catalyst, for example palladium on carbon, as described, for example, in J. Am. Chem. Soc. 93, 746 (1971).

The derivatisation of the phenolpyrazoles of formula $I_3$ in Reaction Scheme 6 to form the compounds of formula I can be carried out in accordance with standard procedures, for example via alkylation with $R_{20}$-Hal wherein $R_{20}$ is as defined for formula I and Hal is halogen, especially chlorine, bromine or iodine.

The preparation of the phenylpyrazole derivatives of formula I that are S-substituted in the 5-position of the phenyl ring, wherein $R_6=S(O_m R_{30}$, starting from the derivatives of formula $I_4$ that are unsubstituted in the 5-position, is illustrated in Reaction Scheme 7.

Reaction Scheme 7

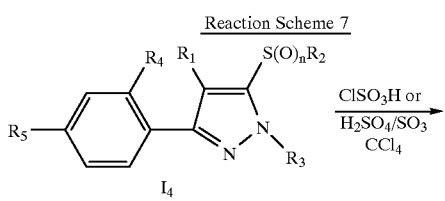

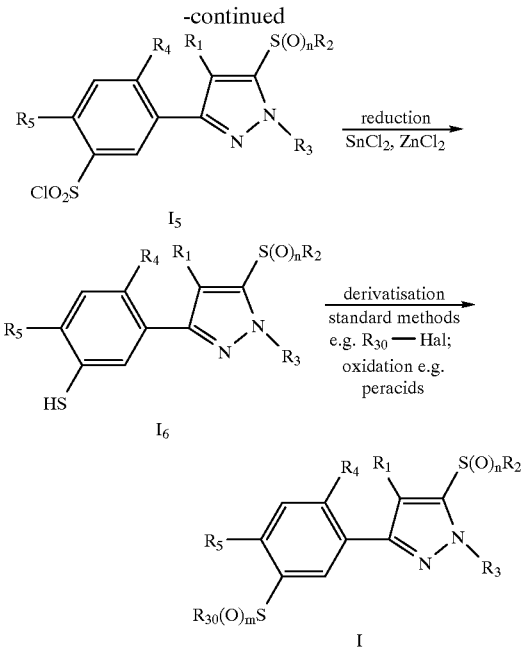

The preparation of the thiophenolpyrazoles of formula $I_6$ in Reaction Scheme 7 can be carried out analogously to known procedures, as described, for example, in J. Org. Chem. 54, 6096 (1989), EP-A-0 259 265 or in "Sulfonation and Related Reactions", Editor Gilbert, Interscience Publishers, New York 1965. The phenylpyrazole of formula $I_4$ is then chlorosulfonylated with chlorosulfonic acid or sulfur trioxide in sulfuric acid to form the compound of formula $I_5$ and then reduced with tin chloride or zinc chloride to the thiophenol derivative of formula $I_6$. The derivatisation of the thiophenolpyrazoles of formula $I_6$ to form the compounds of formula I in Reaction Scheme 7 can be carried out in accordance with standard procedures, for example via alkylation with $R_{30}$-Hal wherein $R_{30}$ is as defined for formula I and Hal is halogen, especially chlorine, bromine or iodine (m=0). The subsequent oxidation to the sulfine or sulfone derivatives of formula I (m=1 or 2, respectively) can likewise be carried out in accordance with standard procedures, for example with peracids, for example m-chloroperbenzoic acid.

The preparation of the phenylpyrazole derivatives of formula I that are carboxy-substituted in the 5-position of the phenyl ring, wherein $R_6$ is halogen, cyano, nitro, amino, $NHR_{10}$, $NR_{10}R_{11}$, $COR_{40}$ or $COYR_{50}$, starting from the derivatives of formula $I_4$ or $I_{11}$ that are unsubstituted in the 5-position or triflate-substituted in the 5-position, respectively, is illustrated in Reaction Scheme 8.

procedures, for example alkylation or acylation, or converted into the halogen compound of formula $I_9$ by means of diazotisation and Sandmeyer reaction. The benzoic acid ester of formula $I_{10}$ in Reaction Scheme 8 can be obtained, for example, analogously to J. Org. Chem. 39, 3318 (1974) or ibid. 40, 532 (1975) from the compound of formula $I_9$ by means of carbon monoxide and a catalyst, for example palladium chloride-triphenylphosphine ($PdCl_2(TPP)_2$) in the presence of a solvent, for example ethanol, optionally under pressure at elevated temperature. A further possible method of preparing the intermediate of formula $I_{10}$ is carried out analogously to Tetrahedron Letters 25, 2271 (1984) and ibid, 27, 3931 (1986). According to that method, the compound of formula $I_{11}$ is carbonylated in the presence of a catalyst, for

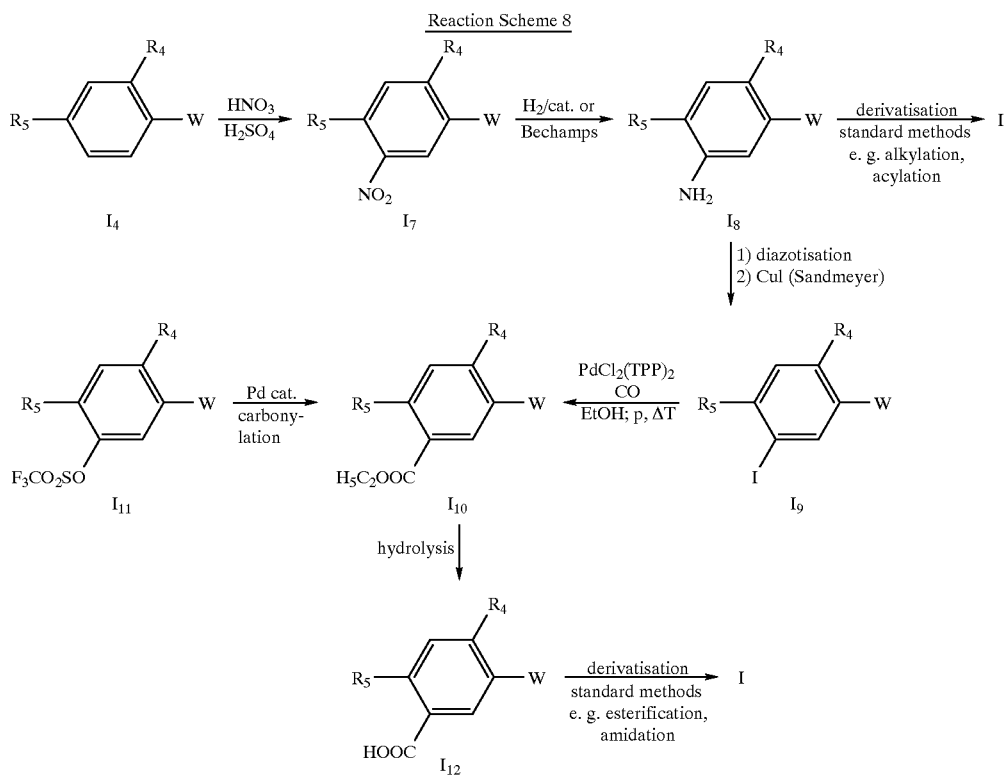

Reaction Scheme 8

In Reaction Scheme 8, W is the radical

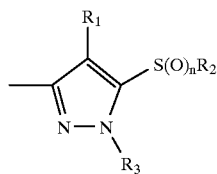

wherein $R_1$ to $R_3$ and n are as defined for formula I. In accordance with Reaction Scheme 8, the phenylpyrazole of formula $I_4$ can be converted into an aniline derivative of formula $I_8$ in accordance with standard procedures, for example nitration in a nitric acid and sulfuric acid mixture and subsequent reduction of the resulting nitro compound of formula $I_7$ with hydrogen in the presence of a catalyst or according to Bechamps. The aniline derivative of formula $I_8$ can then be either derivatised directly to form the corresponding compounds of formula I according to standard example palladium. The subsequent hydrolysis of the benzoic acid ester of formula $I_{10}$ yields the benzoic acid derivative of formula $I_{12}$, which can be converted into the corresponding compounds of formula I in accordance with standard procedures, for example esterification or amidation.

The preparation of the phenylpyrazole derivatives of formula I that are substituted in the 5-position of the phenyl ring, wherein $R_6$ is $C_1$–$C_4$alkylCOZR$_{52}$, $C_1$–$C_4$haloalkylCOZR$_{52}$, $C_2$–$C_4$alkenylCOZR$_{52}$, $C_2$–$C_4$alkynylCOZR$_{52}$ or $C_2$–$C_4$haloalkenylCOZR$_{52}$, starting from the derivatives of formula $I_9$ that are substituted in the 5-position of the phenyl ring by halogen, especially by chlorine, bromine or iodine, via Heck reaction (Route a)), or starting from the derivatives of formula $I_8$ that are substituted in the 5-position of the phenyl ring by amino via diazotisation and subsequent Meerwein reaction, is illustrated in Raction Scheme 9.

Reaction Scheme 9

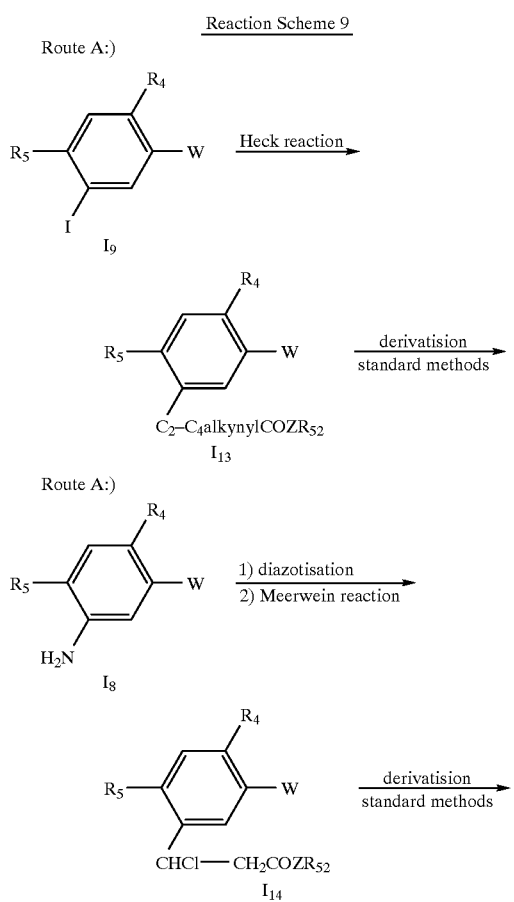

In Reaction Scheme 9, W is the radical

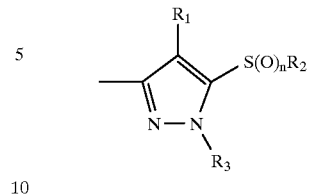

wherein $R_1$ to $R_3$ and n are as defined for formula I. In accordance with Reaction Scheme 9, Route a), the alkynyl ester derivatives of formula $I_{13}$ can be prepared, for example, via Heck reaction analogously to R. F. Heck in W. G. Dauben (Edit.), Organic Reactions 27, 345 (1982). It is possible to obtain therefrom by means of standard procedures, for example by means of partial or complete hydrogenation, the corresponding alkenyl- or alky-$COZR_{52}$ derivatives, respectively, or via halogenation the corresponding haloalkenyl- or haloalkyl-$COZR_{52}$ derivatives of formula I.

In accordance with Reaction Scheme 9, Route b), the haloalkyl$COZR_{52}$ derivatives of formula $I_{14}$ can be produced from the aniline derivatives of formula $I_8$ analogously to Organic Reactions 11, 189–260 (1960) via diazotisation and Meerwein reaction. Known standard procedures, for example hydrogenolysis or halogen removal, yield therefrom the corresponding alkyl- or alkenyl-$COZR_{52}$ derivatives of formula I.

Reaction scheme 10

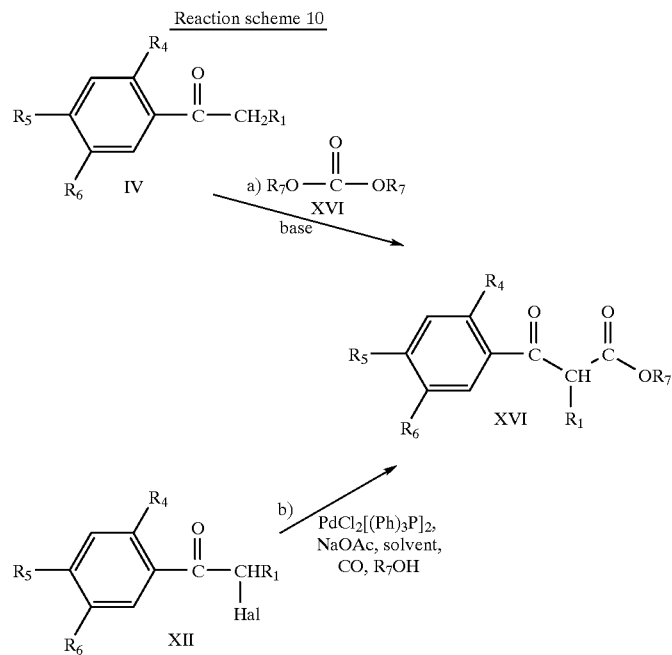

-continued

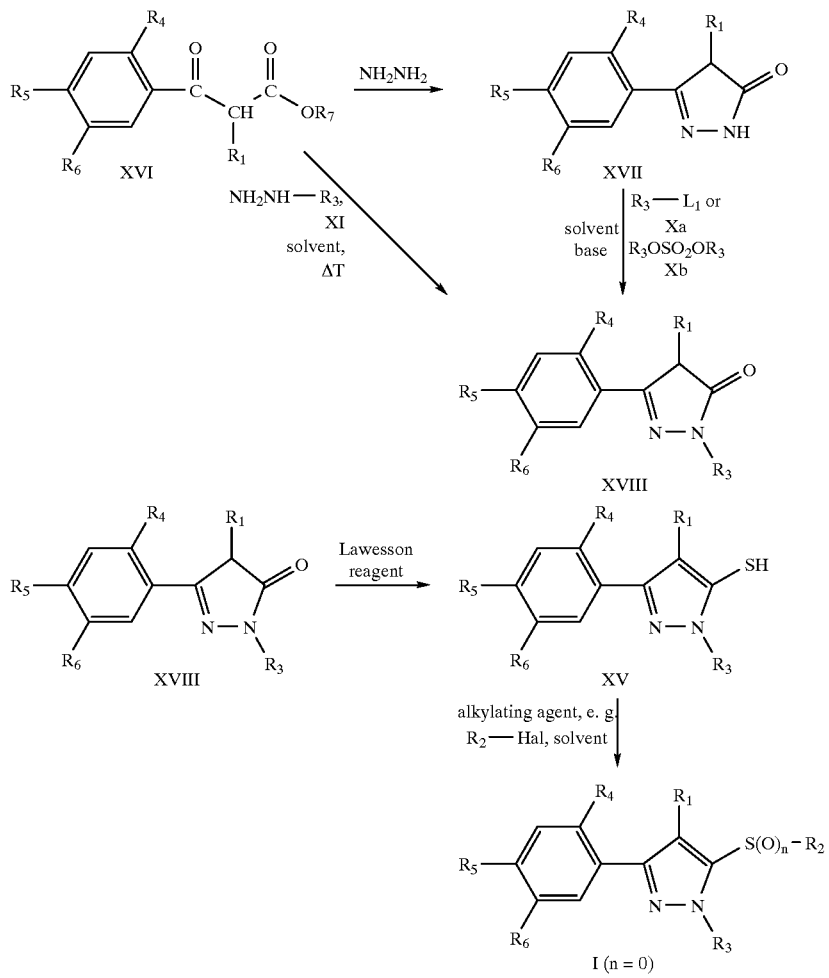

The formation of the pyrazole rings of the compounds of formula I according to Reaction Scheme 10 is carried out a) starting from the ketone derivative of formula IV wherein $R_1$ and $R_4$ to $R_6$ are as defined for formula I, by reaction with a carbonate of formula XVI wherein $R_7$ is $C_1$–$C_4$alkyl, phenyl or benzyl, in the presence of a base, especially the corresponding sodium alcoholate $R_7O^{-+}Na$, in a solvent, for example the corresponding alcohol $R_7OH$ together with a second solvent, for example an ether or hydrocarbon, at temperatures of from 0° C. to the boiling point of the solvent in question, or b) starting from the α-haloketone of formula XII wherein $R_1$ and $R_4$ to $R_6$ are as defined and Hal is halogen, especially chlorine or bromine, by carbonylation in the presence of the palladium(II) chloride-bis-triphenylphosphine complex $PdCl_2[(PH)_3P]_2$ as catalyst, carbon monoxide and a phase transfer catalyst in a suitable solvent, for example the alcohol $R_7OH$ wherein $R_7$ is as defined, together with a second solvent, for example N,N-di-methylformamide, analogously to Indian J. Chem. B 31,363 (1982).

In Reaction Scheme 10 the preparation of the pyrazolinone rings of formula XVII that are unsubstituted at the nitrogen atom is carried out by reaction of the above-prepared keto ester of formula XVI with hydrazine or hydrazine hydrate optionally in the presence of a suitable solvent at elevated temperature, preferably hydrazine hydrate in alcoholic solution at elevated temperature.

For the preparation of the pyrazolinone rings of formula XVIII that are substituted at the nitrogen atom, the reagent used is the compound of formula XI, for example N-alkyl-hydrazine, preferably N-methylhydrazine.

If desired, the substituted pyrazolinone derivative of formula XVIII can be prepared also via N-alkylation of the corresponding unsubstituted pyrazolinones of formula XVII, in a manner analogous to that described in Reaction Scheme 3.

The conversion of the pyrazolinone derivatives of formula XVIII into the corresponding mercapto analogues of formula XV is carried out in accordance with standard methods, for example with the aid of Lawesson reagent in a suitable solvent at elevated temperatures. The subsequent S-alkylation yields compounds of formula I (n=0) and is carried out in accordance with standard methods with the aid of an alkylating agent, for example $R_2$-Hal wherein $R_2$ is as defined for formula I and Hal is halogen, especially chlorine or bromine, optionally in the presence of a solvent and a base.

The compounds of formula XV are novel and have been developed especially for the synthesis of the compounds of formula I. They are therefore also a subject of the present invention.

All further compounds originating from the scope of formula I can easily be prepared from the described compounds of formula I in manner analogous to that described above, or in accordance with methods as described, for example, in "Methoden der Organischen Chemie" (Houben-Weyl), Volume E 8b, Georg Thieme Verlag Stuttgart, 1994, page 399 ff. or in "Pyrazoles, Pyrazolines, Pyrazolidines, Indazoles and Condensed Rings", Editor R. H. Wiley, Interscience Publishers, New York, 1967, page 1 ff., or by derivatisation in accordance with known standard methods, for example alkylation, acylation and amidation.

The end products of formula I can be isolated in customary manner by concentration and/or evaporation of the solvent and purified by recrystallisation or trituration of the solid residue in solvents in which they are not readily soluble, such as ethers, aromatic hydrocarbons or chlorinated hydrocarbons, by distillation or by means of column chromatography or flash column chromatography and a suitable eluant.

For the use according to the invention of the compounds of formula I, or compositions comprising them, there come into consideration all the methods of application customary in agriculture, for example pre-emergence application, post-emergence application and seed dressing, and also various methods and techniques, for example the controlled release of active ingredient. For that purpose a solution of the active ingredient is applied to mineral granule carriers or polymerised granules (urea/formaldehyde) and dried. If required, it is also possible to apply a coating (coated granules) which allows the active ingredient to be released in metered amounts over a specific period of time.

The compounds of formula I may be used in unmodified form, that is to say as obtained in the synthesis, but they are preferably formulated in customary manner together with the adjuvants customarily employed in formulation technology e.g. into emulsifiable concentrates, directly sprayable or diutable solution, dilute emulsions, wettable powders, soluble powders, dusts, granules or microcapsules. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures comprising the compound (active ingredient) of formula I or at least one compound of formula I and generally one or more solid or liquid formulation adjuvants, are prepared in known manner, e.g. by homogeneously mixing and/or grinding the active ingredients with the formulation adjuvants, e.g. solvents or solid carriers. It is also possible to use surface-active compounds (surfactants) in the preparation of the formulations.

Suitable solvents are: aromatic hydrocarbons, preferably the fractions containing 8 to 12 carbon atoms, such as mixtures of alkylbenzens, e.g. xylene mixtures or alkylated naphthalenes; aliphatic and cycloaliphatic hydrocarbons, such as paraffins, cyclohexane or tetrahydronaphthalene; alcohols, such as ethanol, propanol or butanol; glycols and their ethers and esters, such as propylene glycol or dipropylene glycol ether; ketones, such as cyclohexanone, isophorone or diacetone alcohol; strongly polar solvents, such as N-methyl-2-pyrrolidone, dimethyl sulfoxide or water, vegetable oils and esters thereof, such as rape oil, castor oil or soybean oil; and, where appropriate, also silicone oils.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great numer of pregranulated materials of inorganic or organic nature can be used, e.g. especially dolomite or pulverised plant residues.

Depending upon the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty alcohol sulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt or lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per rpopylene glycol unit.

Examples of non-ionic surfactants are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology, which may also be used in the compositions according to the invention, are described inter alia in "McCutcheon's Detergents and Emulsifiers Annual", MC Publishing Corp., Ridgewood, N.J., 1981; Stache, H., "Tensid-Taschenbuch" (Surfactant Handbook), Carl Hanser Verlag, Munich/Vienna 1981; and M. and J. Ash, "Encyclopedia of Surfactants", Vol. I–III, Chemical Publishing Co., New York, 1980–1981.

The herbicidal compositions usually comprise 0.1 to 99%, preferably 0.1 to 95%, of a compound of formula I, 1 to 99.9% of a solid or liquid formulation adjuvant, and 0 to 25%, preferably 0.1 to 25%, of a surfactant.

Whereas commercial products will preferably be formulated as concentrates, the end user will normally employ dilute formulations.

The compositions may also comprise further auxiliaries, such as stabilisers, e.g. vegetable oils or expoxidised vegetable oils (epoxidised coconut oil, rape oil or soybean oil), antifoams, e.g. silicone oil, preservatives, viscosity regulators, binders and tackifiers, as well as fertilisers or other active ingredients.

Preferred formulations have especially the following compositions (throughout, percentages are by weight):
Emulsifiable concentrates:
 active ingredient: 1 to 90%, preferably 5 to 50%
 surface-active agent: 5 to 30%, preferably 10 to 20%
 solvent: 15 to 94%, preferably 70 to 85%
Dusts:
 active ingredient: 0.1 to 50%, preferably 0.1 to 1%
 solid carrier: 99.9 to 90%, preferably 99.9 to 99%
Suspension concentrates:
 active ingredient: 5 to 75%, preferably 10 to 50%
 water: 94 to 24%, preferably 88 to 30%
 surface-active agent: 1 to 40%, preferably 2 to 30%
Wettable powders:
 active ingredient: 0.5 to 90%, preferably 1 to 80%
 surface-active agent: 0.5 to 20%, preferably 1 to 15%
 solid carrier: 5 to 95%, preferably 15 to 90%
Granules:
 active ingredient: 0.1 to 30%, preferably 0.1 to 15%
 solid carrier: 99.5 to 70%, preferably 97 to 85%

The compounds of formula I are generally used successfully when applied to the plant or to the locus thereof at rates of application of from 0.001 to 2 kg/ha, especially from 0.005 to 1 kg/ha. The concentration required to achieve the desired effect can be determined by experiment. It is dependent upon the type of action, the stage of development of the cultivated plant and of the weed, and also upon the application (place, time, method) and, in dependence on those parameters, can vary within wide limits.

The compounds of formula I are distinguished by herbicidal and growth-inhibiting properties which render them suitable for use in crops of useful plants, especially in cereals, cotton, soybeans, sugar beet, sugar cane, plantation crops, rape, maize and rice, and also for non-selective weed control.

Crops are also to be understood as being those which have been rendered tolerant to herbicides or classes of herbicide byu conventional methods of breeding or genetic engineering.

The following Examples further illustrate, but do not limit, the invention.

PREPARATION EXAMPLES

Example P1: 1-(2,4-Dichlorophenyl)-3,3-bis (methylthio)-2-methyl-2-propen-1-one

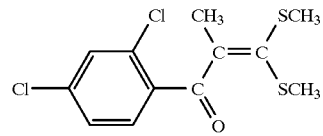

1.07 g (0.005 mol) of 1-(2,4-dichlorophenyl)-1-propanone (95%) are added to an emulsion of 0.24 g (0.01 mol) of sodium hydride in 8 ml of dry tetrahydrofuran and the mixture is stirred at 40° C. for one hour. The reaction mixture is cooled to 0° C. and 0.381 g (0.05 mol) of carbon disulfide is added at 0–5° C. Immediately after the addition of carbon disulfide is complete, 1.42 g (0.01 mol) of methyl iodide are added dropwise at 0–5° C. and the reaction mixture is stirred for one hour, then poured into 25 ml of a mixture of ice/water and stirred for a further 30 minutes. The crude produce is extracted with ether and the organic phase is separated off, dried over sodium sulfate and concentrated by evaporation. The resulting residue is purified by column chromatography using 10% ethyl acetate in hexane as eluant. The desired product is obtained in a yield of 1.38 g (89.8%) in the form of a yellow oil.

Example P2: 3-(2,4-Dichlorophenyl)-4-methyl-5-(methylthio)-1-methyl-[1H]-pyrazole

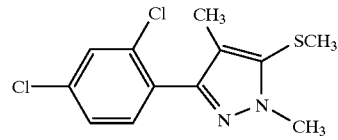

0.138 g (0.003 mol) of methyl hydrazine is added to a solution of 0.614 g (0.002 mol) of 1-(2,4-dichlorophenyl)-3,3-bis(methylthio)-2-methyl-2-propen-1-one in 10 ml of acetonitrile and the reaction mixture is heated at 80° C. for 8 hours. The mixture is then concentrated in vacuo and the residue is taken up in ether, washed with water and dried over sodium sulfate. After the ether phase has been concentrated by evaporation, the residue is purified by column chromatography over silica gel with hexane/ethyl acetate 2/1 as eluant. The desired product is obtained in a yield of 0.425 g (74.0%) in the form of a white solid having a melting point of 65–66° C. (recrystallised from hexane).

Example P3: 3-(2,4-Dichlorophenyl)-4-methyl-5-(methylsulfonyl)-1-methyl-[1H]-pyrazole

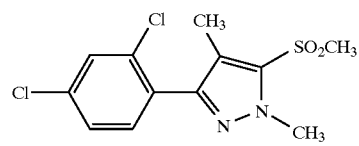

0.515 g (0.0015 mol) of m-chloroperbenzoic acid (50–60%) is added to a solution of 0.214 g (0.00075 mol) of 3-(2,4-dichlorophenyl)-4-methyl-5-(methylthio)-1-methyl-[1H]-pyrazole in 10 ml of dichlormethane and the reaction mixture is stirred at 22° C. overnight. The mixture is then washed with a saturated sodium hydrogen carbonate solution that contains 5% sodium thiosulfate and then with water, dried over sodium sulfate and concentrated by evaporation. The resulting residue is purified by column chromatography over silica gel with hexane/ethyl acetate 1/1. The desired product is obtained in a yield of 0.206 g (86.2%) in the form of a white solid having a melting point of 110–112° C.

Example P4: 3-(4-Chloro-2-fluorophenyl)-4-methyl-5-(methylthio)-[1H]-pyrazole

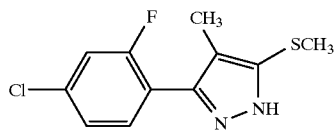

0.6 ml (0.01 mol) of carbon disulfide in 2 ml of ethanol is added dropwise at 20–28° C. to 3.35 ml (0.01 mol) of a 21% ethanolic sodium ethanolate solution and 0.49 ml (0.01 mol) of hydrazine hydrate in 10 ml of ethanol. After 0.5 hour's stirring at 22° C., 0.62 ml (0.01 mol) of methyl iodide is added dropwise at 20–22° C. to the suspension that has formed. After 1 hour's stirring at 22° C., 3.35 ml (0.01 mol) of 21% ethanolic sodium ethanolate solution are added to the resulting suspension and stirring is continued for a further 10 minutes. The resulting solution is then cooled to 5–10° C. and 2.7 g (0.01 mol) of α-bromo-4-chloro-2-fluoropropiophenone in 5 ml of ethanol are added dropwise to the solution and stirring is continued for a further 10 minutes at 40–45° C. 10 ml of 2N hydrochloric acid are added dropwise at 22° C. to the solution that has formed and stirring is continued for 1 hour at 22° C. and then for 15 minutes at 40–45° C. The resulting suspension is dissolved in tert-butyl methyl ether, washed three times with water and concentrated by evaporation using a rotary evaporator. As residue there is obtained 2.5 g of an oil which is chromatographed over 50 g of silica gel with ethyl acetate/hexane 1/2 as eluant. 1.4 g (54.6%) of the desired compound are obtained in the form of colourless crystals having a melting point of 88–90° C.

Example P5: α-Bromo-4-chloro-2-fluoropropiophenone

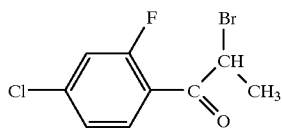

2.2 ml (0.42 mol) of bromine are added dropwise at 20–25° C. to a solution of 8.5 g (0.04 mol) of 4-chloro-2-fluoropropiophenone and 0.1 ml of 33% hydrobromic acid in 20 ml of acetic acid. After being stirred for 1 hour at 22° C., the mixture is poured into ice-water, extracted with tert-butyl methyl ether and washed neutral with dilute sodium hydrogen carbonate solution. The reaction mixture is then concentrated by evaporation using a rotary evaporator and then dried at 22° C. for 1 hour under a high vacuum. 10.4 g of 95% α-bromo-4-chloro-2-fluoropropiophenone and obtained in the form of a light-yellow oil.

Example P6: α-Bromo-4-chloro-2-fluoro-5-methoxypropiophenone

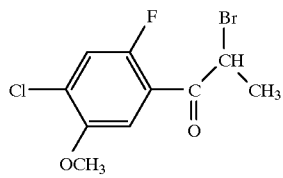

54 ml (1.05 mol) of bromine are added dropwise at 20–25° C. to a suspension of 217 g (1 mol) of 4-chloro-2-fluoro-5-methoxypropiophenone and 10 ml of 33% hydrobromic acid in glacial acetic acid in 0.5 liter of acetic acid. After being stirred for 1 hour to complete the reaction, the solution that has formed is poured into 2 liters of ice-water, extracted with tert-butyl methyl ether (MTBE), washed four times with water, dried over magnesium sulfate and concentrated by evaporation. 284 g of the desired compound are obtained in the form of a 95% oil.

Example P7: 3-(4-Chloro-2-fluoro-5-methoxyphenyl)-4-methyl-5-(methylthio)-[1H]-pyrazole

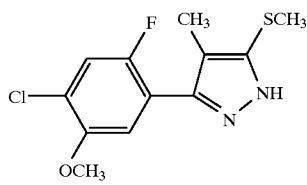

At 0–5° C., 37 g (0.3 mol) of methyl dithiocarbazate are added in portions to a solution of 120 ml (0.32 mol) of 21% sodium ethanolate solution in ethanol. 95 g (0.3 mol) of α-bromo-4-chloro-2-fluoro-5-methoxypropiophenone (90%) are added dropwise at −5–0° C. to the resulting solution. After being stirred for 30 minutes at 0–5° C., the suspension that has formed is diluted with 250 ml of ethanol and stirred at 0–5° C. for a further 2 hours. Then, after 1 hour's stirring at 22° C., 25 ml of 37% hydrochloric acid are added dropwise at 25–30° C. and stirring is continued for a further 3 hours. Then 30 ml of 30% sodium hydroxide solution are added dropwise and the resulting mixture is concentrated by evaporation. After the addition of about 1 liter of tert-butyl methyl ether, the reaction mixture is washed with water and the organic phase is dried and concentrated by evaporation. The crude product is purified by silica gel chromatography. 60 g (70% of the theoretical yield) of the desired compound are obtained in the form of brown crystals having a melting point of 95–100° C.

Example P8: 3-(4-Chloro-2-fluorophenyl)-4-methyl-5-(methylthio)-1-methyl-[1H]-pyrazole 1.4 ml (0.022 mol) of methyl iodide are added to a mixture of 5.4 g (0.02 mol) of 3-(4-chloro-2-fluorophenyl)-

4-methyl-5-(methylthio)-[1H]-pyrazole (Example P4) and 4.2 g (0.030 mol) of potassium carbonate in 25 ml of 1-methyl-2-pyrrolidone (NMP). After stirring overnight at 22° C., approximately 200 ml of tert-butyl methyl ether (MTBE) are added, and the mixture is washed three times with water and concentrated by evaporation. The crude product is purified by means of silica gel chromatography. 3.2 g (59% of the theoretical yield) of the desired compound are obtained in the form of an oil.

Example P9: 3-(4-Chloro-2-fluoro-5-hydroxyphenyl)-4-methyl-5-(methylthio)-1-methyl-[1H]-pyrazole

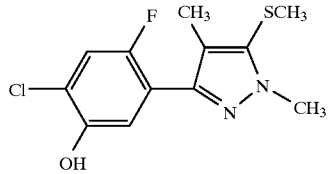

A mixture of 15 g (0.05 mol) of 3-(4-chloro-2-fluoro-5-methoxyphenyl)-4-methyl-5-(methylthio)-1-methyl-[1H]-pyrazole (Example P7) and 10.6 g (0.25 mol) of lithium chloride in 100 ml of N,N-dimethylformamide is stirred at 22° C. in an argon atomsphere for 2.5 days. The solution is cooled and poured into 0.5 liter of ice-water and 15 ml of 37% hydrochloric acid and extracted with tert-butyl methyl ether (MTBE). The organic phase is extracted with a dilute sodium hydroxide solution, and the aqueous phase is separated off and again acidified and extracted with MTBE. AFter concentration by evaporation and recrystallisation in diethyl ether, 4.8 g (33.5% of the threoretical yield) of the desired product are obtained in the form of crystals having a melting point of 136–138° C. and 7.6 g of crude product of the desired compound in the form of an oil.

Example P10: 3-(4-Chloro-2-fluoro-5-trifluoromethylsulfonyloxyphenyl)-4-methyl-5-(methylthio)-1-methyl-[1H]-pyrazole

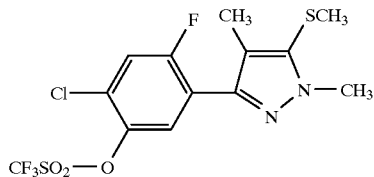

65 ml (0.8 mol) of pyridine and then 80 ml (0.48 mol) of trifluoromethanesulfonic acid anhydride are added dropwise at 0–5° C. to a solution of 129 g (0.3 mol) of 3-(4-chloro-2-fluoro- 5-hydroxyphenyl)-4-methyl-5-(methylthio)-1-methyl-[1H]-pyrazole (approx. 70%) (Example P9) in 1.2 liters of 1,4-dioxane. After being stirred for 30 minutes at 0–5° C. and then at 22° C. overnight, the reaction mixture is concentrated to approximately ⅓ of its original volume by evaporation, poured into a mixture of ice, water and hydrochloric acid, extracted with MTBE, washed with water and concentrated by evaporation. After purification of the crude product by silica gel chromatography, 87.7 g (70% of the theoretical yield) of the desired compound are isolated in the form of crystals having a melting point of 54–56° C.

Example P11: 3-(4-Chloro-2-fluoro-5-methoxycarbonylphenyl)-4-methyl-5-(methylthio)-1-methyl-[1H]-pyrazole

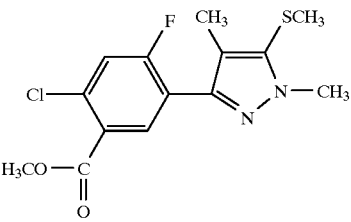

A mixture of 40.7 g (0.1 mol) of 3-(4-chloro-2-fluoro-5-trifluoromethylsulfonyloxyphenyl)-4-methyl-5-(methylthio)-1-methyl-[1H]-pyrazole (Example P10), 31 ml (0.22 mol) of triethylamine, 1.12 g (0.005 mol) of palladium (II) acetate and 2.06 g (0.005 mol) of 1,3-bis (diphenylphosphino)propane ($Ph_2P(CH_2)_3PPh_2$) in 300 ml of N,N-dimethylformamide and 215 ml of methanol is stirred at 70° C. at a pressure of 5 bar of carbon monoxide for 2 hours. The solution is then concentrated by evaporation, the resulting residue is dissolved in tert-butyl methyl ether (MTBE), washed with 0.2N hydrochloric acid and water, concentrated by evaporation and purified by means of silica gel column chromatography. 23.4 g (71.3% of the theoretical yield) of the desired compound are obtained in the form of crystals having a melting point of 82–83° C.

Example P12: 3-(4-Chloro-2-fluoro-5-proparglyoxyphenyl)-4-methyl-5-(methylthio)-1-methyl-[1H]-pyrazole

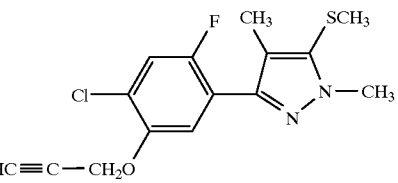

1 ml (0.0132 mol) of propargyl bromide are added dropwise at 20–25° C. to a mixture of 3.15 g (0.011 mol) of 3-(4-chloro-2-fluoro-5-hydroxyphenyl)-4-methyl-5-(methylthio)-1-methyl-[1H]-pyrazole (Example P9) and 2.5 g (0.018 mol) of potassium carbonate in 30 ml of N,N-dimethylformamide. After being stirred for 18 hours at 22° C., the mixture is poured into water, extracted with tert-butyl methyl ether (MTBE), washed with water and concentrated by evaporation. After recrystallisation in petroleium ether, 2.84 g (81.1% of the theoretical yield) of the desired compound are obtained in the form of crystals having a melting point of 76–78° C.

Example P13: 3-(4-Chloro-2-fluoro-5-propargyloxyphenyl)-4-methyl-5-(methylsulfinyl)-1-methyl-[1H]-pyrazole

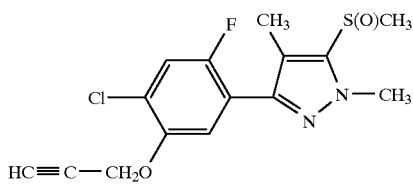

A solution of 1.57 g (0.005 mol) of 50–60% 3-chloroperbenzoic acid in 30 ml of dichloromethane is added dropwise at 0–5° C. to a solution of 1.7 g (0.005 mol) of 3-(4-chloro-2-fluoro-5-propargyloxyphenyl)-4-methyl-5-(methylthio)-1-methyl-[1H]-pyrazole (Example P12) in 20 ml of dichloromethane. After being stirred overnight at 22° C., the reaction mixture is washed with a dilute sodium hydrogen carbonate solution, then with water and concentrated by evaporation, and the resulting residue is recrystallised in petroleum ether/diethyl ether. 1.5 g (88.2% of the theoretical yield) of the desired compound are isolated in the form of crystals having a melting point of 93–96° C.

Example P14: 3-(4-Chloro-2-fluoro-5-propargyloxyphenyl)-4-methyl-5-(methylsulfonyl)-1-methyl-[1H]-pyrazole

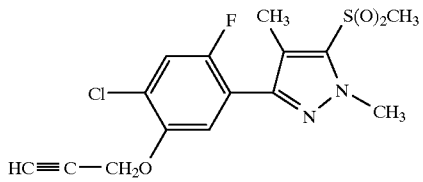

A solution of 3.45 g (0.011 mol) of 50–60% 3-chlroperbenzoic acid in 60 ml of dichlormethane is added dropwise at 0–5° C. to a solution of 1.7 g (0.005 mol) of 3-(4-chloro-2-fluoro-5-propargyloxyphenyl)-4-methyl-5-(methylthio)-1-methyl-[1H]-pyrazole (Example P12) in 20 ml of dichloromethane. After being stirred overnight at 22° C., the reaction mixture is washed with a dilute sodium hydrogen carbonate solution, then with water and concentrated by evaporation, and the resulting residue is recrystallised in diethyl ether. 1.4 g (78.6% of the theoretical yield) of the desired compound are obtained in the form of crystals having a melting point of 123–124° C.

In an analogous manner or by means of known methods it is also possible to prepare the compounds listed in the Tables which follow.

TABLE 1

Compounds of formula Ia

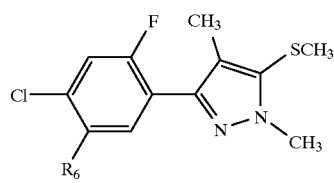

| Comp. No. | $R_6$ | M.p. |
|---|---|---|
| 1.1 | H | oil |
| 1.2 | $NH_2$ | 55–60 |
| 1.3 | $NO_2$ | |
| 1.4 | Br | |
| 1.5 | I | |
| 1.6 | CN | |
| 1.7 | $OCH_3$ | 64–70 |
| 1.8 | $N(SO_2CH_3)_2$ | |
| 1.9 | $NHSO_2CH_3$ | 142–144 |
| 1.10 | $OC_3H_7(iso)$ | oil |
| 1.11 | O-propargyl | 72–75 |
| 1.12 | $OCH(CH_3)C\equiv CH$ | oil |
| 1.13 | O-phenyl | |
| 1.14 | O-2-pyridyl | |
| 1.15 | O-2-pyrimidinyl | |
| 1.16 | $OCH_2COOCH_2CH_3$ | 95–97 |
| 1.17 | $OCH_2CH_2OCH_3$ | |
| 1.18 | $OCH_2CH_2SCH_2CH_3$ | |
| 1.19 | $OCH_2COOCH_3$ | |
| 1.20 | $OCH_2COOC_5H_{11}(n)$ | |
| 1.21 | $OCH_2COO$-benzyl | |
| 1.22 | $OCH(CH_3)COObenzyl$ (S) | |
| 1.23 | $OCH(CH_3)COObenzyl$ (R) | |
| 1.24 | $OCH(CH_3)COObenzyl$ (R,S) | |
| 1.25 | $SC_3H_7(iso)$ | |
| 1.26 | SH | solid |
| 1.27 | $SCH_2COOCH_3$ | oil |
| 1.28 | $SCH_2COOC_2H_5$ | |
| 1.29 | $SCH(CH_3)COObenzyl$ (S) | |
| 1.30 | $SCH(CH_3)COObenzyl$ (R) | |
| 1.31 | $SCH(CH_3)COObenzyl$ (R,S) | |
| 1.32 | $SCH_2COObenzyl$ | |
| 1.33 | $SO_2Cl$ | solid |
| 1.34 | $SO_2CH_3$ | |
| 1.35 | $SO_2NHCH_3$ | |
| 1.36 | COOH | 177–179 |
| 1.37 | $COOCH_3$ | 82–83 |
| 1.38 | $COOC_3H_7(iso)$ | oil |
| 1.39 | $COOC(CH_3)_2COOH$ | amorphous |
| 1.40 | $COOC(CH_3)_2COO$-allyl | oil |
| 1.41 | $COOC(CH_3)_2COOCH_3$ | |
| 1.42 | $COOC(CH_3)_2COOethyl$ | 72–75 |
| 1.43 | $COOC(CH_3)_2CONH$-allyl | |
| 1.44 | $CH_2CHClCOOethyl$ | oil |
| 1.45 | $CH_2CH=CH_2$ | oil |
| 1.46 | $CH_2CH_2CH_3$ | |
| 1.47 | $CH_2CH_2CF_3$ | |
| 1.48 | $OCH(CH_3)COOC_2H_5(R)$ | |
| 1.49 | $OCH(CH_3)COOC_2H_5(S)$ | |
| 1.50 | $OCH(CH_3)COOC_2H_5(R,S)$ | oil |
| 1.51 | $CH_2CHClCOOH$ | 170–172 |
| 1.52 | $CH_2CHClCOOCH_3$ | |
| 1.53 | $CH_2CHClCOOC_3H_7(iso)$ | |
| 1.54 | $CH_2CHClCONHallyl$ | |
| 1.55 | $CH_2C(CH_3)ClCOOH$ | |
| 1.56 | $CH_2C(CH_3)ClCOOC_2H_5$ | oil |
| 1.57 | $CH_2C(CH_3)ClCOOEt$ | |
| 1.58 | $CH_2C(CH_3)ClCONHEt$ | |
| 1.59 | $CH_2CH_2COOH$ | |
| 1.60 | $CH_2CH_2COOCH_3$ | |
| 1.61 | $CH_2CH_2COOEt$ | |
| 1.62 | $CHClCHClCOOH$ | |
| 1.63 | $CHClCHClCOOCH_3$ | |
| 1.64 | $CHClCHClCOOEt$ | |

TABLE 1-continued

Compounds of formula Ia

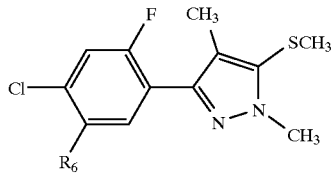
(Ia)

| Comp. No. | $R_6$ | M.p. |
|---|---|---|
| 1.65 | $CH_2CH(OCH_3)COOH$ | |
| 1.66 | $CH_2CH(OCH_3)COOCH_3$ | |
| 1.67 | $CH_2CH(OCH_3)COOEt$ | |
| 1.68 | $CH_2CH(SCH_3)COOH$ | |
| 1.69 | $CH_2CH(SCH_3)COOCH_3$ | |
| 1.70 | $CH_2CH(SCH_3)COOEt$ | oil |
| 1.71 | $CH=CHCOOH$ | |
| 1.72 | $CH=CHCOOCH_3$ | |
| 1.73 | $CH=CHCOOEt$ | |
| 1.74 | $CH=CClCOOH$ | |
| 1.75 | $CH=CClCOOCH_3$ | |
| 1.76 | $COOEt$ | |
| 1.77 | $CONH_2$ | |
| 1.78 | —C(O)O—CH$_2$—(epoxide) | 55–57 |
| 1.79 | $CONHSO_2CH_3$ | |
| 1.80 | $COOCH_2COOH$ | |
| 1.81 | $COOCH_2COOCH_3$ | |
| 1.82 | $COOCH(CH_3)COOH$ | |
| 1.83 | $COOCH(CH_3)COOCH_3$ | |
| 1.84 | $COOCH(CH_3)CH_2COOH$ | |
| 1.85 | $COOCH(CH_3)CH_2COOCH_3$ | |
| 1.86 | $COOC(CH_3)_2CN$ | |
| 1.87 | $COOCH_2CH_2OCH_3$ | |
| 1.88 | $COOC(CH_3)_2COOCH_2CH_2OCH_3$ | |
| 1.89 | $COOC(CH_3)_2$—C(O)O—CH$_2$—(epoxide) | 59–62 |
| 1.90 | $COOC(CH_3)_2COOCH_2PHENYL$ | oil |
| 1.91 | $COOCH_2C\equiv CH$ | |
| 1.92 | $COOC(CH_3)_2COOCH_2C\equiv CH$ | |
| 1.93 | $COOCH(CH_3)C\equiv CH$ | |
| 1.94 | $COOC(CH_3)_2COCH_3$ | |
| 1.95 | NHallyl | |
| 1.96 | $N(COCH_3)$allyl | |
| 1.97 | $N(Et)SO_2CH_3$ | |
| 1.98 | $N(allyl)SO_2CH_3$ | 83–85 |
| 1.99 | $N(allyl)SO_2Et$ | 65–68 |
| 1.100 | $SO_2N(CH_3)_2$ | |
| 1.101 | $SO_2NH_2$ | |
| 1.102 | $SO_2NHCOCH_3$ | |
| 1.103 | OH | oil |
| 1.104 | OEt | |
| 1.105 | Oallyl | |
| 1.106 | $OCH_2C\equiv CCH_3$ | |
| 1.107 | $OCH(CH_3)CH=CH_2$ | |
| 1.108 | $OCH_2CH_2OCH_2CH_3$ | |
| 1.109 | $OCH_2CH_2OCH_2CH_2OCH_3$ | oil |
| 1.110 | $OCH_2$—(epoxide) | 86–89 |
| 1.111 | $OCH_2CH_2NHCH_3$ | |
| 1.112 | $OCH_2CH_2N(CH_3)COCH_3$ | |
| 1.113 | $OCH_2CH_2COOH$ | |
| 1.114 | $OC(CH_3)_2COOH$ | |
| 1.115 | $OC(CH_3)_2COOCH_3$ | |
| 1.116 | $OC(CH_3)_2COOEt$ | |

TABLE 1-continued

Compounds of formula Ia

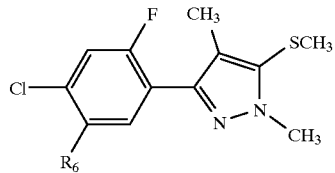
(Ia)

| Comp. No. | $R_6$ | M.p. |
|---|---|---|
| 1.117 | $OCH_2COOH$ | |
| 1.118 | $OSO_2CH_3$ | |
| 1.119 | $OSO_2CF_3$ | 54–56 |
| 1.120 | $CH_2CHClCOOC_2H_5$ | |
| 1.121 | $CH_2CHClCON(C_2H_5)_2$ | |
| 1.122 | $CH_2CHClCONHOH$ | |
| 1.123 | $CH_2CHClCOOCH_2C_6H_5$ | |
| 1.124 | $CH_2CH(CH_3)COOH$ | |
| 1.125 | $CH_2CH(CH_3)COOC_2H_5$ | |
| 1.126 | —COOCH$_2$—cyclopropyl | |
| 1.127 | $COOC(CH_3)_2COOCH_2CH_2OC_2H_5$ | |
| 1.128 | —COOC(CH$_3$)$_2$COOCH$_2$—cyclopropyl | |
| 1.129 | $COOC(CH_3)_2CONHCH_2C\equiv CH$ | |
| 1.130 | $COOC(CH_3)_2CON(CH_2CH_3)_2$ | |
| 1.131 | $OCH_2$—cyclopropyl | 91–93 |
| 1.132 | $NHSO_2C_2H_5$ | 121–124 |
| 1.133 | $NHCH_2C\equiv CH$ | 103–105 |

TABLE 2

Compounds of formula Ib

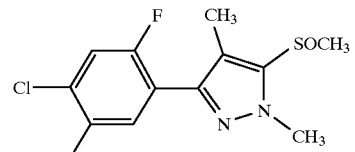
(Ib)

| Comp. No. | $R_6$ | M.p. |
|---|---|---|
| 2.1 | H | 113–115 |
| 2.2 | $NH_2$ | solid |
| 2.3 | $NO_2$ | 128–130 |
| 2.4 | Br | |
| 2.5 | I | |
| 2.6 | CN | |
| 2.7 | $OCH_3$ | 89–92 |
| 2.8 | $N(SO_2CH_3)_2$ | |
| 2.9 | $NHSO_2CH_3$ | |
| 2.10 | $OC_3H_7(iso)$ | oil |
| 2.11 | O-propargyl | 93–96 |
| 2.12 | $OCH(CH_3)C\equiv CH$ | resin |
| 2.13 | O-phenyl | |
| 2.14 | O-2-pyridyl | |
| 2.15 | O-2-pyrimidinyl | |
| 2.16 | $OCH_2COOC_2H_5$ | 95–98 |

TABLE 2-continued

Compounds of formula Ib

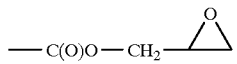

(Ib)

| Comp. No. | R₆ | M.p. |
|---|---|---|
| 2.17 | OCH₂COOC₅H₁₁(n) | |
| 2.18 | OCH₂COO-benzyl | |
| 2.19 | OCH(CH₃)COObenzyl (S) | |
| 2.20 | OCH(CH₃)COObenzyl (R) | |
| 2.21 | OCH(CH₃)COObenzyl (R,S) | |
| 2.22 | SC₃H₇(iso) | |
| 2.23 | SH | |
| 2.24 | SCH₂COOCH₃ | |
| 2.25 | SCH₂COOC₂H₅ | |
| 2.26 | SCH(CH₃)COObenzyl (S) | |
| 2.27 | SCH(CH₃)COObenzyl (R) | |
| 2.28 | SCH(CH₃)COObenzyl (R,S) | |
| 2.29 | SCH₂COObenzyl | |
| 2.30 | SO₂Cl | |
| 2.31 | SO₂CH₃ | |
| 2.32 | SO₂NHCH₃ | |
| 2.33 | COOH | 138–164 |
| 2.34 | COOCH₃ | oil |
| 2.35 | COOC₃H₇(iso) | oil |
| 2.36 | COOC(CH₃)₂COOH | 153–166 |
| 2.37 | COOC(CH₃)₂COO-allyl | oil |
| 2.38 | COOC(CH₃)₂COOCH₃ | |
| 2.39 | COOC(CH₃)₂COOethyl | oil |
| 2.40 | COOC(CH₃)₂CONH-allyl | |
| 2.41 | CH₂CHClCOOethyl | resin |
| 2.42 | CH₂CH=CH₂ | 99–101 |
| 2.43 | CH₂CH₂CH₃ | |
| 2.44 | CH₂CH₂CF₃ | |
| 2.45 | OCH(CH₃)COOC₂H₅ (R) | |
| 2.46 | OCH(CH₃)COOC₂H₅ (S) | |
| 2.47 | OCH(CH₃)COOC₂H₅ (R,S) | oil |
| 2.48 | CH₂CHClCOOH | |
| 2.49 | CH₂CHClCOOCH₃ | |
| 2.50 | CH₂CHClCOOC₃H₇(iso) | |
| 2.51 | CH₂CHClCONHallyl | |
| 2.52 | CH₂C(CH₃)ClCOOH | |
| 2.53 | CH₂C(CH₃)ClCOOCH₃ | |
| 2.54 | CH₂C(CH₃)ClCOOEt | oil |
| 2.55 | CH₂C(CH₃)ClCONHEt | |
| 2.56 | CH₂CH₂COOH | |
| 2.57 | CH₂CH₂COOCH₃ | |
| 2.58 | CH₂CH₂COOEt | |
| 2.59 | CHClCHClCOOH | |
| 2.60 | CHClCHClCOOCH₃ | |
| 2.61 | CHClCHClCOOEt | |
| 2.62 | CH₂CH(OCH₃)COOH | |
| 2.63 | CH₂CH(OCH₃)COOCH₃ | |
| 2.64 | CH₂CH(OCH₃)COOEt | |
| 2.65 | CH₂CH(SCH₃)COOH | |
| 2.66 | CH₂CH(SCH₃)COOCH₃ | |
| 2.67 | CH₂CH(SCH₃)COOEt | |
| 2.68 | CH=CHCOOH | |
| 2.69 | CH=CHCOOCH₃ | |
| 2.70 | CH=CHCOOEt | |
| 2.71 | CH=CClCOOH | |
| 2.72 | CH=CClCOOCH₃ | |
| 2.73 | COOEt | |
| 2.74 | CONH₂ | |
| 2.75 | —C(O)O—CH₂—(epoxide) | 68–71 |
| 2.76 | CONHSO₂CH₃ | |
| 2.77 | COOCH₂COOH | |
| 2.78 | COOCH₂COOCH₃ | |
| 2.79 | COOCH(CH₃)COOH | |
| 2.80 | COOCH(CH₃)COOCH₃ | |
| 2.81 | COOCH(CH₃)CH₂COOH | |
| 2.82 | COOCH(CH₃)CH₂COOCH₃ | |
| 2.83 | COOC(CH₃)₂CN | |
| 2.84 | COOCH₂CH₂OCH₃ | |
| 2.85 | COOC(CH₃)₂COOCH₂CH₂OCH₃ | |
| 2.86 | COOC(CH₃)₂—C(O)O—CH₂—(epoxide) | |
| 2.87 | COOC(CH₃)₂COOCH₂PHENYL | 91–93 |
| 2.88 | COOCH₂C≡CH | |
| 2.89 | COOC(CH₃)₂COOCH₂C≡CH | |
| 2.90 | COOCH(CH₃)C≡CH | |
| 2.91 | COOC(CH₃)₂COCH₃ | |
| 2.92 | NHallyl | |
| 2.93 | N(COCH₃)allyl | |
| 2.94 | N(Et)SO₂CH₃ | |
| 2.95 | N(allyl)SO₂CH₃ | 133–136 |
| 2.96 | N(allyl)SO₂Et | solid |
| 2.97 | SO₂N(CH₃)₂ | |
| 2.98 | SO₂NH₂ | |
| 2.99 | SO₂NHCOCH₃ | |
| 2.100 | OH | |
| 2.101 | OEt | |
| 2.102 | Oallyl | |
| 2.103 | OCH₂C≡CCH₃ | |
| 2.104 | OCH(CH₃)CH=CH₂ | |
| 2.105 | OCH₂CH₂OCH₂CH₃ | |
| 2.106 | OCH₂CH₂OCH₂CH₂OCH₃ | oil |
| 2.107 | OCH₂—(epoxide) | 96–99 |
| 2.108 | OCH₂CH₂NHCH₃ | |
| 2.109 | OCH₂CH₂N(CH₃)COCH₃ | |
| 2.110 | OCH₂CH₂COOH | |
| 2.111 | OC(CH₃)₂COOH | |
| 2.112 | OC(CH₃)₂COOCH₃ | |
| 2.113 | OC(CH₃)₂COOEt | |
| 2.114 | OCH₂COOH | |
| 2.115 | OSO₂CH₃ | |
| 2.116 | OSO₂CF₃ | |
| 2.117 | CH₂CHClCOOC₂H₅ | |
| 2.118 | CH₂CHClCON(C₂H₆)₂ | |
| 2.119 | CH₂CHClCONHOH | |
| 2.120 | CH₂CHClCOOCH₂C₆H₅ | |
| 2.121 | CH₂CH(CH₃)COOH | |
| 2.122 | CH₂CH(CH₃)COOC₂H₅ | |
| 2.123 | —COOCH₂—(cyclopropyl) | |
| 2.124 | COOC(CH₃)₂COOCH₂CH₂OC₂H₅ | |
| 2.125 | —COOC(CH₃)₂COOCH₂—(cyclopropyl) | |

TABLE 2-continued

Compounds of formula Ib

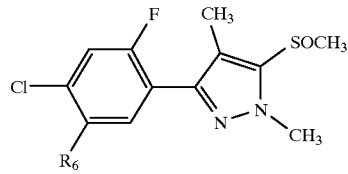

(Ib)

| Comp. No. | R₆ | M.p. |
|---|---|---|
| 2.126 | COOC(CH₃)₂CONHCH₂C≡CH | |
| 2.127 | COOC(CH₃)₂CON(CH₂CH₃)₂ | |
| 2.128 | OCH₂—◁ | 96–98 |

TABLE 3

Compounds of formula Ic

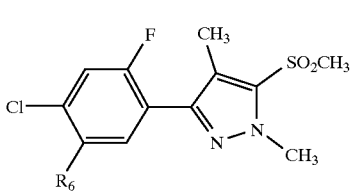

(Ic)

| Comp. No. | R₆ | M.p |
|---|---|---|
| 3.1 | H | 113–115 |
| 3.2 | NH₂ | |
| 3.3 | NO₂ | |
| 3.4 | Br | |
| 3.5 | I | |
| 3.6 | CN | |
| 3.7 | OCH₃ | 146–149 |
| 3.8 | N(SO₂CH₃)₂ | |
| 3.9 | NHSO₂CH₃ | 199–201 |
| 3.10 | OC₃H₇(iso) | 100–103 |
| 3.11 | O-propargyl | 123–124 |
| 3.12 | OCH(CH₃)C≡CH | oil |
| 3.13 | O-phenyl | |
| 3.14 | O-2-pyridyl | |
| 3.15 | O-2-pyrimidinyl | |
| 3.16 | OCH₂COOC₂H₅ | 123–126 |
| 3.17 | OCH₂COOCH₃ | |
| 3.18 | OCH₂COO-benzyl | |
| 3.19 | OCH(CH₃)COObenzyl (S) | |
| 3.20 | OCH(CH₃)COObenzyl (R) | |
| 3.21 | OCH(CH₃)COObenzyl (R,S) | |
| 3.22 | SC₃H₇(iso) | |
| 3.23 | SH | |
| 3.24 | SCH₂COOCH₃ | |
| 3.25 | SCH₂COOC₂H₅ | |
| 3.26 | SCH(CH₃)COObenzyl (S) | |
| 3.27 | SCH(CH₃)COObenzyl (R) | |
| 3.28 | SCH(CH₃)COObenzyl (R,S) | |
| 3.29 | SCH₂COObenzyl | |
| 3.30 | SO₂Cl | |
| 3.31 | SO₂CH₃ | |
| 3.32 | SO₂NHCH₃ | |
| 3.33 | COOH | 237–240 |
| 3.34 | COOCH₃ | 94–96 |
| 3.35 | COOC₃H₇(iso) | 92–94 |
| 3.36 | COOC(CH₃)₂COOH | 167–169 |
| 3.37 | COOC(CH₃)₂COO-allyl | oil |
| 3.38 | COOC(CH₃)₂COOCH₃ | |

TABLE 3-continued

Compounds of formula Ic

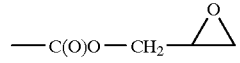

(Ic)

| Comp. No. | R₆ | M.p |
|---|---|---|
| 3.39 | COOC(CH₃)₂COOethyl | oil |
| 3.40 | COOC(CH₃)₂CONH-allyl | |
| 3.41 | CH₂CHClCOOethyl | resin |
| 3.42 | CH₂CH═CH₂ | 98–100 |
| 3.43 | CH₂CH₂CH₃ | |
| 3.44 | CH₂CH₂CF₃ | |
| 3.45 | OCH(CH₃)COOC₂H₅ (R) | |
| 3.46 | OCH(CH₃)COOC₂H₅ (S) | |
| 3.47 | OCH(CH₃)COOC₂H₅ (R,S) | oil |
| 3.48 | CH₂CHClCOOH | |
| 3.49 | CH₂CHClCOOCH₃ | |
| 3.50 | CH₂CHClCOOC₃H₇(iso) | |
| 3.51 | CH₂CHClCONHallyl | |
| 3.52 | CH₂C(CH₃)ClCOOH | |
| 3.53 | CH₂C(CH₃)ClCOOCH₃ | |
| 3.54 | CH₂C(CH₃)ClCOOEt | oil |
| 3.55 | CH₂C(CH₃)ClCONHEt | |
| 3.56 | CH₂CH₂COOH | |
| 3.57 | CH₂CH₂COOCH₃ | |
| 3.58 | CH₂CH₂COOEt | |
| 3.59 | CHClCHClCOOH | |
| 3.60 | CHClCHClCOOCH₃ | |
| 3.61 | CHClCHClCOOEt | |
| 3.62 | CH₂CH(OCH₃)COOH | |
| 3.63 | CH₂CH(OCH₃)COOCH₃ | |
| 3.64 | CH₂CH(OCH₃)COOEt | |
| 3.65 | CH₂CH(SCH₃)COOH | |
| 3.66 | CH₂CH(SCH₃)COOCH₃ | |
| 3.67 | CH₂CH(SCH₃)COOEt | |
| 3.68 | CH═CHCOOH | |
| 3.69 | CH═CHCOOCH₃ | |
| 3.70 | CH═CHCOOEt | |
| 3.71 | CH═CClCOOH | |
| 3.72 | CH═CClCOOCH₃ | |
| 3.73 | COOEt | |
| 3.74 | CONH₂ | |
| 3.75 | —C(O)O—CH₂—◁O | 110–112 |
| 3.76 | CONHSO₂CH₃ | |
| 3.77 | COOCH₂COOH | |
| 3.78 | COOCH₂COOCH₃ | |
| 3.79 | COOCH(CH₃)COOH | |
| 3.80 | COOCH(CH₃)COOCH₂ | |
| 3.81 | COOCH(CH₃)CH₂COOH | |
| 3.82 | COOCH(CH₃)CH₂COOCH₃ | |
| 3.83 | COOC(CH₃)₂CN | |
| 3.84 | COOCH₂CH₂OCH₃ | |
| 3.85 | COOC(CH₃)₂COOCH₂CH₂OCH₃ | |
| 3.86 | COOC(CH₃)₂—C(O)O—CH₂—◁O | oil |
| 3.87 | COOC(CH₃)₂COOCH₂PHENYL | 83–86 |
| 3.88 | COOCH₂C≡CH | |
| 3.89 | COOC(CH₃)₂COOCH₂C≡CH | |
| 3.90 | COOCH(CH₃)C≡CH | |
| 3.91 | COOC(CH₃)₂COCH₃ | |
| 3.92 | NHallyl | |
| 3.93 | N(COCH₃)allyl | |

TABLE 3-continued

Compounds of formula Ic (Ic)

| Comp. No. | R₆ | M.p |
|---|---|---|
| 3.94 | N(Et)SO₂CH₃ | |
| 3.95 | N(allyl)SO₂CH₃ | 120–122 |
| 3.96 | N(allyl)SO₂Et | 105–107 |
| 3.97 | SO₂N(CH₃)₂ | |
| 3.98 | SO₂NH₂ | |
| 3.99 | SO₂NHCOCH₃ | |
| 3.100 | OH | |
| 3.101 | OEt | |
| 3.102 | Oallyl | |
| 3.103 | OCH₂C≡CCH₃ | |
| 3.104 | OCH(CH₃)C=CH₂ | |
| 3.105 | OCH₂CH₂OCH₂CH₃ | |
| 3.106 | OCH₂CH₂OCH₂CH₂OCH₃ | 51–55 |
| 3.107 | OCH₂—(epoxide) | 125–127 |
| 3.108 | OCH₂CH₂NHCH₃ | |
| 3.109 | OCH₂CH₂N(CH₃)COCH₃ | |
| 3.110 | OCH₂CH₂COOH | |
| 3.111 | OC(CH₃)₂COOH | |
| 3.112 | OC(CH₃)₂COOCH₃ | |
| 3.113 | OC(CH₃)₂COOEt | |
| 3.114 | OCH₂COOH | |
| 3.115 | OSO₂CH₃ | |
| 3.116 | OSO₂CF₃ | |
| 3.117 | CH₂CHClCOOC₂H₅ | |
| 3.118 | CH₂CHClCON(C₂H₅)₂ | |
| 3.119 | CH₂CHClCONHOH | |
| 3.120 | CH₂CHClCOOCH₂C₆H₅ | |
| 3.121 | CH₂CH(CH₃)COOH | |
| 3.122 | CH₂CH(CH₃)COOC₂H₅ | |
| 3.123 | —COOCH₂—cyclopropyl | |
| 3.124 | COOC(CH₃)₂COOCH₂CH₂OC₂H₅ | |
| 3.125 | —COOC(CH₃)₂COOCH₂—cyclopropyl | |
| 3.126 | COOC(CH₃)₂CONHCH₂C≡CH | |
| 3.127 | COOC(CH₃)₂CON(CH₂CH₃)₂ | |
| 3.128 | OCH₂—cyclopropyl | 108–109 |

TABLE 4

Compounds of formula Id (Id)

| Comp. No. | R₆ | M.p. |
|---|---|---|
| 4.1 | H | 69–71 |
| 4.2 | NH₂ | oil |
| 4.3 | NO₂ | |
| 4.4 | Br | |
| 4.5 | I | 74–77 |
| 4.6 | CN | |
| 4.7 | OCH₃ | |
| 4.8 | N(SO₂CH₃)₂ | |
| 4.9 | NHSO₂CH₃ | |
| 4.10 | OC₃H₇(iso) | |
| 4.11 | O-propargyl | |
| 4.12 | OCH(CH₃)C≡CH | |
| 4.13 | OCH₂COOCH₂CH₃ | |
| 4.14 | OCH₂CH₂OCH₃ | |
| 4.15 | OCH₂CH₂SCH₂CH₃ | |
| 4.16 | OCH₂COOCH₃ | |
| 4.17 | OCH₂COOC₅H₁₁(n) | |
| 4.18 | OCH₂COO-benzyl | |
| 4.19 | OCH(CH₃)COObenzyl (S) | |
| 4.20 | OCH(CH₃)COObenzyl (R) | |
| 4.21 | OCH(CH₃)COObenzyl (R,S) | |
| 4.22 | SC₃H₇(iso) | |
| 4.23 | SH | |
| 4.24 | SCH₂COOCH₃ | |
| 4.25 | SCH₂COOC₂H₅ | |
| 4.26 | SCH(CH₃)COObenzyl (S) | |
| 4.27 | SCH(CH₃)COObenzyl (R) | |
| 4.28 | SCH(CH₃)COObenzyl (R,S) | |
| 4.29 | SCH₂COObenzyl | |
| 4.30 | SO₂Cl | |
| 4.31 | SO₂CH₃ | |
| 4.32 | SO₂NHCH₃ | |
| 4.33 | COOH | 150–151 |
| 4.34 | COOCH₃ | 60–61 |
| 4.35 | COOC₃H₇(iso) | oil |
| 4.36 | COOC(CH₃)₂COOH | 184–188 |
| 4.37 | COOC(CH₃)₂COO-allyl | |
| 4.38 | COOC(CH₃)₂COOCH₃ | |
| 4.39 | COOC(CH₃)₂COOethyl | 52–55 |
| 4.40 | COOC(CH₃)₂CONH-allyl | |
| 4.41 | CH₂CHClCOOethyl | |
| 4.42 | CH₂CH=CH₂ | |
| 4.43 | CH₂CH₂CH₃ | |
| 4.44 | CH₂CH₂CF₃ | |
| 4.45 | OCH(CH₃)COOC₂H₅(R) | |
| 4.46 | OCH(CH₃)COOC₂H₅(S) | |
| 4.47 | OCH(CH₃)COOC₂H₅(R,S) | |
| 4.48 | CH₂CHClCOOH | |
| 4.49 | CH₂CHClCOOCH₃ | |
| 4.50 | CH₂CHClCOOC₃H₇(iso) | |
| 4.51 | CH₂CHClCONHallyl | |
| 4.52 | CH₂C(CH₃)ClCOOH | |
| 4.53 | CH₂C(CH₃)ClCOOCH₃ | |
| 4.54 | CH₂C(CH₃)ClCOOEt | |
| 4.55 | CH₂C(CH₃)ClCONHEt | |
| 4.56 | CH₂CH₂COOH | |
| 4.57 | CH₂CH₂COOCH₃ | |
| 4.58 | CH₂CH₂COOEt | |
| 4.59 | CHClCHClCOOH | |
| 4.60 | CHClCHClCOOCH₃ | |
| 4.61 | CHClCHClCOOEt | |
| 4.62 | CH₂CH(OCH₃)COOH | |
| 4.63 | CH₂CH(OCH₃)COOCH₃ | |
| 4.64 | CH₂CH(OCH₃)COOEt | |

TABLE 4-continued

Compounds of formula Id (Id) structure: 3-(4-chloro-3-R₆-phenyl)-4-methyl-5-(SCH₃)-1-methyl-pyrazole

| Comp. No. | R₆ | M.p. |
|---|---|---|
| 4.65 | CH₂CH(SCH₃)COOH | |
| 4.66 | CH₂CH(SCH₃)COOCH₃ | |
| 4.67 | CH₂CH(SCH₃)COOEt | |
| 4.68 | CH=CHCOOH | |
| 4.69 | CH=CHCOOCH₃ | |
| 4.70 | CH=CHCOOEt | |
| 4.71 | CH=CClCOOH | |
| 4.72 | CH=CClCOOCH₃ | |
| 4.73 | COOEt | |
| 4.74 | CONH₂ | |
| 4.75 | —C(O)O—CH₂-(oxiranyl) | |
| 4.76 | CONHSO₂CH₃ | |
| 4.77 | COOCH₂COOH | |
| 4.78 | COOCH₂COOCH₃ | |
| 4.79 | COOCH(CH₃)COOH | |
| 4.80 | COOCH(CH₃)COOCH₃ | |
| 4.81 | COOCH(CH₃)CH₂COOH | |
| 4.82 | COOCH(CH₃)CH₂COOCH₃ | |
| 4.83 | COOC(CH₃)₂CN | |
| 4.84 | COOCH₂CH₂OCH₃ | |
| 4.85 | COOC(CH₃)₂COOCH₂CH₂OCH₃ | |
| 4.86 | COOC(CH₃)₂—C(O)O—CH₂-(oxiranyl) | |
| 4.87 | COOC(CH₃)₂COOCH₂PHENYL | |
| 4.88 | COOCH₂C≡CH | |
| 4.89 | COOC(CH₃)₂COOCH₂C≡CH | |
| 4.90 | COOCH(CH₃)C≡CH | |
| 4.91 | COOC(CH₃)₂COCH₃ | |
| 4.92 | NHallyl | |
| 4.93 | N(COCH₃)allyl | |
| 4.94 | N(Et)SO₂CH₃ | |
| 4.95 | N(allyl)SO₂CH₃ | |
| 4.96 | N(allyl)SO₂Et | |
| 4.97 | SO₂N(CH₃)₂ | |
| 4.98 | SO₂NH₂ | |
| 4.99 | SO₂NHCOCH₃ | |
| 4.100 | OH | |
| 4.101 | OEt | |
| 4.102 | Oallyl | |
| 4.103 | OCH₂C≡CCH₃ | |
| 4.104 | OCH(CH₃)CH=CH₂ | |
| 4.105 | OCH₂CH₂OCH₂CH₃ | |
| 4.106 | OCH₂CH₂OCH₂CH₂OCH₃ | |
| 4.107 | OCH₂-(oxiranyl) | |
| 4.108 | OCH₂CH₂NHCH₃ | |
| 4.109 | OCH₂CH₂N(CH₃)COCH₃ | |
| 4.110 | OCH₂CH₂COOH | |
| 4.111 | OC(CH₃)₂COOH | |
| 4.112 | OC(CH₃)₂COOCH₃ | |
| 4.113 | OC(CH₃)₂COOEt | |
| 4.114 | OCH₂COOH | |
| 4.115 | OSO₂CH₃ | |
| 4.116 | OSO₂CF₃ | |
| 4.117 | CH₂CHClCOOC₂H₅ | |
| 4.118 | CH₂CHClCON(C₂H₅)₂ | |
| 4.119 | CH₂CHClCONHOH | |
| 4.120 | CH₂CHClCOOCH₂C₆H₅ | |
| 4.121 | CH₂CH(CH₃)COOH | |
| 4.122 | CH₂CH(CH₃)COOC₂H₅ | |
| 4.123 | —COOCH₂-(cyclopropyl) | |
| 4.124 | COOC(CH₃)₂COOCH₂CH₂OC₂H₅ | |
| 4.125 | —COOC(CH₃)₂COOCH₂-(cyclopropyl) | |
| 4.126 | COOC(CH₃)₂CONHCH₂C≡CH | |
| 4.127 | COOC(CH₃)₂CON(CH₂CH₃)₂ | |
| 4.128 | OCH₂-(cyclopropyl) | |

TABLE 5

Compounds of formula Ie (Ie) structure: 3-(4-chloro-3-R₆-phenyl)-4-methyl-5-(SOCH₃)-1-methyl-pyrazole

| Comp. No. | R₆ | M.p. |
|---|---|---|
| 5.1 | H | 120–121 |
| 5.2 | NH₂ | 136–139 |
| 5.3 | NO₂ | 151–153 |
| 5.4 | Br | |
| 5.5 | I | 83–86 |
| 5.6 | CN | |
| 5.7 | OCH₃ | |
| 5.8 | N(SO₂CH₃)₂ | |
| 5.9 | NHSO₂CH₃ | |
| 5.10 | OC₃H₇(iso) | |
| 5.11 | O-propargyl | |
| 5.12 | OCH(CH₃)C≡CH | |
| 5.13 | OCH₂COOCH₂CH₃ | |
| 5.14 | OCH₂CH₂OCH₃ | |
| 5.15 | OCH₂CH₂SCH₂CH₃ | |
| 5.16 | OCH₂COOCH₃ | |
| 5.17 | OCH₂COOC₅H₁₁(n) | |
| 5.18 | OCH₂COO-benzyl | |
| 5.19 | OCH(CH₃)COObenzyl (S) | |

TABLE 5-continued

Compounds of formula Ie

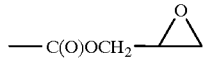

(Ie)

| Comp. No. | R6 | M.p. |
|---|---|---|
| 5.20 | OCH(CH3)COObenzyl (R) | |
| 5.21 | OCH(CH3)COObenzyl (R,S) | |
| 5.22 | SC3H7(iso) | |
| 5.23 | SH | |
| 5.24 | SCH2COOCH3 | |
| 5.25 | SCH2COOC2H5 | |
| 5.26 | SCH(CH3)COObenzyl (S) | |
| 5.27 | SCH(CH3)COObenzyl (R) | |
| 5.28 | SCH(CH3)COObenzyl (R,S) | |
| 5.29 | SCH2COObenzyl | |
| 5.30 | SO2Cl | |
| 5.31 | SO2CH3 | |
| 5.32 | SO2NHCH3 | |
| 5.33 | COOH | 161–165 |
| 5.34 | COOCH3 | 95–97 |
| 5.35 | COOC3H7(iso) | 117–120 |
| 5.36 | COOC(CH3)2COOH | |
| 5.37 | COOC(CH3)2COO-allyl | |
| 5.38 | COOC(CH3)2COOCH3 | |
| 5.39 | COOC(CH3)2COOethyl | oil |
| 5.40 | COOC(CH3)2CONH-allyl | |
| 5.41 | CH2CHClCOOethyl | |
| 5.42 | CH2CH=CH2 | |
| 5.43 | CH2CH2CH3 | |
| 5.44 | CH2CH2CF3 | |
| 5.45 | OCH(CH3)COOC2H5(R) | |
| 5.46 | OCH(CH3)COOC2H5(S) | |
| 5.47 | OCH(CH3)COOC2H5(R,S) | |
| 5.48 | CH2CHClCOOH | |
| 5.49 | CH2CHClCOOCH3 | |
| 5.50 | CH2CHClCOOC3H7(iso) | |
| 5.51 | CH2CHClCONHallyl | |
| 5.52 | CH2C(CH3)ClCOOH | |
| 5.53 | CH2C(CH3)ClCOOCH3 | |
| 5.54 | CH2C(CH3)ClCOOEt | |
| 5.55 | CH2C(CH3)ClCONHEt | |
| 5.56 | CH2CH2COOH | |
| 5.57 | CH2CH2COOCH3 | |
| 5.58 | CH2CH2COOEt | |
| 5.59 | CHClCHClCOOH | |
| 5.60 | CHClCHClCOOCH3 | |
| 5.61 | CHClCHClCOOEt | |
| 5.62 | CH2CH(OCH3)COOH | |
| 5.63 | CH2CH(OCH3)COOCH3 | |
| 5.64 | CH2CH(OCH3)COOEt | |
| 5.65 | CH2CH(SCH3)COOH | |
| 5.66 | CH2CH(SCH3)COOCH3 | |
| 5.67 | CH2CH(SCH3)COOEt | |
| 5.68 | CH=CHCOOH | |
| 5.69 | CH=CHCOOCH3 | |
| 5.70 | CH=CHCOOEt | |
| 5.71 | CH=CClCOOH | |
| 5.72 | CH=CClCOOCH3 | |
| 5.73 | COOEt | |
| 5.74 | CONH2 | |
| 5.75 | —C(O)OCH2—(epoxide) | |
| 5.76 | CONHSO2CH3 | |
| 5.77 | COOCH2COOH | |
| 5.78 | COOCH2COOCH3 | |
| 5.79 | COOCH(CH3)COOH | |
| 5.80 | COOCH(CH3)COOCH3 | |
| 5.81 | COOCH(CH3)CH2COOH | |
| 5.82 | COOCH(CH3)CH2COOCH3 | |
| 5.83 | COOC(CH3)2CN | |
| 5.84 | COOCH2CH2OCH3 | |
| 5.85 | COOC(CH3)2COOCH2CH2OCH3 | |
| 5.86 | COOC(CH3)2—C(O)O—CH2—(epoxide) | |
| 5.87 | COOC(CH3)2COOCH2PHENYL | |
| 5.88 | COOCH2C≡CH | |
| 5.89 | COOC(CH3)2COOCH2C≡CH | |
| 5.90 | COOCH(CH3)C≡CH | |
| 5.91 | COOC(CH3)2COCH3 | |
| 5.92 | NHallyl | |
| 5.93 | N(COCH3)allyl | |
| 5.94 | N(Et)SO2CH3 | |
| 5.95 | N(allyl)SO2CH3 | |
| 5.96 | N(allyl)SO2Et | |
| 5.97 | SO2N(CH3)2 | |
| 5.98 | SO2NH2 | |
| 5.99 | SO2NHCOCH3 | |
| 5.100 | OH | |
| 5.101 | OEt | |
| 5.102 | Oallyl | |
| 5.103 | OCH2C≡CCH3 | |
| 5.104 | OCH(CH3)CH=CH2 | |
| 5.105 | OCH2CH2OCH2CH3 | |
| 5.106 | OCH2CH2OCH2CH2OCH3 | |
| 5.107 | OCH2—(epoxide) | |
| 5.108 | OCH2CH2NHCH3 | |
| 5.109 | OCH2CH2N(CH3)COCH3 | |
| 5.110 | OCH2CH2COOH | |
| 5.111 | OC(CH3)2COOH | |
| 5.112 | OC(CH3)2COOCH3 | |
| 5.113 | OC(CH3)2COOEt | |
| 5.114 | OCH2COOH | |
| 5.115 | OSO2CH3 | |
| 5.116 | OSO2CF3 | |
| 5.117 | CH2CHClCOOC2H5 | |
| 5.118 | CH2CHClCON(C2H5)2 | |
| 5.119 | CH2CHClCONHOH | |
| 5.120 | CH2CHClCOOCH2C6H5 | |
| 5.121 | CH2CH(CH3)COOH | |
| 5.122 | CH2CH(CH3)COOC2H5 | |
| 5.123 | —COOCH2—(cyclopropyl) | |
| 5.124 | COOC(CH3)2COOCH2CH2OC2H5 | |
| 5.125 | —COOC(CH3)2COOCH2—(cyclopropyl) | |
| 5.126 | COOC(CH3)2CONHCH2C≡CH | |
| 5.127 | COOC(CH3)2CON(CH2CH3)2 | |

TABLE 5-continued

Compounds of formula Ie (Ie)

| Comp. No. | R₆ | M.p. |
|---|---|---|
| 5.128 | OCH₂—△ | |

TABLE 6

Compounds of formula If (If)

| Comp. No. | R₆ | M.p. |
|---|---|---|
| 6.1 | H | 122–124 |
| 6.2 | NH₂ | 140–144 |
| 6.3 | NO₂ | 175–176 |
| 6.4 | Br | |
| 6.5 | I | 155–159 |
| 6.6 | CN | |
| 6.7 | OCH₃ | |
| 6.8 | N(SO₂CH₃)₂ | |
| 6.9 | NHSO₂CH₃ | |
| 6.10 | OC₃H₇(iso) | |
| 6.11 | O-propargyl | |
| 6.12 | OCH(CH₃)C≡CH | |
| 6.13 | OCH₂COOCH₂CH₃ | |
| 6.14 | OCH₂CH₂OCH₃ | |
| 6.15 | OCH₂CH₂SCH₂CH₃ | |
| 6.16 | OCH₂COOCH₃ | |
| 6.17 | OCH₂COOC₅H₁₁(n) | |
| 6.18 | OCH₂COO-benzyl | |
| 6.19 | OCH(CH₃)COObenzyl (S) | |
| 6.20 | OCH(CH₃)COObenzyl (R) | |
| 6.21 | OCH(CH₃)COObenzyl (R,S) | |
| 6.22 | SC₃H₇(iso) | |
| 6.23 | SH | |
| 6.24 | SCH₂COOCH₃ | |
| 6.25 | SCH₂COOC₂H₅ | |
| 6.26 | SCH(CH₃)COObenzyl (S) | |
| 6.27 | SCH(CH₃)COObenzyl (R) | |
| 6.28 | SCH(CH₃)COObenzyl (R,S) | |
| 6.29 | SCH₂COObenzyl | |
| 6.30 | SO₂Cl | |
| 6.31 | SO₂CH₃ | |
| 6.32 | SO₂NHCH₃ | |
| 6.33 | COOH | 225–227 |
| 6.34 | COOCH₃ | 104–106 |
| 6.35 | COOC₃H₇(iso) | 98–99 |
| 6.36 | COOC(CH₃)₂COOH | 173–177 |
| 6.37 | COOC(CH₃)₂COO-allyl | |
| 6.38 | COOC(CH₃)₂COOCH₃ | |
| 6.39 | COOC(CH₃)₂COOethyl | 90–92 |
| 6.40 | COOC(CH₃)₂CONH-allyl | |
| 6.41 | CH₂CHClCOOethyl | |
| 6.42 | CH₂CH=CH₂ | |
| 6.43 | CH₂CH₂CH₃ | |
| 6.44 | CH₂CH₂CF₃ | |
| 6.45 | OCH(CH₃)COOC₂H₅(R) | |
| 6.46 | OCH(CH₃)COOC₂H₅(S) | |
| 6.47 | OCH(CH₃)COOC₂H₅(R,S) | |
| 6.48 | CH₂CHClCOOH | |
| 6.49 | CH₂CHClCOOCH₃ | |
| 6.50 | CH₂CHClCOOC₃H₇(iso) | |
| 6.51 | CH₂CHClCONHallyl | |
| 6.52 | CH₂C(CH₃)ClCOOH | |
| 6.53 | CH₂C(CH₃)ClCOOCH₃ | |
| 6.54 | CH₂C(CH₃)ClCOOEt | |
| 6.55 | CH₂C(CH₃)ClCONHEt | |
| 6.56 | CH₂CH₂COOH | |
| 6.57 | CH₂CH₂COOCH₃ | |
| 6.58 | CH₂CH₂COOEt | |
| 6.59 | CHClCHClCOOH | |
| 6.60 | CHClCHClCOOCH₃ | |
| 6.61 | CHClCHClCOOEt | |
| 6.62 | CH₂CH(OCH₃)COOH | |
| 6.63 | CH₂CH(OCH₃)COOCH₃ | |
| 6.64 | CH₂CH(OCH₃)COOEt | |
| 6.65 | CH₂CH(SCH₃)COOH | |
| 6.66 | CH₂CH(SCH₃)COOCH₃ | |
| 6.67 | CH₂CH(SCH₃)COOEt | |
| 6.68 | CH=CHCOOH | |
| 6.69 | CH=CHCOOCH₃ | |
| 6.70 | CH=CHCOOEt | |
| 6.71 | CH=CClCOOH | |
| 6.72 | CH=CClCOOCH₃ | |
| 6.73 | COOEt | |
| 6.74 | CONH₂ | |
| 6.75 | —C(O)OCH₂—△O | |
| 6.76 | CONHSO₂CH₃ | |
| 6.77 | COOCH₂COOH | |
| 6.78 | COOCH₂COOCH₃ | |
| 6.79 | COOCH(CH₃)COOH | |
| 6.80 | COOCH(CH₃)COOCH₃ | |
| 6.81 | COOCH(CH₃)CH₂COOH | |
| 6.82 | COOCH(CH₃)CH₂COOCH₃ | |
| 6.83 | COOC(CH₃)₂CN | |
| 6.84 | COOCH₂CH₂OCH₃ | |
| 6.85 | COOC(CH₃)₂COOCH₂CH₂OCH₃ | |
| 6.86 | COOC(CH₃)₂—C(O)O—CH₂—△O | |
| 6.87 | COOC(CH₃)₂COOCH₂PHENYL | |
| 6.88 | COOCH₂C≡CH | |
| 6.89 | COOC(CH₃)₂COOCH₂C≡CH | |
| 6.90 | COOCH(CH₃)C≡CH | |
| 6.91 | COOC(CH₃)₂COCH₃ | |
| 6.92 | NHallyl | |
| 6.93 | N(COCH₃)allyl | |
| 6.94 | N(Et)SO₂CH₃ | |
| 6.95 | N(allyl)SO₂CH₃ | |
| 6.96 | N(allyl)SO₂Et | |

TABLE 6-continued

Compounds of formula If (If)

| Comp. No. | R$_6$ | M.p. |
|---|---|---|
| 6.97 | SO$_2$N(CH$_3$)$_2$ | |
| 6.98 | SO$_2$NH$_2$ | |
| 6.99 | SO$_2$NHCOCH$_3$ | |
| 6.100 | OH | |
| 6.101 | OEt | |
| 6.102 | Oallyl | |
| 6.103 | OCH$_2$C≡CCH$_3$ | |
| 6.104 | OCH(CH$_3$)CH=CH$_2$ | |
| 6.105 | OCH$_2$CH$_2$OCH$_2$CH$_3$ | |
| 6.106 | OCH$_2$CH$_2$OCH$_2$CH$_2$OCH$_3$ | |
| 6.107 | OCH$_2$-(epoxide) | |
| 6.108 | OCH$_2$CH$_2$NHCH$_3$ | |
| 6.109 | OCH$_2$CH$_2$N(CH$_3$)COCH$_3$ | |
| 6.110 | OCH$_2$CH$_2$COOH | |
| 6.111 | OC(CH$_3$)$_2$COOH | |
| 6.112 | OC(CH$_3$)$_2$COOCH$_3$ | |
| 6.113 | OC(CH$_3$)$_2$COOEt | |
| 6.114 | OCH$_2$COOH | |
| 6.115 | OSO$_2$CH$_3$ | |
| 6.116 | OSO$_2$CF$_3$ | |
| 6.117 | CH$_2$CHClCOOC$_2$H$_5$ | |
| 6.118 | CH$_2$CHClCON(C$_2$H$_5$)$_2$ | |
| 6.119 | CH$_2$CHClCONHOH | |
| 6.120 | CH$_2$CHClCOOCH$_2$C$_6$H$_5$ | |
| 6.121 | CH$_2$CH(CH$_3$)COOH | |
| 6.122 | CH$_2$CH(CH$_3$)COOC$_2$H$_5$ | |
| 6.123 | —COOCH$_2$-cyclopropyl | |
| 6.124 | COOC(CH$_3$)$_2$COOCH$_2$CH$_2$OC$_2$H$_5$ | |
| 6.125 | —COOC(CH$_3$)$_2$COOCH$_2$-cyclopropyl | |
| 6.126 | COOC(CH$_3$)$_2$CONHCH$_2$C≡CH | |
| 6.127 | COOC(CH$_3$)$_2$CON(CH$_2$CH$_3$)$_2$ | |
| 6.128 | OCH$_2$-cyclopropyl | |

TABLE 7

Compounds of formula Ig (Ig)

| Comp. No. | R$_6$ | M.p. |
|---|---|---|
| 7.1 | H | oil |
| 7.2 | NO$_2$ | |
| 7.3 | Br | |
| 7.4 | I | 88–90 |
| 7.5 | CN | |
| 7.6 | OCH$_3$ | 88–90 |
| 7.7 | N(SO$_2$CH$_3$)$_2$ | 196–198 |
| 7.8 | NHSO$_2$CH$_3$ | 120–122 |
| 7.9 | OC$_3$H$_7$(iso) | |
| 7.10 | O-propargyl | 88–89 |
| 7.11 | OCH(CH$_3$)C≡CH | |
| 7.12 | O-phenyl | |
| 7.13 | O-2-pyridyl | |
| 7.14 | O-2-pyrimidinyl | |
| 7.15 | OCH$_2$COOC$_2$H$_5$ | 115–116 |
| 7.16 | OCH$_2$COOC$_5$H$_{11}$(n) | 74–76 |
| 7.17 | OCH$_2$COO-benzyl | |
| 7.18 | OCH(CH$_3$)COObenzyl (S) | |
| 7.19 | OCH(CH$_3$)COObenzyl (R) | |
| 7.20 | OCH(CH$_3$)COObenzyl (R,S) | |
| 7.21 | SC$_3$H$_7$(iso) | oil |
| 7.22 | SH | 78–80 |
| 7.23 | SCH$_2$COOCH$_3$ | |
| 7.24 | SCH$_2$COOC$_2$H$_5$ | 106–108 |
| 7.25 | SCH(CH$_3$)COObenzyl (S) | |
| 7.26 | SCH(CH$_3$)COObenzyl (R) | |
| 7.27 | SCH(CH$_3$)COObenzyl (R,S) | |
| 7.28 | SCH$_2$COObenzyl | |
| 7.29 | SO$_2$Cl | 121–123 |
| 7.30 | SO$_2$CH$_3$ | |
| 7.31 | SO$_2$NHCH$_3$ | 152–153 |
| 7.32 | COOH | 210–217 |
| 7.33 | COOCH$_3$ | 92–93 |
| 7.34 | COOC$_3$H$_7$(iso) | oil |
| 7.35 | COOC(CH$_3$)$_2$COOH | 157–162 |
| 7.36 | COOC(CH$_3$)$_2$COO-allyl | |
| 7.37 | COOC(CH$_3$)$_2$COOCH$_3$ | |
| 7.38 | COOC(CH$_3$)$_2$COOethyl | 79.5–81.5 |
| 7.39 | COOC(CH$_3$)$_2$CONH-allyl | resin |
| 7.40 | CH$_2$CHClCOOethyl | oil |
| 7.41 | CH$_2$CH=CH$_2$ | oil |
| 7.42 | CH$_2$CH$_2$CH$_3$ | oil |
| 7.43 | CH$_2$CH$_2$CF$_3$ | 74–76 |
| 7.44 | OCH(CH$_3$)COOC$_2$H$_5$(R) | |
| 7.45 | OCH(CH$_3$)COOC$_2$H$_5$(S) | |
| 7.46 | OCH(CH$_3$)COOC$_2$H$_5$(R,S) | |
| 7.47 | CH$_2$CHClCOOH | 98–99 |
| 7.48 | CH$_2$CHClCOOCH$_3$ | oil |
| 7.49 | CH$_2$CHClCOOC$_3$H$_7$(iso) | |
| 7.50 | CH$_2$CHClCONHallyl | |
| 7.51 | CH$_2$C(CH$_3$)ClCOOH | |
| 7.52 | CH$_2$C(CH$_3$)ClCOOCH$_3$ | oil |
| 7.53 | CH$_2$C(CH$_3$)ClCOOEt | |
| 7.54 | CH$_2$C(CH$_3$)ClCONHEt | |
| 7.55 | CH$_2$CH$_2$COOH | |
| 7.56 | CH$_2$CH$_2$COOCH$_3$ | 110–111 |
| 7.57 | CH$_2$CH$_2$COOEt | |
| 7.58 | CHClCHClCOOH | |
| 7.59 | CHClCHClCOOCH$_3$ | |
| 7.60 | CHClCHClCOOEt | |
| 7.61 | CH$_2$CH(OCH$_3$)COOH | |
| 7.62 | CH$_2$CH(OCH$_3$)COOCH$_3$ | |
| 7.63 | CH$_2$CH(OCH$_3$)COOEt | |
| 7.64 | CH$_2$CH(SCH$_3$)COOH | |

TABLE 7-continued

Compounds of formula Ig (Ig)

| Comp. No. | R$_6$ | M.p. |
|---|---|---|
| 7.65 | CH$_2$CH(SCH$_3$)COOCH$_3$ | |
| 7.66 | CH$_2$CH(SCH$_3$)COOEt | |
| 7.67 | CH=CHCOOH | |
| 7.68 | CH=CHCOOCH$_3$ | 148–149 |
| 7.69 | CH=CHCOOEt | |
| 7.70 | CH=CClCOOH | |
| 7.71 | CH=CClCOOCH$_3$ | |
| 7.72 | COOEt | |
| 7.73 | CONH$_2$ | |
| 7.74 | —C(O)OCH$_2$—(oxiranyl) | |
| 7.75 | CONHSO$_2$CH$_3$ | |
| 7.76 | COOCH$_2$COOH | |
| 7.77 | COOCH$_2$COOCH$_3$ | |
| 7.78 | COOCH(CH$_3$)COOH | |
| 7.79 | COOCH(CH$_3$)COOCH$_3$ | |
| 7.80 | COOCH(CH$_3$)CH$_2$COOH | |
| 7.81 | COOCH(CH$_3$)CH$_2$COOCH$_3$ | |
| 7.82 | COOC(CH$_3$)$_2$CN | |
| 7.83 | COOCH$_2$CH$_2$OCH$_3$ | |
| 7.84 | COOC(CH$_3$)$_2$COOCH$_2$CH$_2$OCH$_3$ | |
| 7.85 | COOC(CH$_3$)$_2$—C(O)O—CH$_2$—(oxiranyl) | |
| 7.86 | COOC(CH$_3$)$_2$COOCH$_2$PHENYL | oil |
| 7.87 | COOCH$_2$C≡CH | |
| 7.88 | COOC(CH$_3$)$_2$COOCH$_2$C≡CH | |
| 7.89 | COOCH(CH$_3$)C≡CH | |
| 7.90 | COOC(CH$_3$)$_2$COCH$_3$ | |
| 7.91 | NHallyl | |
| 7.92 | N(COCH$_3$)allyl | |
| 7.93 | N(Et)SO$_2$CH$_3$ | |
| 7.94 | N(allyl)SO$_2$CH$_3$ | |
| 7.95 | N(allyl)SO$_2$Et | |
| 7.96 | SO$_2$N(CH$_3$)$_2$ | oil |
| 7.97 | SO$_2$NH$_2$ | 181–182 |
| 7.98 | SO$_2$NHCOCH$_3$ | |
| 7.99 | OH | 164–166 |
| 7.100 | OEt | |
| 7.101 | Oallyl | |
| 7.102 | OCH$_2$C≡CCH$_3$ | |
| 7.103 | OCH(CH$_3$)CH=CH$_2$ | |
| 7.104 | OCH$_2$CH$_2$OCH$_2$CH$_3$ | |
| 7.105 | OCH$_2$CH$_2$OCH$_2$CH$_2$OCH$_3$ | |
| 7.106 | OCH$_2$—(oxiranyl) | |
| 7.107 | OCH$_2$CH$_2$NHCH$_3$ | |
| 7.108 | OCH$_2$CH$_2$N(CH$_3$)COCH$_3$ | |
| 7.109 | OCH$_2$CH$_2$COOH | |
| 7.110 | OC(CH$_3$)$_2$COOH | |
| 7.111 | OC(CH$_3$)$_2$COOCH$_3$ | |
| 7.112 | OC(CH$_3$)$_2$COOEt | |
| 7.113 | OCH$_2$COOH | |
| 7.114 | OSO$_2$CH$_3$ | |
| 7.115 | OSO$_2$CF$_3$ | |
| 7.116 | Cl | 58–60 |
| 7.117 | CH$_2$CHClCOOC$_2$H$_5$ | |
| 7.118 | CH$_2$CHClCON(C$_2$H$_5$)$_2$ | |
| 7.119 | CH$_2$CHClCONHOH | |
| 7.120 | CH$_2$CHClCOOCH$_2$C$_6$H$_5$ | |
| 7.121 | CH$_2$CH(CH$_3$)COOH | |
| 7.122 | CH$_2$CH(CH$_3$)COOC$_2$H$_5$ | |
| 7.123 | —COOCH$_2$—(cyclopropyl) | |
| 7.124 | COOC(CH$_3$)$_2$COOCH$_2$CH$_2$OC$_2$H$_5$ | |
| 7.125 | —COOC(CH$_3$)$_2$COOCH$_2$—(cyclopropyl) | |
| 7.126 | COOC(CH$_3$)$_2$CONHCH$_2$C≡CH | |
| 7.127 | COOC(CH$_3$)$_2$CON(CH$_2$CH$_3$)$_2$ | |
| 7.128 | OCH$_2$—(cyclopropyl) | |
| 7.129 | CH=CH—CF$_3$ | 102—103 |

TABLE 8

Compounds of formula Ih (Ih)

| Comp. No. | R$_6$ | M.p. |
|---|---|---|
| 8.1 | H | 98–100 |
| 8.2 | NH$_2$ | 164–165 |
| 8.3 | NO$_2$ | 164–165 |
| 8.4 | Br | |
| 8.5 | I | |
| 8.6 | CN | |
| 8.7 | OCH$_3$ | 152–153 |
| 8.8 | N(SO$_2$CH$_3$)$_2$ | 246–248 |
| 8.9 | NHSO$_2$CH$_3$ | 153–154 |
| 8.10 | OC$_3$H$_7$(iso) | |
| 8.11 | O-propargyl | 151–152 |
| 8.12 | OCH(CH$_3$)C≡CH | |
| 8.13 | O-phenyl | |
| 8.14 | O-2-pyridyl | |
| 8.15 | O-2-pyrimidinyl | |
| 8.16 | OCH$_2$COOC$_2$H$_5$ | 165–166 |
| 8.17 | OCH$_2$COOC$_5$H$_{11}$(n) | 89–91 |
| 8.18 | OCH$_2$COO-benzyl | |

TABLE 8-continued

Compounds of formula Ih

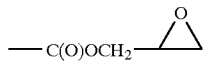

(Ih)

| Comp. No. | R6 | M.p. |
|---|---|---|
| 8.19 | OCH(CH₃)COObenzyl (S) | |
| 8.20 | OCH(CH₃)COObenzyl (R) | |
| 8.21 | OCH(CH₃)COObenzyl (R,S) | |
| 8.22 | SC₃H₇(iso) | |
| 8.23 | SH | |
| 8.24 | SCH₂COOCH₃ | |
| 8.25 | SCH₂COOC₂H₅ | |
| 8.26 | SCH(CH₃)COObenzyl (S) | |
| 8.27 | SCH(CH₃)COObenzyl (R) | |
| 8.28 | SCH(CH₃)COObenzyl (R,S) | |
| 8.29 | SCH₂COObenzyl | |
| 8.30 | SO₂Cl | 160–163 |
| 8.31 | SO₂CH₃ | |
| 8.32 | SO₂NHCH₃ | |
| 8.33 | COOH | 78–86 |
| 8.34 | COOCH₃ | 134–136 |
| 8.35 | COOC₃H₇(iso) | 116–119 |
| 8.36 | COOC(CH₃)₂COOH | 78–86 |
| 8.37 | COOC(CH₃)₂COO-allyl | |
| 8.38 | COOC(CH₃)₂COOCH₃ | |
| 8.39 | COOC(CH₃)₂COOethyl | oil |
| 8.40 | COOC(CH₃)₂CONH-allyl | 168–172 |
| 8.41 | CH₂CHClCOOethyl | 87–89 |
| 8.42 | CH₂CH=CH₂ | 118–120 |
| 8.43 | CH₂CH₂CH₃ | 128–129 |
| 8.44 | CH₂CH₂CF₃ | |
| 8.45 | OCH(CH₃)COOC₂H₅(R) | |
| 8.46 | OCH(CH₃)COOC₂H₅(S) | |
| 8.47 | OCH(CH₃)COOC₂H₅(R,S) | |
| 8.48 | CH₂CHClCOOH | 92–94 |
| 8.49 | CH₂CHClCOOCH₃ | 95–96 |
| 8.50 | CH₂CHClCOOC₃H₇(iso) | |
| 8.51 | CH₂CHClCONHallyl | |
| 8.52 | CH₂C(CH₃)ClCOOH | |
| 8.53 | CH₂C(CH₃)ClCOOCH₃ | oil |
| 8.54 | CH₂C(CH₃)ClCOOEt | |
| 8.55 | CH₂C(CH₃)ClCONHEt | |
| 8.56 | CH₂CH₂COOH | |
| 8.57 | CH₂CH₂COOCH₃ | 153–154 |
| 8.58 | CH₂CH₂COOEt | |
| 8.59 | CHClCHClCOOH | |
| 8.60 | CHClCHClCOOCH₃ | |
| 8.61 | CHClCHClCOOEt | |
| 8.62 | CH₂CH(OCH₃)COOH | |
| 8.63 | CH₂CH(OCH₃)COOCH₃ | |
| 8.64 | CH₂CH(OCH₃)COOEt | |
| 8.65 | CH₂CH(SCH₃)COOH | |
| 8.66 | CH₂CH(SCH₃)COOCH₃ | |
| 8.67 | CH₂CH(SCH₃)COOEt | |
| 8.68 | CH=CHCOOH | |
| 8.69 | CH=CHCOOCH₃ | |
| 8.70 | CH=CHCOOEt | |
| 8.71 | CH=CClCOOH | |
| 8.72 | CH=CClCOOCH₃ | |
| 8.73 | COOEt | 122–123 |
| 8.74 | CONH₂ | |
| 8.75 | —C(O)OCH₂—(epoxide) | |
| 8.76 | CONHSO₂CH₃ | |
| 8.77 | COOCH₂COOH | |
| 8.78 | COOCH₂COOCH₃ | |
| 8.79 | COOCH(CH₃)COOH | |
| 8.80 | COOCH(CH₃)COOCH₃ | |
| 8.81 | COOCH(CH₃)CH₂COOH | |
| 8.82 | COOCH(CH₃)CH₂COOCH₃ | |
| 8.83 | COOC(CH₃)₂CN | |
| 8.84 | COOCH₂CH₂OCH₃ | |
| 8.85 | COOC(CH₃)₂COOCH₂CH₂OCH₃ | |
| 8.86 | COOC(CH₃)₂—C(O)O—CH₂—(epoxide) | |
| 8.87 | COOC(CH₃)₂COOCH₂PHENYL | oil |
| 8.88 | COOCH₂C≡CH | |
| 8.89 | COOC(CH₃)₂COOCH₂C≡CH | |
| 8.90 | COOCH(CH₃)C≡CH | |
| 8.91 | COOC(CH₃)₂COCH₃ | |
| 8.92 | NHallyl | |
| 8.93 | N(COCH₃)allyl | |
| 8.94 | N(Et)SO₂CH₃ | |
| 8.95 | N(allyl)SO₂CH₃ | |
| 8.96 | N(allyl)SO₂Et | |
| 8.97 | SO₂N(CH₃)₂ | |
| 8.98 | SO₂NH₂ | |
| 8.99 | SO₂NHCOCH₃ | |
| 8.100 | OH | |
| 8.101 | OEt | |
| 8.102 | Oallyl | |
| 8.103 | OCH₂C≡CCH₃ | |
| 8.104 | OCH(CH₃)CH=CH₂ | |
| 8.105 | OCH₂CH₂OCH₂CH₃ | |
| 8.106 | OCH₂CH₂OCH₂CH₂OCH₃ | |
| 8.107 | OCH₂—(epoxide) | |
| 8.108 | OCH₂CH₂NHCH₃ | |
| 8.109 | OCH₂CH₂N(CH₃)COCH₃ | |
| 8.110 | OCH₂CH₂COOH | |
| 8.111 | OC(CH₃)₂COOH | |
| 8.112 | OC(CH₃)₂COOCH₃ | |
| 8.113 | OC(CH₃)₂COOEt | |
| 8.114 | OCH₂COOH | |
| 8.115 | OSO₂CH₃ | |
| 8.116 | OSO₂CF₃ | |
| 8.117 | CH₂CHClCOOC₂H₅ | |
| 8.118 | CH₂CHClCON(C₂H₅)₂ | |
| 8.119 | CH₂CHClCONHOH | |
| 8.120 | CH₂CHClCOOCH₂C₆H₅ | |
| 8.121 | CH₂CH(CH₃)COOH | |
| 8.122 | CH₂CH(CH₃)COOC₂H₅ | |
| 8.123 | —COOCH₂—(cyclopropyl) | |
| 8.124 | COOC(CH₃)₂COOCH₂CH₂OC₂H₅ | |
| 8.125 | —COOC(CH₃)₂COOCH₂—(cyclopropyl) | |

TABLE 8-continued

Compounds of formula Ih

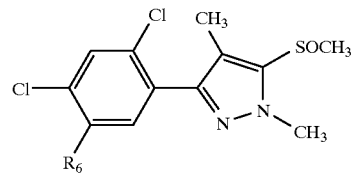

(Ih)

| Comp. No. | R$_6$ | M.p. |
|---|---|---|
| 8.126 | COOC(CH$_3$)$_2$CONHCH$_2$C≡CH | |
| 8.127 | COOC(CH$_3$)$_2$CON(CH$_2$CH$_3$)$_2$ | |
| 8.128 | —OCH$_2$—◁ | |
| 8.129 | CH═CH—CF$_3$ | |

TABLE 9

Compounds of formula Ii

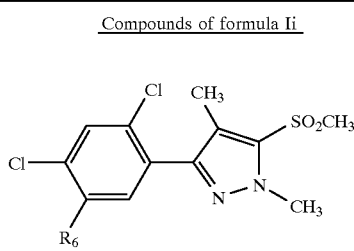

(Ii)

| Comp. No. | R$_6$ | M.p. |
|---|---|---|
| 9.1 | H | 110–112 |
| 9.2 | NH$_2$ | 185–187 |
| 9.3 | NO$_2$ | 156–159 |
| 9.4 | Br | |
| 9.5 | I | 167–170 |
| 9.6 | CN | |
| 9.7 | OCH$_3$ | 150–151 |
| 9.8 | N(SO$_2$CH$_3$)$_2$ | 265–267 |
| 9.9 | NHSO$_2$CH$_3$ | 185–187 |
| 9.10 | OC$_3$H$_7$(iso) | |
| 9.11 | O-propargyl | 126–127 |
| 9.12 | OCH(CH$_3$)C≡CH | |
| 9.13 | O-phenyl | |
| 9.14 | O-2-pyridyl | |
| 9.15 | O-2-pyrimidinyl | |
| 9.16 | OCH$_2$COOC$_2$H$_5$ | 140–141 |
| 9.17 | OCH$_2$COOC$_5$H$_{11}$(n) | 118–120 |
| 9.18 | OCH$_2$COO-benzyl | |
| 9.19 | OCH(CH$_3$)COObenzyl (S) | |
| 9.20 | OCH(CH$_3$)COObenzyl (R) | |
| 9.21 | OCH(CH$_3$)COObenzyl (R,S) | |
| 9.22 | SC$_3$H$_7$(iso) | 93–95 |
| 9.23 | SH | |
| 9.24 | SCH$_2$COOCH$_3$ | |
| 9.25 | SCH$_2$COOC$_2$H$_5$ | 133–135 |
| 9.26 | SCH(CH$_3$)COObenzyl (S) | |
| 9.27 | SCH(CH$_3$)COObenzyl (R) | |
| 9.28 | SCH(CH$_3$)COObenzyl (R,S) | |
| 9.29 | SCH$_2$COObenzyl | |
| 9.30 | SO$_2$Cl | 169–171 |
| 9.31 | SO$_2$CH$_3$ | |
| 9.32 | SO$_2$NHCH$_3$ | |
| 9.33 | COOH | 201–208 |
| 9.34 | COOCH$_3$ | 137–139 |
| 9.35 | COOC$_3$H$_7$(iso) | 111–114 |
| 9.36 | COOC(CH$_3$)$_2$COOH | 179–182 |

TABLE 9-continued

Compounds of formula Ii

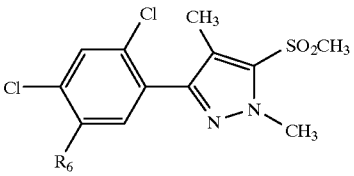

(Ii)

| Comp. No. | R$_6$ | M.p. |
|---|---|---|
| 9.37 | COOC(CH$_3$)$_2$COO-allyl | |
| 9.38 | COOC(CH$_3$)$_2$COOCH$_3$ | |
| 9.39 | COOC(CH$_3$)$_2$COOethyl | oil |
| 9.40 | COOC(CH$_3$)$_2$CONH-allyl | 141–143 |
| 9.41 | CH$_2$CHClCOOethyl | oil |
| 9.42 | CH$_2$CH═CH$_2$ | oil |
| 9.43 | CH$_2$CH$_2$CH$_3$ | 107–109 |
| 9.44 | CH$_2$CH$_2$CF$_3$ | |
| 9.45 | OCH(CH$_3$)COOC$_2$H$_5$(R) | |
| 9.46 | OCH(CH$_3$)COOC$_2$H$_5$(S) | |
| 9.47 | OCH(CH$_3$)COOC$_2$H$_5$(R,S) | |
| 9.48 | CH$_2$CHClCOOH | 185–187 |
| 9.49 | CH$_2$CHClCOOCH$_3$ | 96–98 |
| 9.50 | CH$_2$CHClCOOC$_3$H$_7$(iso) | |
| 9.51 | CH$_2$CHClCONHallyl | |
| 9.52 | CH$_2$C(CH$_3$)ClCOOH | |
| 9.53 | CH$_2$C(CH$_3$)ClCOOCH$_3$ | oil |
| 9.54 | CH$_2$C(CH$_3$)ClCOOEt | |
| 9.55 | CH$_2$C(CH$_3$)ClCONHEt | |
| 9.56 | CH$_2$CH$_2$COOH | |
| 9.57 | CH$_2$CH$_2$COOCH$_3$ | 152–153 |
| 9.58 | CH$_2$CH$_2$COOEt | |
| 9.59 | CHClCHClCOOH | |
| 9.60 | CHClCHClCOOCH$_3$ | |
| 9.61 | CHClCHClCOOEt | |
| 9.62 | CH$_2$CH(OCH$_3$)COOH | |
| 9.63 | CH$_2$CH(OCH$_3$)COOCH$_3$ | |
| 9.64 | CH$_2$CH(OCH$_3$)COOEt | |
| 9.65 | CH$_2$CH(SCH$_3$)COOH | |
| 9.66 | CH$_2$CH(SCH$_3$)COOCH$_3$ | |
| 9.67 | CH$_2$CH(SCH$_3$)COOEt | |
| 9.68 | CH═CHCOOH | |
| 9.69 | CH═CHCOOCH$_3$ | |
| 9.70 | CH═CHCOOEt | |
| 9.71 | CH═CClCOOH | |
| 9.72 | CH═CClCOOCH$_3$ | |
| 9.73 | COOEt | 105–107 |
| 9.74 | CONH$_2$ | |
| 9.75 | —C(O)OCH$_2$—△O | |
| 9.76 | CONHSO$_2$CH$_3$ | |
| 9.77 | COOCH$_2$COOH | |
| 9.78 | COOCH$_2$COOCH$_3$ | |
| 9.79 | COOCH(CH$_3$)COOH | |
| 9.80 | COOCH(CH$_3$)COOCH$_3$ | |
| 9.81 | COOCH(CH$_3$)CH$_2$COOH | |
| 9.82 | COOCH(CH$_3$)CH$_2$COOCH$_3$ | |
| 9.83 | COOC(CH$_3$)$_2$CN | |
| 9.84 | COOCH$_2$CH$_2$OCH$_3$ | |
| 9.85 | COOC(CH$_3$)$_2$COOCH$_2$CH$_2$OCH$_3$ | |
| 9.86 | COOC(CH$_3$)$_2$—C(O)O—CH$_2$—△O | |
| 9.87 | COOC(CH$_3$)$_2$COOCH$_2$PHENYL | |
| 9.88 | COOCH$_2$C≡CH | |
| 9.89 | COOC(CH$_3$)$_2$COOCH$_2$C≡CH | |
| 9.90 | COOCH(CH$_3$)C≡CH | |
| 9.91 | COOC(CH$_3$)$_2$COCH$_3$ | |

TABLE 9-continued

Compounds of formula Ii (Ii) 3-(2,4-dichloro-5-R6-phenyl)-4-methyl-5-methylsulfonyl-1-methylpyrazole

| Comp. No. | R$_6$ | M.p. |
|---|---|---|
| 9.92 | NHallyl | |
| 9.93 | N(COCH$_3$)allyl | |
| 9.94 | N(Et)SO$_2$CH$_3$ | |
| 9.95 | N(allyl)SO$_2$CH$_3$ | |
| 9.96 | N(allyl)SO$_2$Et | |
| 9.97 | SO$_2$N(CH$_3$)$_2$ | |
| 9.98 | SO$_2$NH$_2$ | |
| 9.99 | SO$_2$NHCOCH$_3$ | |
| 9.100 | OH | 164–165 |
| 9.101 | OEt | |
| 9.102 | Oallyl | |
| 9.103 | OCH$_2$C≡CCH$_3$ | |
| 9.104 | OCH(CH$_3$)CH=CH$_2$ | |
| 9.105 | OCH$_2$CH$_2$OCH$_2$CH$_3$ | |
| 9.106 | OCH$_2$CH$_2$OCH$_2$CH$_2$OCH$_3$ | |
| 9.107 | OCH$_2$-(epoxide) | |
| 9.108 | OCH$_2$CH$_2$NHCH$_3$ | |
| 9.109 | OCH$_2$CH$_2$N(CH$_3$)COCH$_3$ | |
| 9.110 | OCH$_2$COOH | |
| 9.111 | OC(CH$_3$)$_2$COOH | |
| 9.112 | OC(CH$_3$)$_2$COOCH$_3$ | |
| 9.113 | OC(CH$_3$)$_2$COOEt | |
| 9.114 | OCH$_2$COOH | |
| 9.115 | OSO$_2$CH$_3$ | |
| 9.116 | OSO$_2$CF$_3$ | |
| 9.117 | CH$_2$CHClCOOC$_2$H$_5$ | |
| 9.118 | CH$_2$CHClCON(C$_2$H$_5$)$_2$ | |
| 9.119 | CH$_2$CHClCONHOH | |
| 9.120 | CH$_2$CHClCOOCH$_2$C$_6$H$_5$ | |
| 9.121 | CH$_2$CH(CH$_3$)COOH | |
| 9.122 | CH$_2$CH(CH$_3$)COOC$_2$H$_5$ | |
| 9.123 | —COOCH$_2$-cyclopropyl | |
| 9.124 | COOC(CH$_3$)$_2$COOCH$_2$CH$_2$OC$_2$H$_5$ | |
| 9.125 | —COOC(CH$_3$)$_2$COOCH$_2$-cyclopropyl | |
| 9.126 | COOC(CH$_3$)$_2$CONHCH$_2$C≡CH | |
| 9.127 | COOC(CH$_3$)$_2$CON(CH$_2$CH$_3$)$_2$ | |
| 9.128 | OCH$_2$-cyclopropyl | |

TABLE 10

Compounds of formula Ij (Ij)

| Comp. No. | R$_6$ | M.p. |
|---|---|---|
| 10.1 | H | 72–74 |
| 10.2 | CN | |
| 10.3 | OCH$_3$ | |
| 10.4 | NHSO$_2$CH$_3$ | |
| 10.5 | OC$_3$H$_7$(iso) | |
| 10.6 | O-propargyl | |
| 10.7 | OCH(CH$_3$)C≡CH | |
| 10.8 | OCH$_2$COOCH$_2$CH$_3$ | |
| 10.9 | OCH$_2$CH$_2$OCH$_3$ | |
| 10.10 | OCH$_2$CH$_2$SCH$_2$CH$_3$ | |
| 10.11 | OCH$_2$COOCH$_3$ | |
| 10.12 | OCH$_2$COOC$_5$H$_{11}$(n) | |
| 10.13 | OCH$_2$COO-benzyl | |
| 10.14 | OCH(CH$_3$)COObenzyl | |
| 10.15 | SC$_3$H$_7$(iso) | |
| 10.16 | SCH$_2$COOCH$_3$ | |
| 10.17 | SCH$_2$COOC$_2$H$_5$ | |
| 10.18 | SCH(CH$_3$)COObenzyl | |
| 10.19 | SCH$_2$COObenzyl | |
| 10.20 | COOCH$_3$ | |
| 10.21 | COOC$_3$H$_7$(iso) | |
| 10.22 | COOC(CH$_3$)$_2$COOH | |
| 10.23 | COOC(CH$_3$)$_2$COO-allyl | |
| 10.24 | COOC(CH$_3$)$_2$COOCH$_3$ | |
| 10.25 | COOC(CH$_3$)$_2$COOethyl | |
| 10.26 | COOC(CH$_3$)$_2$CONH-allyl | |
| 10.27 | CH$_2$CHClCOOethyl | |
| 10.28 | CH$_2$CH=CH$_2$ | |
| 10.29 | CH$_2$CH$_2$CH$_3$ | |
| 10.30 | CH$_2$CH$_2$CF$_3$ | |
| 10.31 | OCH(CH$_3$)COOC$_2$H$_5$(R) | |
| 10.32 | OCH(CH$_3$)COOC$_2$H$_5$(S) | |
| 10.33 | OCH(CH$_3$)COOC$_2$H$_5$(R,S) | |
| 10.34 | CH$_2$CHClCOOH | |
| 10.35 | CH$_2$CHClCOOCH$_3$ | |
| 10.36 | CH$_2$CHClCOOC$_3$H$_7$(iso) | |
| 10.37 | CH$_2$CHClCONHallyl | |
| 10.38 | CH$_2$C(CH$_3$)ClCOOH | |
| 10.39 | CH$_2$C(CH$_3$)ClCOOCH$_3$ | |
| 10.40 | CH$_2$C(CH$_3$)ClCOOEt | |
| 10.41 | CH$_2$C(CH$_3$)ClCONHEt | |
| 10.42 | CH$_2$CH$_2$COOH | |
| 10.43 | CH$_2$CH$_2$COOCH$_3$ | |
| 10.44 | CH$_2$CH$_2$COOEt | |
| 10.45 | CHClCHClCOOH | |
| 10.46 | CHClCHClCOOCH$_3$ | |
| 10.47 | CHClCHClCOOEt | |
| 10.48 | CH$_2$CH(OCH$_3$)COOH | |
| 10.49 | CH$_2$CH(OCH$_3$)COOCH$_3$ | |
| 10.50 | CH$_2$CH(OCH$_3$)COOEt | |
| 10.51 | CH$_2$CH(SCH$_3$)COOH | |
| 10.52 | CH$_2$CH(SCH$_3$)COOCH$_3$ | |
| 10.53 | CH$_2$CH(SCH$_3$)COOEt | |
| 10.54 | CH=CHCOOH | |
| 10.55 | CH=CHCOOCH$_3$ | |
| 10.56 | CH=CHCOOEt | |
| 10.57 | CH=CClCOOH | |
| 10.58 | CH=CClCOOCH$_3$ | |
| 10.59 | COOEt | |
| 10.60 | CONH$_2$ | |
| 10.61 | —C(O)OCH$_2$-(epoxide) | |

TABLE 10-continued

Compounds of formula lj (lj)

[Structure: pyrazole with Cl, CH3, SCH3, CH3, N-CH3, R6 substituents]

| Comp. No. | R6 | M.p. |
|---|---|---|
| 10.62 | CONHSO$_2$CH$_3$ | |
| 10.63 | COOCH$_2$COOH | |
| 10.64 | COOCH$_2$COOCH$_3$ | |
| 10.65 | COOCH(CH$_3$)COOH | |
| 10.66 | COOCH(CH$_3$)COOCH$_3$ | |
| 10.67 | COOCH(CH$_3$)CH$_2$COOH | |
| 10.68 | COOCH(CH$_3$)CH$_2$COOCH$_3$ | |
| 10.69 | COOC(CH$_3$)$_2$CN | |
| 10.70 | COOCH$_2$CH$_2$OCH$_3$ | |
| 10.71 | COOC(CH$_3$)$_2$COOCH$_2$CH$_2$OCH$_3$ | |
| 10.72 | COOC(CH$_3$)$_2$—C(O)O—CH$_2$—[epoxide] | |
| 10.73 | COOC(CH$_3$)$_2$COOCH$_2$PHENYL | |
| 10.74 | COOCH$_2$C≡CH | |
| 10.75 | COOC(CH$_3$)$_2$COOCH$_2$C≡CH | |
| 10.76 | COOCH(CH$_3$)C≡CH | |
| 10.77 | COOC(CH$_3$)$_2$COCH$_3$ | |
| 10.78 | NHallyl | |
| 10.79 | N(COCH$_3$)allyl | |
| 10.80 | N(Et)SO$_2$CH$_3$ | |
| 10.81 | N(allyl)SO$_2$CH$_3$ | |
| 10.82 | N(allyl)SO$_2$Et | |
| 10.83 | SO$_2$N(CH$_3$)$_2$ | |
| 10.84 | SO$_2$NH$_2$ | |
| 10.85 | SO$_2$NHCOCH$_3$ | |
| 10.86 | OH | |
| 10.87 | OEt | |
| 10.88 | Oallyl | |
| 10.89 | OCH$_2$C≡CCH$_3$ | |
| 10.90 | OCH(CH$_3$)CH=CH$_2$ | |
| 10.91 | OCH$_2$CH$_2$OCH$_2$CH$_3$ | |
| 10.92 | OCH$_2$CH$_2$OCH$_2$CH$_2$OCH$_3$ | |
| 10.93 | OCH$_2$—[epoxide] | |
| 10.94 | OCH$_2$CH$_2$NHCH$_3$ | |
| 10.95 | OCH$_2$CH$_2$N(CH$_3$)COCH$_3$ | |
| 10.96 | OCH$_2$CH$_2$COOH | |
| 10.97 | OC(CH$_3$)$_2$COOH | |
| 10.98 | OC(CH$_3$)$_2$COOCH$_3$ | |
| 10.99 | OC(CH$_3$)$_2$COOEt | |
| 10.100 | OCH$_2$COOH | |
| 10.101 | OSO$_2$CH$_3$ | |
| 10.102 | OSO$_2$CF$_3$ | |
| 10.103 | CH$_2$CHClCOOC$_2$H$_5$ | |
| 10.104 | CH$_2$CHClCON(C$_2$H$_5$)$_2$ | |
| 10.105 | CH$_2$CHClCONHOH | |
| 10.106 | CH$_2$CHClCOOCH$_2$C$_6$H$_5$ | |
| 10.107 | CH$_2$CH(CH$_3$)COOH | |
| 10.108 | CH$_2$CH(CH$_3$)COOC$_2$H$_5$ | |
| 10.109 | —COOCH$_2$—[cyclopropyl] | |
| 10.110 | COOC(CH$_3$)$_2$COOCH$_2$CH$_2$OC$_2$H$_5$ | |
| 10.111 | —COOC(CH$_3$)$_2$COOCH$_2$—[cyclopropyl] | |
| 10.112 | COOC(CH$_3$)$_2$CONHCH$_2$C≡CH | |
| 10.113 | COOC(CH$_3$)$_2$CON(CH$_2$CH$_3$)$_2$ | |
| 10.114 | OCH$_2$—[cyclopropyl] | |

TABLE 11

Compounds of formula lk (lk)

[Structure: pyrazole with Cl, CH3, SOCH3, CH3, N-CH3, R6 substituents]

| Comp. No. | R6 | M.p. |
|---|---|---|
| 11.1 | H | 88–91 |
| 11.2 | CN | |
| 11.3 | OCH$_3$ | |
| 11.4 | NHSO$_2$CH$_3$ | |
| 11.5 | OC$_3$H$_7$(iso) | |
| 11.6 | O-propargyl | |
| 11.7 | OCH(CH$_3$)C≡CH | |
| 11.8 | OCH$_2$COOCH$_2$CH$_3$ | |
| 11.9 | OCH$_2$CH$_2$OCH$_3$ | |
| 11.10 | OCH$_2$CH$_2$SCH$_2$CH$_3$ | |
| 11.11 | OCH$_2$COOCH$_3$ | |
| 11.12 | OCH$_2$COOC$_5$H$_{11}$(n) | |
| 11.13 | OCH$_2$COO-benzyl | |
| 11.14 | OCH(CH$_3$)COObenzyl | |
| 11.15 | SC$_3$H$_7$(iso) | |
| 11.16 | SCH$_2$COOCH$_3$ | |
| 11.17 | SCH$_2$COOC$_2$H$_5$ | |
| 11.18 | SCH(CH$_3$)COObenzyl | |
| 11.19 | SCH$_2$COObenzyl | |
| 11.20 | COOCH$_3$ | |
| 11.21 | COOC$_3$H$_7$(iso) | |
| 11.22 | COOC(CH$_3$)$_2$COOH | |
| 11.23 | COOC(CH$_3$)$_2$COO-allyl | |
| 11.24 | COOC(CH$_3$)$_2$COOCH$_3$ | |
| 11.25 | COOC(CH$_3$)$_2$COOethyl | |
| 11.26 | COOC(CH$_3$)$_2$CONH-allyl | |
| 11.27 | CH$_2$CHClCOOethyl | |
| 11.28 | CH$_2$CH=CH$_2$ | |
| 11.29 | CH$_2$CH$_2$CH$_3$ | |
| 11.30 | CH$_2$CH$_2$CF$_3$ | |
| 11.31 | OCH(CH$_3$)COOC$_2$H$_5$(R) | |
| 11.32 | OCH(CH$_3$)COOC$_2$H$_5$(S) | |
| 11.33 | OCH(CH$_3$)COOC$_2$H$_5$(R,S) | |
| 11.34 | CH$_2$CHClCOOH | |
| 11.35 | CH$_2$CHClCOOCH$_3$ | |
| 11.36 | CH$_2$CHClCOOC$_3$H$_7$(iso) | |

TABLE 11-continued

Compounds of formula lk (lk)

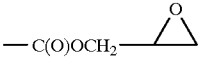

| Comp. No. | R6 | M.p. |
|---|---|---|
| 11.37 | CH2CHClCONHallyl | |
| 11.38 | CH2C(CH3)ClCOOH | |
| 11.39 | CH2C(CH3)ClCOOCH3 | |
| 11.40 | CH2C(CH3)ClCOOEt | |
| 11.41 | CH2C(CH3)ClCONHEt | |
| 11.42 | CH2CH2COOH | |
| 11.43 | CH2CH2COOCH3 | |
| 11.44 | CH2CH2COOEt | |
| 11.45 | CHClCHClCOOH | |
| 11.46 | CHClCHClCOOCH3 | |
| 11.47 | CHClCHClCOOEt | |
| 11.48 | CH2CH(OCH3)COOH | |
| 11.49 | CH2CH(OCH3)COOCH3 | |
| 11.50 | CH2CH(OCH3)COOEt | |
| 11.51 | CH2CH(SCH3)COOH | |
| 11.52 | CH2CH(SCH3)COOCH3 | |
| 11.53 | CH2CH(SCH3)COOEt | |
| 11.54 | CH=CHCOOH | |
| 11.55 | CH=CHCOOCH3 | |
| 11.56 | CH=CHCOOEt | |
| 11.57 | CH=CClCOOH | |
| 11.58 | CH=CClCOOCH3 | |
| 11.59 | COOEt | |
| 11.60 | CONH2 | |
| 11.61 |  | |
| 11.62 | CONHSO2CH3 | |
| 11.63 | COOCH2COOH | |
| 11.64 | COOCH2COOCH3 | |
| 11.65 | COOCH(CH3)COOH | |
| 11.66 | COOCH(CH3)COOCH3 | |
| 11.67 | COOCH(CH3)CH2COOH | |
| 11.68 | COOCH(CH3)CH2COOCH3 | |
| 11.69 | COOC(CH3)2CN | |
| 11.70 | COOCH2CH2OCH3 | |
| 11.71 | COOC(CH3)2COOCH2CH2OCH3 | |
| 11.72 | 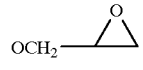 | |
| 11.73 | COOC(CH3)2COOCH2PHENYL | |
| 11.74 | COOCH2C≡CH | |
| 11.75 | COOC(CH3)2COOCH2C≡CH | |
| 11.76 | COOCH(CH3)C≡CH | |
| 11.77 | COOC(CH3)2COCH3 | |
| 11.78 | NHallyl | |
| 11.79 | N(COCH3)allyl | |
| 11.80 | N(Et)SO2CH3 | |
| 11.81 | N(allyl)SO2CH3 | |
| 11.82 | N(allyl)SO2Et | |
| 11.83 | SO2N(CH3)2 | |
| 11.84 | SO2NH2 | |
| 11.85 | SO2NHCOCH3 | |
| 11.86 | OH | |
| 11.87 | OEt | |
| 11.88 | Oallyl | |
| 11.89 | OCH2C≡CCH3 | |
| 11.90 | OCH(CH3)CH=CH2 | |
| 11.91 | OCH2CH2OCH2CH3 | |
| 11.92 | OCH2CH2OCH2CH2OCH3 | |
| 11.93 | 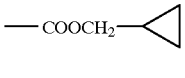 | |
| 11.94 | OCH2CH2NHCH3 | |
| 11.95 | OCH2CH2N(CH3)COCH3 | |
| 11.96 | OCH2CH2COOH | |
| 11.97 | OC(CH3)2COOH | |
| 11.98 | OC(CH3)2COOCH3 | |
| 11.99 | OC(CH3)2COOEt | |
| 11.100 | OCH2COOH | |
| 11.101 | OSO2CH3 | |
| 11.102 | OSO2CF3 | |
| 11.103 | CH2CHClCOOC2H5 | |
| 11.104 | CH2CHClCON(C2H5)2 | |
| 11.105 | CH2CHClCONHOH | |
| 11.106 | CH2CHClCOOCH2C6H5 | |
| 11.107 | CH2CH(CH3)COOH | |
| 11.108 | CH2CH(CH3)COOC2H5 | |
| 11.109 | —COOCH2—△ | |
| 11.110 | COOC(CH3)2COOCH2CH2OC2H5 | |
| 11.111 | —COOC(CH3)2COOCH2—△ | |
| 11.112 | COOC(CH3)2CONHCH2C≡CH | |
| 11.113 | COOC(CH3)2CON(CH2CH3)2 | |
| 11.114 | OCH2—△ | |

TABLE 12

Compounds of formula lm (lm)

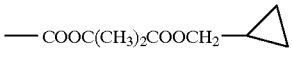

| Comp. No. | R6 | M.p. |
|---|---|---|
| 12.1 | H | 91–92 |
| 12.2 | CN | |
| 12.3 | OCH3 | |
| 12.4 | NHSO2CH3 | |
| 12.5 | OC3H7(iso) | |
| 12.6 | O-propargyl | |
| 12.7 | OCH(CH3)C≡CH | |
| 12.8 | OCH2COOCH2CH3 | |
| 12.9 | OCH2CH2OCH3 | |

TABLE 12-continued

Compounds of formula lm (lm)

Structure: 3-(2-chloro-4-methyl-5-R6-phenyl)-4-methyl-5-(methylsulfonyl)-1-methyl-1H-pyrazole

| Comp. No. | R_6 | M.p. |
|---|---|---|
| 12.10 | OCH$_2$CH$_2$SCH$_2$CH$_3$ | |
| 12.11 | OCH$_2$COOCH$_3$ | |
| 12.12 | OCH$_2$COOC$_5$H$_{11}$(n) | |
| 12.13 | OCH$_2$COO-benzyl | |
| 12.14 | OCH(CH$_3$)COObenzyl | |
| 12.15 | SC$_3$H$_7$(iso) | |
| 12.16 | SCH$_2$COOCH$_3$ | |
| 12.17 | SCH$_2$COOC$_2$H$_5$ | |
| 12.18 | SCH(CH$_3$)COObenzyl | |
| 12.19 | SCH$_2$COObenzyl | |
| 12.20 | COOCH$_3$ | |
| 12.21 | COOC$_3$H$_7$(iso) | |
| 12.22 | COOC(CH$_3$)$_2$COOH | |
| 12.23 | COOC(CH$_3$)$_2$COO-allyl | |
| 12.24 | COOC(CH$_3$)$_2$COOCH$_3$ | |
| 12.25 | COOC(CH$_3$)$_2$COOethyl | |
| 12.26 | COOC(CH$_3$)$_2$CONH-allyl | |
| 12.27 | CH$_2$CHClCOOethyl | |
| 12.28 | CH$_2$CH=CH$_2$ | |
| 12.29 | CH$_2$CH$_2$CH$_3$ | |
| 12.30 | CH$_2$CH$_2$CF$_3$ | |
| 12.31 | OCH(CH$_3$)COOC$_2$H$_5$(R) | |
| 12.32 | OCH(CH$_3$)COOC$_2$H$_5$(S) | |
| 12.33 | OCH(CH$_3$)COOC$_2$H$_5$(R,S) | |
| 12.34 | CH$_2$CHClCOOH | |
| 12.35 | CH$_2$CHClCOOCH$_3$ | |
| 12.36 | CH$_2$CHClCOOC$_3$H$_7$(iso) | |
| 12.37 | CH$_2$CHClCONHallyl | |
| 12.38 | CH$_2$C(CH$_3$)ClCOOH | |
| 12.39 | CH$_2$C(CH$_3$)ClCOOCH$_3$ | |
| 12.40 | CH$_2$C(CH$_3$)ClCOOEt | |
| 12.41 | CH$_2$C(CH$_3$)ClCONHEt | |
| 12.42 | CH$_2$CH$_2$COOH | |
| 12.43 | CH$_2$CH$_2$COOCH$_3$ | |
| 12.44 | CH$_2$CH$_2$COOEt | |
| 12.45 | CHClCHClCOOH | |
| 12.46 | CHClCHClCOOCH$_3$ | |
| 12.47 | CHClCHClCOOEt | |
| 12.48 | CH$_2$CH(OCH$_3$)COOH | |
| 12.49 | CH$_2$CH(OCH$_3$)COOCH$_3$ | |
| 12.50 | CH$_2$CH(OCH$_3$)COOEt | |
| 12.51 | CH$_2$CH(SCH$_3$)COOH | |
| 12.52 | CH$_2$CH(SCH$_3$)COOCH$_3$ | |
| 12.53 | CH$_2$CH(SCH$_3$)COOEt | |
| 12.54 | CH=CHCOOH | |
| 12.55 | CH=CHCOOCH$_3$ | |
| 12.56 | CH=CHCOOEt | |
| 12.57 | CH=CClCOOH | |
| 12.58 | CH=CClCOOCH$_3$ | |
| 12.59 | COOEt | |
| 12.60 | CONH$_2$ | |
| 12.61 | —C(O)OCH$_2$-(oxiranyl) | |
| 12.62 | CONHSO$_2$CH$_3$ | |
| 12.63 | COOCH$_2$COOH | |
| 12.64 | COOCH$_2$COOCH$_3$ | |
| 12.65 | COOCH(CH$_3$)COOH | |
| 12.66 | COOCH(CH$_3$)COOCH$_3$ | |
| 12.67 | COOCH(CH$_3$)CH$_2$COOH | |
| 12.68 | COOCH(CH$_3$)CH$_2$COOCH$_3$ | |
| 12.69 | COOC(CH$_3$)$_2$CN | |
| 12.70 | COOCH$_2$CH$_2$OCH$_3$ | |
| 12.71 | COOC(CH$_3$)$_2$COOCH$_2$CH$_2$OCH$_3$ | |
| 12.72 | COOC(CH$_3$)$_2$—C(O)O—CH$_2$-(oxiranyl) | |
| 12.73 | COOC(CH$_3$)$_2$COOCH$_2$PHENYL | |
| 12.74 | COOCH$_2$C≡CH | |
| 12.75 | COOC(CH$_3$)$_2$COOCH$_2$C≡CH | |
| 12.76 | COOCH(CH$_3$)C≡CH | |
| 12.77 | COOC(CH$_3$)$_2$COCH$_3$ | |
| 12.78 | NHallyl | |
| 12.79 | N(COCH$_3$)allyl | |
| 12.80 | N(Et)SO$_2$CH$_3$ | |
| 12.81 | N(allyl)SO$_2$CH$_3$ | |
| 12.82 | N(allyl)SO$_2$Et | |
| 12.83 | SO$_2$N(CH$_3$)$_2$ | |
| 12.84 | SO$_2$NH$_2$ | |
| 12.85 | SO$_2$NHCOCH$_3$ | |
| 12.86 | OH | |
| 12.87 | OEt | |
| 12.88 | Oallyl | |
| 12.89 | OCH$_2$C≡CCH$_3$ | |
| 12.90 | OCH(CH$_3$)CH=CH$_2$ | |
| 12.91 | OCH$_2$CH$_2$OCH$_2$CH$_3$ | |
| 12.92 | OCH$_2$CH$_2$OCH$_2$CH$_2$OCH$_3$ | |
| 12.93 | OCH$_2$-(oxiranyl) | |
| 12.94 | OCH$_2$CH$_2$NHCH$_3$ | |
| 12.95 | OCH$_2$CH$_2$N(CH$_3$)COCH$_3$ | |
| 12.96 | OCH$_2$CH$_2$COOH | |
| 12.97 | OC(CH$_3$)$_2$COOH | |
| 12.98 | OC(CH$_3$)$_2$COOCH$_3$ | |
| 12.99 | OC(CH$_3$)$_2$COOEt | |
| 12.100 | OCH$_2$COOH | |
| 12.101 | OSO$_2$CH$_3$ | |
| 12.102 | OSO$_2$CF$_3$ | |
| 12.103 | CH$_2$CHClCOOC$_2$H$_5$ | |
| 12.104 | CH$_2$CHClCON(C$_2$H$_5$)$_2$ | |
| 12.105 | CH$_2$CHClCONHOH | |
| 12.106 | CH$_2$CHClCOOCH$_2$C$_6$H$_5$ | |
| 12.107 | CH$_2$CH(CH$_3$)COOH | |
| 12.108 | CH$_2$CH(CH$_3$)COOC$_2$H$_5$ | |
| 12.109 | —COOCH$_2$-(cyclopropyl) | |
| 12.110 | COOC(CH$_3$)$_2$COOCH$_2$CH$_2$OC$_2$H$_5$ | |
| 12.111 | —COOC(CH$_3$)$_2$COOCH$_2$-(cyclopropyl) | |
| 12.112 | COOC(CH$_3$)$_2$CONHCH$_2$C≡CH | |
| 12.113 | COOC(CH$_3$)$_2$CON(CH$_2$CH$_3$)$_2$ | |

TABLE 12-continued

Compounds of formula lm (lm)

[Structure: 3-(2-chloro-4-methyl-5-R6-phenyl)-4-methyl-5-methylsulfonyl-1-methylpyrazole]

| Comp. No. | R6 | M.p. |
|---|---|---|
| 12.114 | OCH2—⟨cyclopropyl⟩ | |

TABLE 13

Compounds of formula ln (ln)

[Structure: 3-(4-bromo-2-chloro-5-R6-phenyl)-4-methyl-5-methylthio-1-methylpyrazole]

| Comp. No. | R6 | M.p. |
|---|---|---|
| 13.1 | H | 65–70 |
| 13.2 | CN | |
| 13.3 | OCH3 | |
| 13.4 | NHSO2CH3 | |
| 13.5 | OC3H7(iso) | |
| 13.6 | O-propargyl | |
| 13.7 | OCH(CH3)C≡CH | |
| 13.8 | OCH2COOCH2CH3 | |
| 13.9 | OCH2CH2OCH3 | |
| 13.10 | OCH2CH2SCH2CH3 | |
| 13.11 | OCH2COOCH3 | |
| 13.12 | OCH2COOC5H11(n) | |
| 13.13 | OCH2COO-benzyl | |
| 13.14 | OCH(CH3)COObenzyl | |
| 13.15 | SC3H7(iso) | |
| 13.16 | SCH2COOCH3 | |
| 13.17 | SCH2COOC2H5 | |
| 13.18 | SCH(CH3)COObenzyl | |
| 13.19 | SCH2COObenzyl | |
| 13.20 | COOCH3 | |
| 13.21 | COOC3H7(iso) | |
| 13.22 | COOC(CH3)2COOH | |
| 13.23 | COOC(CH3)2COO-allyl | |
| 13.24 | COOC(CH3)2COOCH3 | |
| 13.25 | COOC(CH3)2COOethyl | |
| 13.26 | COOC(CH3)2CONH-allyl | |
| 13.27 | CH2CHClCOOethyl | |
| 13.28 | CH2CH=CH2 | |
| 13.29 | CH2CH2CH3 | |
| 13.30 | CH2CH2CF3 | |
| 13.31 | OCH(CH3)COOC2H5(R) | |
| 13.32 | OCH(CH3)COOC2H5(S) | |
| 13.33 | OCH(CH3)COOC2H5(R,S) | |
| 13.34 | CH2CHClCOOH | |
| 13.35 | CH2CHClCOOCH3 | |
| 13.36 | CH2CHClCOOC3H7(iso) | |
| 13.37 | CH2CHClCONHallyl | |
| 13.38 | CH2C(CH3)ClCOOH | |
| 13.39 | CH2C(CH3)ClCOOCH3 | |
| 13.40 | CH2C(CH3)ClCOOEt | |
| 13.41 | CH2C(CH3)ClCONHEt | |
| 13.42 | CH2CH2COOH | |
| 13.43 | CH2CH2COOCH3 | |
| 13.44 | CH2CH2COOEt | |
| 13.45 | CHClCHClCOOH | |
| 13.46 | CHClCHClCOOCH3 | |
| 13.47 | CHClCHClCOOEt | |
| 13.48 | CH2CH(OCH3)COOH | |
| 13.49 | CH2CH(OCH3)COOCH3 | |
| 13.50 | CH2CH(OCH3)COOEt | |
| 13.51 | CH2CH(SCH3)COOH | |
| 13.52 | CH2CH(SCH3)COOCH3 | |
| 13.53 | CH2CH(SCH3)COOEt | |
| 13.54 | CH=CHCOOH | |
| 13.55 | CH=CHCOOCH3 | |
| 13.56 | CH=CHCOOEt | |
| 13.57 | CH=CClCOOH | |
| 13.58 | CH=CClCOOCH3 | |
| 13.59 | COOEt | |
| 13.60 | CONH2 | |
| 13.61 | —C(O)OCH2—⟨epoxide⟩ | |
| 13.62 | CONHSO2CH3 | |
| 13.63 | COOCH2COOH | |
| 13.64 | COOCH2COOCH3 | |
| 13.65 | COOCH(CH3)COOH | |
| 13.66 | COOCH(CH3)COOCH3 | |
| 13.67 | COOCH(CH3)CH2COOH | |
| 13.68 | COOCH(CH3)CH2COOCH3 | |
| 13.69 | COOC(CH3)2CN | |
| 13.70 | COOCH2CH2OCH3 | |
| 13.71 | COOC(CH3)2COOCH2CH2OCH3 | |
| 13.72 | COOC(CH3)2—C(O)O—CH2—⟨epoxide⟩ | |
| 13.73 | COOC(CH3)2COOCH2PHENYL | |
| 13.74 | COOCH2C≡CH | |
| 13.75 | COOC(CH3)2COOCH2C≡CH | |
| 13.76 | COOCH(CH3)C≡CH | |
| 13.77 | COOC(CH3)2COCH3 | |
| 13.78 | NHallyl | |
| 13.79 | N(COCH3)allyl | |
| 13.80 | N(Et)SO2CH3 | |
| 13.81 | N(allyl)SO2CH3 | |
| 13.82 | N(allyl)SO2Et | |
| 13.83 | SO2N(CH3)2 | |
| 13.84 | SO2NH2 | |
| 13.85 | SO2NHCOCH3 | |
| 13.86 | OH | |
| 13.87 | OEt | |
| 13.88 | Oallyl | |
| 13.89 | OCH2C≡CCH3 | |
| 13.90 | OCH(CH3)CH=CH2 | |
| 13.91 | OCH2CH2OCH2CH3 | |
| 13.92 | OCH2CH2OCH2CH2OCH3 | |
| 13.93 | OCH2—⟨epoxide⟩ | |
| 13.94 | OCH2CH2NHCH3 | |
| 13.95 | OCH2CH2N(CH3)COCH3 | |

TABLE 13-continued

Compounds of formula In

(In)

| Comp. No. | $R_6$ | M.p. |
|---|---|---|
| 13.96 | $OCH_2CH_2COOH$ | |
| 13.97 | $OC(CH_3)_2COOH$ | |
| 13.98 | $OC(CH_3)_2COOCH_3$ | |
| 13.99 | $OC(CH_3)_2COOEt$ | |
| 13.100 | $OCH_2COOH$ | |
| 13.101 | $OSO_2CH_3$ | |
| 13.102 | $OSO_2CF_3$ | |
| 13.103 | $CH_2CHClCOOC_2H_5$ | |
| 13.104 | $CH_2CHClCON(C_2H_5)_2$ | |
| 13.105 | $CH_2CHClCONHOH$ | |
| 13.106 | $CH_2CHClCOOCH_2C_6H_5$ | |
| 13.107 | $CH_2CH(CH_3)COOH$ | |
| 13.108 | $CH_2CH(CH_3)COOC_2H_5$ | |
| 13.109 | —COOCH$_2$—◁ | |
| 13.110 | $COOC(CH_3)_2COOCH_2CH_2OC_2H_5$ | |
| 13.111 | —COOC(CH$_3$)$_2$COOCH$_2$—◁ | |
| 13.112 | $COOC(CH_3)_2CONHCH_2C\equiv CH$ | |
| 13.113 | $COOC(CH_3)_2CON(CH_2CH_3)_2$ | |
| 13.114 | OCH$_2$—◁ | |

TABLE 13

Compounds of formula Io

(Io)

| Comp. No. | $R_6$ | M.p. |
|---|---|---|
| 14.1 | H | 115–117 |
| 14.2 | CN | |
| 14.3 | $OCH_3$ | |
| 14.4 | $NHSO_2CH_3$ | |
| 14.5 | $OC_3H_7(iso)$ | |
| 14.6 | O-propargyl | |
| 14.7 | $OCH(CH_3)C\equiv CH$ | |
| 14.8 | $OCH_2COOCH_2CH_3$ | |
| 14.9 | $OCH_2CH_2OCH_3$ | |
| 14.10 | $OCH_2CH_2SCH_2CH_3$ | |
| 14.11 | $OCH_2COOCH_3$ | |
| 14.12 | $OCH_2COOC_5H_{11}(n)$ | |
| 14.13 | $OCH_2COO$-benzyl | |
| 14.14 | $OCH(CH_3)COObenzyl$ | |
| 14.15 | $SC_3H_7(iso)$ | |
| 14.16 | $SCH_2COOCH_3$ | |

TABLE 13-continued

Compounds of formula Io

(Io)

| Comp. No. | $R_6$ | M.p. |
|---|---|---|
| 14.17 | $SCH_2COOC_2H_5$ | |
| 14.18 | $SCH(CH_3)COObenzyl$ | |
| 14.19 | $SCH_2COObenzyl$ | |
| 14.20 | $COOCH_3$ | |
| 14.21 | $COOC_3H_7(iso)$ | |
| 14.22 | $COOC(CH_3)_2COOH$ | |
| 14.23 | $COOC(CH_3)_2COO$-allyl | |
| 14.24 | $COOC(CH_3)_2COOCH_3$ | |
| 14.25 | $COOC(CH_3)_2COOethyl$ | |
| 14.26 | $COOC(CH_3)_2CONH$-allyl | |
| 14.27 | $CH_2CHClCOOethyl$ | |
| 14.28 | $CH_2CH=CH_2$ | |
| 14.29 | $CH_2CH_2CH_3$ | |
| 14.30 | $CH_2CH_2CF_3$ | |
| 14.31 | $OCH(CH_3)COOC_2H_5(R)$ | |
| 14.32 | $OCH(CH_3)COOC_2H_5(S)$ | |
| 14.33 | $OCH(CH_3)COOC_2H_5(R,S)$ | |
| 14.34 | $CH_2CHClCOOH$ | |
| 14.35 | $CH_2CHClCOOCH_3$ | |
| 14.36 | $CH_2CHClCOOC_3H_7(iso)$ | |
| 14.37 | $CH_2CHClCONHallyl$ | |
| 14.38 | $CH_2C(CH_3)ClCOOH$ | |
| 14.39 | $CH_2C(CH_3)ClCOOCH_3$ | |
| 14.40 | $CH_2C(CH_3)ClCOOEt$ | |
| 14.41 | $CH_2C(CH_3)ClCONHEt$ | |
| 14.42 | $CH_2CH_2COOH$ | |
| 14.43 | $CH_2CH_2COOCH_3$ | |
| 14.44 | $CH_2CH_2COOEt$ | |
| 14.45 | $CHClCHClCOOH$ | |
| 14.46 | $CHClCHClCOOCH_3$ | |
| 14.47 | $CHClCHClCOOEt$ | |
| 14.48 | $CH_2CH(OCH_3)COOH$ | |
| 14.49 | $CH_2CH(OCH_3)COOCH_3$ | |
| 14.50 | $CH_2CH(OCH_3)COOEt$ | |
| 14.51 | $CH_2CH(SCH_3)COOH$ | |
| 14.52 | $CH_2CH(SCH_3)COOCH_3$ | |
| 14.53 | $CH_2CH(SCH_3)COOEt$ | |
| 14.54 | $CH=CHCOOH$ | |
| 14.55 | $CH=CHCOOCH_3$ | |
| 14.56 | $CH=CHCOOEt$ | |
| 14.57 | $CH=CClCOOH$ | |
| 14.58 | $CH=CClCOOCH_3$ | |
| 14.59 | COOEt | |
| 14.60 | $CONH_2$ | |
| 14.61 | —C(O)OCH$_2$— | |
| 14.62 | $CONHSO_2CH_3$ | |
| 14.63 | $COOCH_2COOH$ | |
| 14.64 | $COOCH_2COOCH_3$ | |
| 14.65 | $COOCH(CH_3)COOH$ | |
| 14.66 | $COOCH(CH_3)COOCH_3$ | |
| 14.67 | $COOCH(CH_3)CH_2COOH$ | |
| 14.68 | $COOCH(CH_3)CH_2COOCH_3$ | |
| 14.69 | $COOC(CH_3)_2CN$ | |
| 14.70 | $COOCH_2CH_2OCH_3$ | |
| 14.71 | $COOC(CH_3)_2COOCH_2CH_2OCH_3$ | |
| 14.72 | $COOC(CH_3)_2-C(O)O-CH_2$— | |

TABLE 13-continued

Compounds of formula lo (lo)

| Comp. No. | R₆ | M.p. |
|---|---|---|
| 14.73 | COOC(CH₃)₂COOCH₂PHENYL | |
| 14.74 | COOCH₂C≡CH | |
| 14.75 | COOC(CH₃)₂COOCH₂C≡CH | |
| 14.76 | COOCH(CH₃)C≡CH | |
| 14.77 | COOC(CH₃)₂COCH₃ | |
| 14.78 | NHallyl | |
| 14.79 | N(COCH₃)allyl | |
| 14.80 | N(Et)SO₂CH₃ | |
| 14.81 | N(allyl)SO₂CH₃ | |
| 14.82 | N(allyl)SO₂Et | |
| 14.83 | SO₂N(CH₃)₂ | |
| 14.84 | SO₂NH₂ | |
| 14.85 | SO₂NHCOCH₃ | |
| 14.86 | OH | |
| 14.87 | OEt | |
| 14.88 | Oallyl | |
| 14.89 | OCH₂C≡CCH₃ | |
| 14.90 | OCH(CH₃)CH=CH₂ | |
| 14.91 | OCH₂CH₂OCH₂CH₃ | |
| 14.92 | OCH₂CH₂OCH₂CH₂OCH₃ | |
| 14.93 | OCH₂—(epoxide) | |
| 14.94 | OCH₂CH₂NHCH₃ | |
| 14.95 | OCH₂CH₂N(CH₃)COCH₃ | |
| 14.96 | OCH₂CH₂COOH | |
| 14.97 | OC(CH₃)₂COOH | |
| 14.98 | OC(CH₃)₂COOCH₃ | |
| 14.99 | OC(CH₃)₂COOEt | |
| 14.100 | OCH₂COOH | |
| 14.101 | OSO₂CH₃ | |
| 14.102 | OSO₂CF₃ | |
| 14.103 | CH₂CHClCOOC₂H₅ | |
| 14.104 | CH₂CHClCON(C₂H₅)₂ | |
| 14.105 | CH₂CHClCONHOH | |
| 14.106 | CH₂CHClCOOCH₂C₆H₅ | |
| 14.107 | CH₂CH(CH₃)COOH | |
| 14.108 | CH₂CH(CH₃)COOC₂H₅ | |
| 14.109 | —COOCH₂—(cyclopropyl) | |
| 14.110 | COOC(CH₃)₂COOCH₂CH₂OC₂H₅ | |
| 14.111 | —COOC(CH₃)₂COOCH₂—(cyclopropyl) | |
| 14.112 | COOC(CH₃)₂CONHCH₂C≡CH | |
| 14.113 | COOC(CH₃)₂CON(CH₂CH₃)₂ | |
| 14.114 | OCH₂—(cyclopropyl) | |

TABLE 15

Compounds of formula lp (lp)

| Comp. No. | R₆ | M.p. |
|---|---|---|
| 15.1 | H | 110–112 |
| 15.2 | CN | |
| 15.3 | OCH₃ | |
| 15.4 | NHSO₂CH₃ | |
| 15.5 | OC₃H₇(iso) | |
| 15.6 | O-propargyl | |
| 15.7 | OCH(CH₃)C≡CH | |
| 15.8 | OCH₂COOCH₂CH₃ | |
| 15.9 | OCH₂CH₂OCH₃ | |
| 15.10 | OCH₂CH₂SCH₂CH₃ | |
| 15.11 | OCH₂COOCH₃ | |
| 15.12 | OCH₂COOC₅H₁₁(n) | |
| 15.13 | OCH₂COO-benzyl | |
| 15.14 | OCH(CH₃)COObenzyl | |
| 15.15 | SC₃H₇(iso) | |
| 15.16 | SCH₂COOCH₃ | |
| 15.17 | SCH₂COOC₂H₅ | |
| 15.18 | SCH(CH₃)COObenzyl | |
| 15.19 | SCH₂COObenzyl | |
| 15.20 | COOCH₃ | |
| 15.21 | COOC₃H₇(iso) | |
| 15.22 | COOC(CH₃)₂COOH | |
| 15.23 | COOC(CH₃)₂COO-allyl | |
| 15.24 | COOC(CH₃)₂COOCH₃ | |
| 15.25 | COOC(CH₃)₂COOethyl | |
| 15.26 | COOC(CH₃)₂CONH-allyl | |
| 15.27 | CH₂CHClCOOethyl | |
| 15.28 | CH₂CH=CH₂ | |
| 15.29 | CH₂CH₂CH₃ | |
| 15.30 | CH₂CH₂CF₃ | |
| 15.31 | OCH(CH₃)COOC₂H₅(R) | |
| 15.32 | OCH(CH₃)COOC₂H₅(S) | |
| 15.33 | OCH(CH₃)COOC₂H₅(R,S) | |
| 15.34 | CH₂CHClCOOH | |
| 15.35 | CH₂CHClCOOCH₃ | |
| 15.36 | CH₂CHClCOOC₃H₇(iso) | |
| 15.37 | CH₂CHClCONHallyl | |
| 15.38 | CH₂C(CH₃)ClCOOH | |
| 15.39 | CH₂C(CH₃)ClCOOCH₃ | |
| 15.40 | CH₂C(CH₃)ClCOOEt | |
| 15.41 | CH₂C(CH₃)ClCONHEt | |
| 15.42 | CH₂CH₂COOH | |
| 15.43 | CH₂CH₂COOCH₃ | |
| 15.44 | CH₂CH₂COOEt | |
| 15.45 | CHClCHClCOOH | |
| 15.46 | CHClCHClCOOCH₃ | |
| 15.47 | CHClCHClCOOEt | |
| 15.48 | CH₂CH(OCH₃)COOH | |
| 15.49 | CH₂CH(OCH₃)COOCH₃ | |
| 15.50 | CH₂CH(OCH₃)COOEt | |
| 15.51 | CH₂CH(SCH₃)COOH | |
| 15.52 | CH₂CH(SCH₃)COOCH₃ | |
| 15.53 | CH₂CH(SCH₃)COOEt | |
| 15.54 | CH=CHCOOH | |
| 15.55 | CH=CHCOOCH₃ | |
| 15.56 | CH=CHCOOEt | |
| 15.57 | CH=CClCOOH | |
| 15.58 | CH=CClCOOCH₃ | |
| 15.59 | COOEt | |
| 15.60 | CONH₂ | |
| 15.61 | —C(O)OCH₂—(epoxide) | |

TABLE 15-continued

Compounds of formula lp (lp)

| Comp. No. | R$_6$ | M.p. |
|---|---|---|
| 15.62 | CONHSO$_2$CH$_3$ | |
| 15.63 | COOCH$_2$COOH | |
| 15.64 | COOCH$_2$COOCH$_3$ | |
| 15.65 | COOCH(CH$_3$)COOH | |
| 15.66 | COOCH(CH$_3$)COOCH$_3$ | |
| 15.67 | COOCH(CH$_3$)CH$_2$COOH | |
| 15.68 | COOCH(CH$_3$)CH$_2$COOCH$_3$ | |
| 15.69 | COOC(CH$_3$)$_2$CN | |
| 15.70 | COOCH$_2$CH$_2$OCH$_3$ | |
| 15.71 | COOC(CH$_3$)$_2$COOCH$_2$CH$_2$OCH$_3$ | |
| 15.72 | COOC(CH$_3$)$_2$—C(O)O—CH$_2$—(epoxide) | |
| 15.73 | COOC(CH$_3$)$_2$COOCH$_2$PHENYL | |
| 15.74 | COOCH$_2$C≡CH | |
| 15.75 | COOC(CH$_3$)$_2$COOCH$_2$C≡CH | |
| 15.76 | COOCH(CH$_3$)C≡CH | |
| 15.77 | COOC(CH$_3$)$_2$COCH$_3$ | |
| 15.78 | NHallyl | |
| 15.79 | N(COCH$_3$)allyl | |
| 15.80 | N(Et)SO$_2$CH$_3$ | |
| 15.81 | N(allyl)SO$_2$CH$_3$ | |
| 15.82 | N(allyl)SO$_2$Et | |
| 15.83 | SO$_2$N(CH$_3$)$_2$ | |
| 15.84 | SO$_2$NH$_2$ | |
| 15.85 | SO$_2$NHCOCH$_3$ | |
| 15.86 | OH | |
| 15.87 | OEt | |
| 15.88 | Oallyl | |
| 15.89 | OCH$_2$C≡CCH$_3$ | |
| 15.90 | OCH(CH$_3$)CH=CH$_2$ | |
| 15.91 | OCH$_2$CH$_2$OCH$_2$CH$_3$ | |
| 15.92 | OCH$_2$CH$_2$OCH$_2$CH$_2$OCH$_3$ | |
| 15.93 | OCH$_2$—(epoxide) | |
| 15.94 | OCH$_2$CH$_2$NHCH$_3$ | |

TABLE 15-continued

Compounds of formula lp (lp)

| Comp. No. | R$_6$ | M.p. |
|---|---|---|
| 15.95 | OCH$_2$CH$_2$N(CH$_3$)COCH$_3$ | |
| 15.96 | OCH$_2$CH$_2$COOH | |
| 15.97 | OC(CH$_3$)$_2$COOH | |
| 15.98 | OC(CH$_3$)$_2$COOCH$_3$ | |
| 15.99 | OC(CH$_3$)$_2$COOEt | |
| 15.100 | OCH$_2$COOH | |
| 15.101 | OSO$_2$CH$_3$ | |
| 15.102 | OSO$_2$CF$_3$ | |
| 15.103 | CH$_2$CHClCOOC$_2$H$_5$ | |
| 15.104 | CH$_2$CHClCON(C$_2$H$_5$)$_2$ | |
| 15.105 | CH$_2$CHClCONHOH | |
| 15.106 | CH$_2$CHClCOOCH$_2$C$_6$H$_5$ | |
| 15.107 | CH$_2$CH(CH$_3$)COOH | |
| 15.108 | CH$_2$CH(CH$_3$)COOC$_2$H$_5$ | |
| 15.109 | —COOCH$_2$—(cyclopropyl) | |
| 15.110 | COOC(CH$_3$)$_2$COOCH$_2$CH$_2$OC$_2$H$_5$ | |
| 15.111 | —COOC(CH$_3$)$_2$COOCH$_2$—(cyclopropyl) | |
| 15.112 | COOC(CH$_3$)$_2$CONHCH$_2$C≡CH | |
| 15.113 | COOC(CH$_3$)$_2$CON(CH$_2$CH$_3$)$_2$ | |
| 15.114 | OCH$_2$—(cyclopropyl) | |

TABLE 16

Compounds of formula Iq (Iq)

| Comp. No. | R$_6$ | R$_4$ | R$_1$ | R$_2$ | R$_3$ | n | M.p. |
|---|---|---|---|---|---|---|---|
| 16.1 | OCH$_3$ | Cl | Et | Me | Me | 0 | |
| 16.2 | OCH$_3$ | Cl | Et | Me | Me | 1 | |

TABLE 16-continued

Compounds of formula Iq

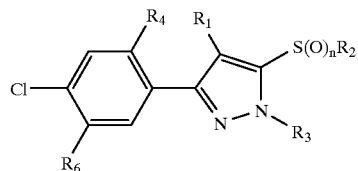

(Iq)

| Comp. No. | R$_6$ | R$_4$ | R$_1$ | R$_2$ | R$_3$ | n | M.p. |
|---|---|---|---|---|---|---|---|
| 16.3 | OCH$_3$ | Cl | Et | Me | Me | 2 | |
| 16.4 | OCH$_3$ | F | Et | Me | Me | 0 | |
| 16.5 | OCH$_3$ | F | Et | Me | Me | 1 | |
| 16.6 | OCH$_3$ | F | Et | Me | Me | 2 | |
| 16.7 | H | Cl | Et | Me | Me | 0 | oil |
| 16.8 | H | Cl | Et | Me | Me | 1 | oil |
| 16.9 | H | Cl | Et | Me | Me | 2 | oil |
| 16.10 | H | F | Et | Me | Me | 0 | |
| 16.11 | H | F | Et | Me | Me | 1 | |
| 16.12 | H | F | Et | Me | Me | 2 | |
| 16.13 | O-propargyl | Cl | Et | Me | Me | 0 | |
| 16.14 | O-propargyl | Cl | Et | Me | Me | 1 | |
| 16.15 | O-propargyl | Cl | Et | Me | Me | 2 | |
| 16.16 | O-propargyl | F | Et | Me | Me | 0 | |
| 16.17 | O-propargyl | F | Et | Me | Me | 1 | |
| 16.18 | O-propargyl | F | Et | Me | Me | 2 | |
| 16.19 | COOC$_3$H$_7$(iso) | Cl | Et | Me | Me | 0 | |
| 16.20 | COOC$_3$H$_7$(iso) | Cl | Et | Me | Me | 1 | |
| 16.21 | COOC$_3$H$_7$(iso) | Cl | Et | Me | Me | 2 | |
| 16.22 | COOC$_3$H$_7$(iso) | F | Et | Me | Me | 0 | |
| 16.23 | COOC$_3$H$_7$(iso) | F | Et | Me | Me | 1 | |
| 16.24 | COOC$_3$H$_7$(iso) | F | Et | Me | Me | 2 | |
| 16.25 | COOC$_3$H$_7$(iso) | H | Et | Me | Me | 0 | 49–51 |
| 16.26 | COOC$_3$H$_7$(iso) | H | Et | Me | Me | 1 | 110–112 |
| 16.27 | COOC$_3$H$_7$(iso) | H | Et | Me | Me | 2 | 102–103 |
| 16.28 | COOC(CH$_3$)$_2$COOCH$_3$ | Cl | Et | Me | Me | 0 | |
| 16.29 | COOC(CH$_3$)$_2$COOCH$_3$ | Cl | Et | Me | Me | 1 | |
| 16.30 | COOC(CH$_3$)$_2$COOCH$_3$ | Cl | Et | Me | Me | 2 | |
| 16.31 | COOC(CH$_3$)$_2$COOCH$_3$ | F | Et | Me | Me | 0 | |
| 16.32 | COOC(CH$_3$)$_2$COOCH$_3$ | F | Et | Me | Me | 1 | |
| 16.33 | COOC(CH$_3$)$_2$COOCH$_3$ | F | Et | Me | Me | 2 | |
| 16.34 | COOC(CH$_3$)$_2$COOCH$_3$ | H | Et | Me | Me | 0 | |
| 16.35 | COOC(CH$_3$)$_2$COOCH$_3$ | H | Et | Me | Me | 1 | |
| 16.36 | COOC(CH$_3$)$_2$COOCH$_3$ | H | Et | Me | Me | 2 | |
| 16.37 | SCH$_2$COOCH$_3$ | Cl | Et | Me | Me | 0 | |
| 16.38 | SCH$_2$COOCH$_3$ | Cl | Et | Me | Me | 1 | |
| 16.39 | SCH$_2$COOCH$_3$ | Cl | Et | Me | Me | 2 | |
| 16.40 | SCH$_2$COOCH$_3$ | F | Et | Me | Me | 0 | |
| 16.41 | SCH$_2$COOCH$_3$ | F | Et | Me | Me | 1 | |
| 16.42 | SCH$_2$COOCH$_3$ | F | Et | Me | Me | 2 | |
| 16.43 | SCH$_2$COOCH$_3$ | H | Et | Me | Me | 0 | |
| 16.44 | SCH$_2$COOCH$_3$ | H | Et | Me | Me | 1 | |
| 16.45 | SCH$_2$COOCH$_3$ | H | Et | Me | Me | 2 | |
| 16.46 | H | Cl | Me | Me | Et | 0 | 48–50 |
| 16.47 | H | Cl | Me | Me | Et | 1 | 113–114 |
| 16.48 | H | Cl | Me | Me | Et | 2 | 101–103 |
| 16.49 | H | F | Me | Me | Et | 0 | oil |
| 16.50 | H | F | Me | Me | Et | 1 | 87–89 |
| 16.51 | H | F | Me | Me | Et | 2 | 87–89 |
| 16.52 | OCH$_3$ | Cl | Me | Me | Et | 0 | |
| 16.53 | OCH$_3$ | Cl | Me | Me | Et | 1 | |
| 16.54 | OCH$_3$ | Cl | Me | Me | Et | 2 | |
| 16.55 | OCH$_3$ | F | Me | Me | Et | 0 | |
| 16.56 | OCH$_3$ | F | Me | Me | Et | 1 | |
| 16.57 | OCH$_3$ | F | Me | Me | Et | 2 | |
| 16.58 | O-propargyl | Cl | Me | Me | Et | 0 | |
| 16.59 | O-propargyl | Cl | Me | Me | Et | 1 | |
| 16.60 | O-propargyl | Cl | Me | Me | Et | 2 | |
| 16.61 | O-propargyl | F | Me | Me | Et | 0 | 64–67 |
| 16.62 | O-propargyl | F | Me | Me | Et | 1 | |
| 16.63 | O-propargyl | F | Me | Me | Et | 2 | 103–104 |
| 16.64 | COOC$_3$H$_7$(iso) | Cl | Me | Me | Et | 0 | 57–60 |
| 16.65 | COOC$_3$H$_7$(iso) | Cl | Me | Me | Et | 1 | 138–40 |

TABLE 16-continued

Compounds of formula Iq (Iq)

$$\text{structure: 4-Cl, 5-R}_6\text{-phenyl at pyrazole-3; R}_4, R_1, S(O)_nR_2, R_3 \text{ substituents}$$

| Comp. No. | R$_6$ | R$_4$ | R$_1$ | R$_2$ | R$_3$ | n | M.p. |
|---|---|---|---|---|---|---|---|
| 16.66 | COOC$_3$H$_7$(iso) | Cl | Me | Me | Et | 2 | 70–72 |
| 16.67 | COOC$_3$H$_7$(iso) | F | Me | Me | Et | 0 | |
| 16.68 | COOC$_3$H$_7$(iso) | F | Me | Me | Et | 1 | |
| 16.69 | COOC$_3$H$_7$(iso) | F | Me | Me | Et | 2 | |
| 16.70 | COOC$_3$H$_7$(iso) | H | Me | Me | Et | 0 | |
| 16.71 | COOC$_3$H$_7$(iso) | H | Me | Me | Et | 1 | |
| 16.72 | COOC$_3$H$_7$(iso) | H | Me | Me | Et | 2 | |
| 16.73 | COOC(CH$_3$)$_2$COOCH$_3$ | Cl | Me | Me | Et | 0 | |
| 16.74 | COOC(CH$_3$)$_2$COOCH$_3$ | Cl | Me | Me | Et | 1 | |
| 16.75 | COOC(CH$_3$)$_2$COOCH$_3$ | Cl | Me | Me | Et | 2 | |
| 16.76 | COOC(CH$_3$)$_2$COOCH$_3$ | F | Me | Me | Et | 0 | |
| 16.77 | COOC(CH$_3$)$_2$COOCH$_3$ | F | Me | Me | Et | 1 | |
| 16.78 | COOC(CH$_3$)$_2$COOCH$_3$ | F | Me | Me | Et | 2 | |
| 16.79 | COOC(CH$_3$)$_2$COOCH$_3$ | H | Me | Me | Et | 0 | |
| 16.80 | COOC(CH$_3$)$_2$COOCH$_3$ | H | Me | Me | Et | 1 | |
| 16.81 | COOC(CH$_3$)$_2$COOCH$_3$ | H | Me | Me | Et | 2 | |
| 16.82 | SCH$_2$COOCH$_3$ | Cl | Me | Me | Et | 0 | |
| 16.83 | SCH$_2$COOCH$_3$ | Cl | Me | Me | Et | 1 | |
| 16.84 | SCH$_2$COOCH$_3$ | Cl | Me | Me | Et | 2 | |
| 16.85 | SCH$_2$COOCH$_3$ | F | Me | Me | Et | 0 | |
| 16.86 | SCH$_2$COOCH$_3$ | F | Me | Me | Et | 1 | |
| 16.87 | SCH$_2$COOCH$_3$ | F | Me | Me | Et | 2 | |
| 16.88 | SCH$_2$COOCH$_3$ | H | Me | Me | Et | 0 | |
| 16.89 | SCH$_2$COOCH$_3$ | H | Me | Me | Et | 1 | |
| 16.90 | SCH$_2$COOCH$_3$ | H | Me | Me | Et | 2 | |
| 16.91 | H | Cl | Me | Me | tert-butyl | 0 | oil |
| 16.92 | H | Cl | Me | Me | tert-butyl | 1 | 93–94 |
| 16.93 | H | Cl | Me | Me | tert-butyl | 2 | 93–94 |
| 16.94 | H | Cl | Me | Me | CHF$_2$ | 0 | solid |
| 16.95 | H | Cl | Me | Me | CHF$_2$ | 1 | 78–79 |
| 16.96 | H | Cl | Me | Me | CHF$_2$ | 2 | 113–115 |
| 16.97 | H | F | Me | Me | CHF$_2$ | 0 | |
| 16.98 | H | F | Me | Me | CHF$_2$ | 1 | |
| 16.99 | H | F | Me | Me | CHF$_2$ | 2 | |
| 16.100 | OCH$_3$ | Cl | Me | Me | CHF$_2$ | 0 | |
| 16.101 | OCH$_3$ | Cl | Me | Me | CHF$_2$ | 1 | |
| 16.102 | OCH$_3$ | Cl | Me | Me | CHF$_2$ | 2 | |
| 16.103 | OCH$_3$ | F | Me | Me | CHF$_2$ | 0 | |
| 16.104 | OCH$_3$ | F | Me | Me | CHF$_2$ | 1 | |
| 16.105 | OCH$_3$ | F | Me | Me | CHF$_2$ | 2 | |
| 16.106 | O-propargyl | Cl | Me | Me | CHF$_2$ | 0 | |
| 16.107 | O-propargyl | Cl | Me | Me | CHF$_2$ | 1 | |
| 16.108 | O-propargyl | Cl | Me | Me | CHF$_2$ | 2 | |
| 16.109 | O-propargyl | F | Me | Me | CHF$_2$ | 0 | |
| 16.110 | O-propargyl | F | Me | Me | CHF$_2$ | 1 | |
| 16.111 | O-propargyl | F | Me | Me | CHF$_2$ | 2 | |
| 16.112 | COOC$_3$H$_7$(iso) | Cl | Me | Me | CHF$_2$ | 0 | |
| 16.113 | COOC$_3$H$_7$(iso) | Cl | Me | Me | CHF$_2$ | 1 | |
| 16.114 | COOC$_3$H$_7$(iso) | Cl | Me | Me | CHF$_2$ | 2 | |
| 16.115 | COOC$_3$H$_7$(iso) | F | Me | Me | CHF$_2$ | 0 | |
| 16.116 | COOC$_3$H$_7$(iso) | F | Me | Me | CHF$_2$ | 1 | |
| 16.117 | COOC$_3$H$_7$(iso) | F | Me | Me | CHF$_2$ | 2 | |
| 16.118 | COOC$_3$H$_7$(iso) | H | Me | Me | CHF$_2$ | 0 | |
| 16.119 | COOC$_3$H$_7$(iso) | H | Me | Me | CHF$_2$ | 1 | |
| 16.120 | COOC$_3$H$_7$(iso) | H | Me | Me | CHF$_2$ | 2 | |
| 16.121 | COOC(CH$_3$)$_2$COOCH$_3$ | Cl | Me | Me | CHF$_2$ | 0 | |
| 16.122 | COOC(CH$_3$)$_2$COOCH$_3$ | Cl | Me | Me | CHF$_2$ | 1 | |
| 16.123 | COOC(CH$_3$)$_2$COOCH$_3$ | Cl | Me | Me | CHF$_2$ | 2 | |
| 16.124 | COOC(CH$_3$)$_2$COOCH$_3$ | F | Me | Me | CHF$_2$ | 0 | |
| 16.125 | COOC(CH$_3$)$_2$COOCH$_3$ | F | Me | Me | CHF$_2$ | 1 | |
| 16.126 | COOC(CH$_3$)$_2$COOCH$_3$ | F | Me | Me | CHF$_2$ | 2 | |
| 16.127 | COOC(CH$_3$)$_2$COOCH$_3$ | H | Me | Me | CHF$_2$ | 0 | |
| 16.128 | COOC(CH$_3$)$_2$COOCH$_3$ | H | Me | Me | CHF$_2$ | 1 | |

TABLE 16-continued

Compounds of formula Iq

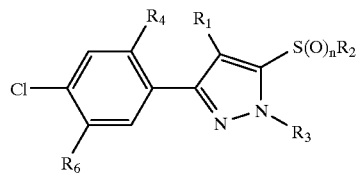
(Iq)

| Comp. No. | $R_6$ | $R_4$ | $R_1$ | $R_2$ | $R_3$ | n | M.p. |
|---|---|---|---|---|---|---|---|
| 16.129 | COOC(CH$_3$)$_2$COOCH$_3$ | H | Me | Me | CHF$_2$ | 2 | |
| 16.130 | SCH$_2$COOCH$_3$ | Cl | Me | Me | CHF$_2$ | 0 | |
| 16.131 | SCH$_2$COOCH$_3$ | Cl | Me | Me | CHF$_2$ | 1 | |
| 16.132 | SCH$_2$COOCH$_3$ | Cl | Me | Me | CHF$_2$ | 2 | |
| 16.133 | SCH$_2$COOCH$_3$ | F | Me | Me | CHF$_2$ | 0 | |
| 16.134 | SCH$_2$COOCH$_3$ | F | Me | Me | CHF$_2$ | 1 | |
| 16.135 | SCH$_2$COOCH$_3$ | F | Me | Me | CHF$_2$ | 2 | |
| 16.136 | SCH$_2$COOCH$_3$ | H | Me | Me | CHF$_2$ | 0 | |
| 16.137 | SCH$_2$COOCH$_3$ | H | Me | Me | CHF$_2$ | 1 | |
| 16.138 | SCH$_2$COOCH$_3$ | H | Me | Me | CHF$_2$ | 2 | |
| 16.139 | OCH$_3$ | Cl | Me | Et | Me | 0 | |
| 16.140 | OCH$_3$ | Cl | Me | Et | Me | 1 | |
| 16.141 | OCH$_3$ | Cl | Me | Et | Me | 2 | |
| 16.142 | OCH$_3$ | F | Me | Et | Me | 0 | |
| 16.143 | OCH$_3$ | F | Me | Et | Me | 1 | |
| 16.144 | OCH$_3$ | F | Me | Et | Me | 2 | |
| 16.145 | H | Cl | Me | Et | Me | 0 | oil |
| 16.146 | H | Cl | Me | Et | Me | 1 | oil |
| 16.147 | H | Cl | Me | Et | Me | 2 | 72–76 |
| 16.148 | H | F | Me | Et | Me | 0 | |
| 16.149 | H | F | Me | Et | Me | 1 | |
| 16.150 | H | F | Me | Et | Me | 2 | |
| 16.151 | O-propargyl | Cl | Me | Et | Me | 0 | |
| 16.152 | O-propargyl | Cl | Me | Et | Me | 1 | |
| 16.153 | O-propargyl | Cl | Me | Et | Me | 2 | |
| 16.154 | O-propargyl | F | Me | Et | Me | 0 | |
| 16.155 | O-propargyl | F | Me | Et | Me | 1 | |
| 16.156 | O-propargyl | F | Me | Et | Me | 2 | |
| 16.157 | COOC$_3$H$_7$(iso) | Cl | Me | Et | Me | 0 | |
| 16.158 | COOC$_3$H$_7$(iso) | Cl | Me | Et | Me | 1 | |
| 16.159 | COOC$_3$H$_7$(iso) | Cl | Me | Et | Me | 2 | |
| 16.160 | COOC$_3$H$_7$(iso) | F | Me | Et | Me | 0 | |
| 16.161 | COOC$_3$H$_7$(iso) | F | Me | Et | Me | 1 | |
| 16.162 | COOC$_3$H$_7$(iso) | F | Me | Et | Me | 2 | |
| 16.163 | COOC$_3$H$_7$(iso) | H | Me | Et | Me | 0 | |
| 16.164 | COOC$_3$H$_7$(iso) | H | Me | Et | Me | 1 | |
| 16.165 | COOC$_3$H$_7$(iso) | H | Me | Et | Me | 2 | |
| 16.166 | COOC(CH$_3$)$_2$COOCH$_3$ | Cl | Me | Et | Me | 0 | |
| 16.167 | COOC(CH$_3$)$_2$COOCH$_3$ | Cl | Me | Et | Me | 1 | |
| 16.168 | COOC(CH$_3$)$_2$COOCH$_3$ | Cl | Me | Et | Me | 2 | |
| 16.169 | COOC(CH$_3$)$_2$COOCH$_3$ | F | Me | Et | Me | 0 | |
| 16.170 | COOC(CH$_3$)$_2$COOCH$_3$ | F | Me | Et | Me | 1 | |
| 16.171 | COOC(CH$_3$)$_2$COOCH$_3$ | F | Me | Et | Me | 2 | |
| 16.172 | COOC(CH$_3$)$_2$COOCH$_3$ | H | Me | Et | Me | 0 | |
| 16.173 | COOC(CH$_3$)$_2$COOCH$_3$ | H | Me | Et | Me | 1 | |
| 16.174 | COOC(CH$_3$)$_2$COOCH$_3$ | H | Me | Et | Me | 2 | |
| 16.175 | CH$_2$CHClCOOH | Cl | Me | Et | Me | 0 | |
| 16.176 | CH$_2$CHClCOOH | Cl | Me | Et | Me | 1 | |
| 16.177 | CH$_2$CHClCOOH | Cl | Me | Et | Me | 2 | |
| 16.178 | CH$_2$CHClCOOH | F | Me | Et | Me | 0 | |
| 16.179 | CH$_2$CHClCOOH | F | Me | Et | Me | 1 | |
| 16.180 | CH$_2$CHClCOOH | F | Me | Et | Me | 2 | |
| 16.181 | CH$_2$CHClCOOH | H | Me | Et | Me | 0 | |
| 16.182 | CH$_2$CHClCOOH | H | Me | Et | Me | 1 | |
| 16.183 | CH$_2$CHClCOOH | H | Me | Et | Me | 2 | |
| 16.184 | CH$_2$CHClCOOEt | Cl | Me | Et | Me | 0 | |
| 16.185 | CH$_2$CHClCOOEt | Cl | Me | Et | Me | 1 | |
| 16.186 | CH$_2$CHClCOOEt | Cl | Me | Et | Me | 2 | |
| 16.187 | CH$_2$CHClCOOEt | F | Me | Et | Me | 0 | |
| 16.188 | CH$_2$CHClCOOEt | F | Me | Et | Me | 1 | |
| 16.189 | CH$_2$CHClCOOEt | F | Me | Et | Me | 2 | |
| 16.190 | CH$_2$CHClCOOEt | H | Me | Et | Me | 0 | |
| 16.191 | CH$_2$CHClCOOEt | H | Me | Et | Me | 1 | |

TABLE 16-continued

Compounds of formula Iq $$\text{(Iq)}$$

Structure: 4-Cl, 2-R$_4$, 5-R$_6$ substituted phenyl at position 3 of pyrazole; R$_1$ at position 4; S(O)$_n$R$_2$ at position 5; R$_3$ on N1.

| Comp. No. | R$_6$ | R$_4$ | R$_1$ | R$_2$ | R$_3$ | n | M.p. |
|---|---|---|---|---|---|---|---|
| 16.192 | CH$_2$CHClCOOEt | H | Me | Et | Me | 2 | |
| 16.193 | SCH$_2$COOCH$_3$ | Cl | Me | Et | Me | 0 | |
| 16.194 | SCH$_2$COOCH$_3$ | Cl | Me | Et | Me | 1 | |
| 16.195 | SCH$_2$COOCH$_3$ | Cl | Me | Et | Me | 2 | |
| 16.196 | SCH$_2$COOCH$_3$ | F | Me | Et | Me | 0 | |
| 16.197 | SCH$_2$COOCH$_3$ | F | Me | Et | Me | 1 | |
| 16.198 | SCH$_2$COOCH$_3$ | F | Me | Et | Me | 2 | |
| 16.199 | SCH$_2$COOCH$_3$ | H | Me | Et | Me | 0 | |
| 16.200 | SCH$_2$COOCH$_3$ | H | Me | Et | Me | 1 | |
| 16.201 | SCH$_2$COOCH$_3$ | H | Me | Et | Me | 2 | |
| 16.202 | CH$_2$CHClCOOH | Cl | Me | Me | Et | 0 | |
| 16.203 | CH$_2$CHClCOOH | Cl | Me | Me | Et | 1 | |
| 16.204 | CH$_2$CHClCOOH | Cl | Me | Me | Et | 2 | |
| 16.205 | CH$_2$CHClCOOH | F | Me | Me | Et | 0 | |
| 16.206 | CH$_2$CHClCOOH | F | Me | Me | Et | 1 | |
| 16.207 | CH$_2$CHClCOOH | F | Me | Me | Et | 2 | |
| 16.208 | CH$_2$CHClCOOH | H | Me | Me | Et | 0 | |
| 16.209 | CH$_2$CHClCOOH | H | Me | Me | Et | 1 | |
| 16.210 | CH$_2$CHClCOOH | H | Me | Me | Et | 2 | |
| 16.211 | CH$_2$CHClCOOEt | Cl | Me | Me | Et | 0 | |
| 16.212 | CH$_2$CHClCOOEt | Cl | Me | Me | Et | 1 | |
| 16.213 | CH$_2$CHClCOOEt | Cl | Me | Me | Et | 2 | |
| 16.214 | CH$_2$CHClCOOEt | F | Me | Me | Et | 0 | |
| 16.215 | CH$_2$CHClCOOEt | F | Me | Me | Et | 1 | |
| 16.216 | CH$_2$CHClCOOEt | F | Me | Me | Et | 2 | |
| 16.217 | CH$_2$CHClCOOEt | H | Me | Me | Et | 0 | |
| 16.218 | CH$_2$CHClCOOEt | H | Me | Me | Et | 1 | |
| 16.219 | CH$_2$CHClCOOEt | H | Me | Me | Et | 2 | |
| 16.220 | CH$_2$CHClCOOCH$_3$ | Cl | Me | Me | Et | 0 | |
| 16.221 | CH$_2$CHClCOOCH$_3$ | Cl | Me | Me | Et | 1 | |
| 16.222 | CH$_2$CHClCOOCH$_3$ | Cl | Me | Me | Et | 2 | |
| 16.223 | CH$_2$CHClCOOCH$_3$ | F | Me | Me | Et | 0 | |
| 16.224 | CH$_2$CHClCOOCH$_3$ | F | Me | Me | Et | 1 | |
| 16.225 | CH$_2$CHClCOOCH$_3$ | F | Me | Me | Et | 2 | |
| 16.226 | CH$_2$CHClCOOCH$_3$ | H | Me | Me | Et | 0 | |
| 16.227 | CH$_2$CHClCOOCH$_3$ | H | Me | Me | Et | 1 | |
| 16.228 | CH$_2$CHClCOOCH$_3$ | H | Me | Me | Et | 2 | |
| 16.229 | OCH$_2$COOEt | F | Me | Me | ET | 0 | |
| 16.230 | OCH$_2$COOEt | F | Me | Me | Et | 1 | |
| 16.231 | OCH$_2$COOEt | F | Me | Me | Et | 2 | |
| 16.232 | H | Cl | Me | Me | CH$_2$CH$_2$CH$_3$ | 0 | |
| 16.233 | H | Cl | Me | Me | CH$_2$CH$_2$CH$_3$ | 1 | |
| 16.234 | H | Cl | Me | Me | CH$_2$CH$_2$CH$_3$ | 2 | |
| 16.235 | H | F | Me | Me | CH$_2$CH$_2$CH$_3$ | 0 | |
| 16.236 | H | F | Me | Me | CH$_2$CH$_2$CH$_3$ | 1 | |
| 16.237 | H | F | Me | Me | CH$_2$CH$_2$CH$_3$ | 2 | |
| 16.238 | OCH$_3$ | Cl | Me | Me | CH$_2$CH$_2$CH$_3$ | 0 | |
| 16.239 | OCH$_3$ | Cl | Me | Me | CH$_2$CH$_2$CH$_3$ | 1 | |
| 16.240 | OCH$_3$ | Cl | Me | Me | CH$_2$CH$_2$CH$_3$ | 2 | |
| 16.241 | OCH$_3$ | F | Me | Me | CH$_2$CH$_2$CH$_3$ | 0 | |
| 16.242 | OCH$_3$ | F | Me | Me | CH$_2$CH$_2$CH$_3$ | 1 | |
| 16.243 | OCH$_3$ | F | Me | Me | CH$_2$CH$_2$CH$_3$ | 2 | |
| 16.244 | O-propargyl | Cl | Me | Me | CH$_2$CH$_2$CH$_3$ | 0 | |
| 16.245 | O-propargyl | Cl | Me | Me | CH$_2$CH$_2$CH$_3$ | 1 | |
| 16.246 | O-propargyl | Cl | Me | Me | CH$_2$CH$_2$CH$_3$ | 2 | |
| 16.247 | O-propargyl | F | Me | Me | CH$_2$CH$_2$CH$_3$ | 0 | |
| 16.248 | O-propargyl | F | Me | Me | CH$_2$CH$_2$CH$_3$ | 1 | |
| 16.249 | O-propargyl | F | Me | Me | CH$_2$CH$_2$CH$_3$ | 2 | |
| 16.250 | COOC$_3$H$_7$(iso) | Cl | Me | Me | CH$_2$CH$_2$CH$_3$ | 0 | |
| 16.251 | COOC$_3$H$_7$(iso) | Cl | Me | Me | CH$_2$CH$_2$CH$_3$ | 1 | |
| 16.252 | COOC$_3$H$_7$(iso) | Cl | Me | Me | CH$_2$CH$_2$CH$_3$ | 2 | |
| 16.253 | COOC$_3$H$_7$(iso) | F | Me | Me | CH$_2$CH$_2$CH$_3$ | 0 | |
| 16.254 | COOC$_3$H$_7$(iso) | F | Me | Me | CH$_2$CH$_2$CH$_3$ | 1 | |

TABLE 16-continued

Compounds of formula Iq

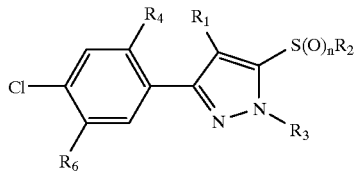

(Iq)

| Comp. No. | $R_6$ | $R_4$ | $R_1$ | $R_2$ | $R_3$ | n | M.p. |
|---|---|---|---|---|---|---|---|
| 16.255 | COOC$_3$H$_7$(iso) | F | Me | Me | CH$_2$CH$_2$CH$_3$ | 2 | |
| 16.256 | COOC$_3$H$_7$(iso) | H | Me | Me | CH$_2$CH$_2$CH$_3$ | 0 | |
| 16.257 | COOC$_3$H$_7$(iso) | H | Me | Me | CH$_2$CH$_2$CH$_3$ | 1 | |
| 16.258 | COOC$_3$H$_7$(iso) | H | Me | Me | CH$_2$CH$_2$CH$_3$ | 2 | |
| 16.259 | COOC(CH$_3$)$_2$COOCH$_3$ | Cl | Me | Me | CH$_2$CH$_2$CH$_3$ | 0 | |
| 16.260 | COOC(CH$_3$)$_2$COOCH$_3$ | Cl | Me | Me | CH$_2$CH$_2$CH$_3$ | 1 | |
| 16.261 | COOC(CH$_3$)$_2$COOCH$_3$ | Cl | Me | Me | CH$_2$CH$_2$CH$_3$ | 2 | |
| 16.262 | COOC(CH$_3$)$_2$COOCH$_3$ | F | Me | Me | CH$_2$CH$_2$CH$_3$ | 0 | |
| 16.263 | COOC(CH$_3$)$_2$COOCH$_3$ | F | Me | Me | CH$_2$CH$_2$CH$_3$ | 1 | |
| 16.264 | COOC(CH$_3$)$_2$COOCH$_3$ | F | Me | Me | CH$_2$CH$_2$CH$_3$ | 2 | |
| 16.265 | COOC(CH$_3$)$_2$COOCH$_3$ | H | Me | Me | CH$_2$CH$_2$CH$_3$ | 0 | |
| 16.266 | COOC(CH$_3$)$_2$COOCH$_3$ | H | Me | Me | CH$_2$CH$_2$CH$_3$ | 1 | |
| 16.267 | COOC(CH$_3$)$_2$COOCH$_3$ | H | Me | Me | CH$_2$CH$_2$CH$_3$ | 2 | |
| 16.268 | SCH$_2$COOCH$_3$ | Cl | Me | Me | CH$_2$CH$_2$CH$_3$ | 0 | |
| 16.269 | SCH$_2$COOCH$_3$ | Cl | Me | Me | CH$_2$CH$_2$CH$_3$ | 1 | |
| 16.270 | SCH$_2$COOCH$_3$ | Cl | Me | Me | CH$_2$CH$_2$CH$_3$ | 2 | |
| 16.271 | SCH$_2$COOCH$_3$ | F | Me | Me | CH$_2$CH$_2$CH$_3$ | 0 | |
| 16.272 | SCH$_2$COOCH$_3$ | F | Me | Me | CH$_2$CH$_2$CH$_3$ | 1 | |
| 16.273 | SCH$_2$COOCH$_3$ | F | Me | Me | CH$_2$CH$_2$CH$_3$ | 2 | |
| 16.274 | SCH$_2$COOCH$_3$ | H | Me | Me | CH$_2$CH$_2$CH$_3$ | 0 | |
| 16.275 | SCH$_2$COOCH$_3$ | H | Me | Me | CH$_2$CH$_2$CH$_3$ | 1 | |
| 16.276 | SCH$_2$COOCH$_3$ | H | Me | Me | CH$_2$CH$_2$CH$_3$ | 2 | |
| 16.277 | CH$_2$CHClCOOH | Cl | Me | Me | CH$_2$CH$_2$CH$_3$ | 0 | |
| 16.278 | CH$_2$CHClCOOH | Cl | Me | Me | CH$_2$CH$_2$CH$_3$ | 1 | |
| 16.279 | CH$_2$CHClCOOH | Cl | Me | Me | CH$_2$CH$_2$CH$_3$ | 2 | |
| 16.280 | CH$_2$CHClCOOH | F | Me | Me | CH$_2$CH$_2$CH$_3$ | 0 | |
| 16.281 | CH$_2$CHClCOOH | F | Me | Me | CH$_2$CH$_2$CH$_3$ | 1 | |
| 16.282 | CH$_2$CHClCOOH | F | Me | Me | CH$_2$CH$_2$CH$_3$ | 2 | |
| 16.283 | CH$_2$CHClCOOH | H | Me | Me | CH$_2$CH$_2$CH$_3$ | 0 | |
| 16.284 | CH$_2$CHClCOOH | H | Me | Me | CH$_2$CH$_2$CH$_3$ | 1 | |
| 16.285 | CH$_2$CHClCOOH | H | Me | Me | CH$_2$CH$_2$CH$_3$ | 2 | |
| 16.286 | CH$_2$CHClCOOEt | Cl | Me | Me | CH$_2$CH$_2$CH$_3$ | 0 | |
| 16.287 | CH$_2$CHClCOOEt | Cl | Me | Me | CH$_2$CH$_2$CH$_3$ | 1 | |
| 16.288 | CH$_2$CHClCOOEt | Cl | Me | Me | CH$_2$CH$_2$CH$_3$ | 2 | |
| 16.289 | CH$_2$CHClCOOEt | F | Me | Me | CH$_2$CH$_2$CH$_3$ | 0 | |
| 16.290 | CH$_2$CHClCOOEt | F | Me | Me | CH$_2$CH$_2$CH$_3$ | 1 | |
| 16.291 | CH$_2$CHClCOOEt | F | Me | Me | CH$_2$CH$_2$CH$_3$ | 2 | |
| 16.292 | CH$_2$CHClCOOEt | H | Me | Me | CH$_2$CH$_2$CH$_3$ | 0 | |
| 16.293 | CH$_2$CHClCOOEt | H | Me | Me | CH$_2$CH$_2$CH$_3$ | 1 | |
| 16.294 | CH$_2$CHClCOOEt | H | Me | Me | CH$_2$CH$_2$CH$_3$ | 2 | |
| 16.295 | CH$_2$CHClCOOCH$_3$ | Cl | Me | Me | CH$_2$CH$_2$CH$_3$ | 0 | |
| 16.296 | CH$_2$CHClCOOCH$_3$ | Cl | Me | Me | CH$_2$CH$_2$CH$_3$ | 1 | |
| 16.297 | CH$_2$CHClCOOCH$_3$ | Cl | Me | Me | CH$_2$CH$_2$CH$_3$ | 2 | |
| 16.298 | CH$_2$CHClCOOCH$_3$ | F | Me | Me | CH$_2$CH$_2$CH$_3$ | 0 | |
| 16.299 | CH$_2$CHClCOOCH$_3$ | F | Me | Me | CH$_2$CH$_2$CH$_3$ | 1 | |
| 16.300 | CH$_2$CHClCOOCH$_3$ | F | Me | Me | CH$_2$CH$_2$CH$_3$ | 2 | |
| 16.301 | CH$_2$CHClCOOCH$_3$ | H | Me | Me | CH$_2$CH$_2$CH$_3$ | 0 | |
| 16.302 | CH$_2$CHClCOOCH$_3$ | H | Me | Me | CH$_2$CH$_2$CH$_3$ | 1 | |
| 16.303 | CH$_2$CHClCOOCH$_3$ | H | Me | Me | CH$_2$CH$_2$CH$_3$ | 2 | |
| 16.304 | OCH$_3$ | F | Me | Me | CH$_2$CF$_3$ | 0 | oil |
| 16.305 | OCH$_3$ | F | Me | Me | CH$_2$CF$_3$ | 1 | |
| 16.306 | OCH$_3$ | F | Me | Me | CH$_2$CF$_3$ | 2 | |
| 16.307 | OCH$_3$ | Cl | Me | CHF$_2$ | Me | 0 | |
| 16.308 | OCH$_3$ | Cl | Me | CHF$_2$ | Me | 1 | |
| 16.309 | OCH$_3$ | Cl | Me | CHF$_2$ | Me | 2 | |
| 16.310 | OCH$_3$ | F | Me | CHF$_2$ | Me | 0 | |
| 16.311 | OCH$_3$ | F | Me | CHF$_2$ | Me | 1 | |
| 16.312 | OCH$_3$ | F | Me | CHF$_2$ | Me | 2 | |
| 16.313 | H | Cl | Me | CHF$_2$ | Me | 0 | |
| 16.314 | H | Cl | Me | CHF$_2$ | Me | 1 | |
| 16.315 | H | Cl | Me | CHF$_2$ | Me | 2 | |
| 16.316 | H | F | Me | CHF$_2$ | Me | 0 | |
| 16.317 | H | F | Me | CHF$_2$ | Me | 1 | |

TABLE 16-continued

Compounds of formula Iq

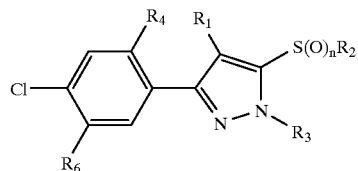

(Iq)

| Comp. No. | $R_6$ | $R_4$ | $R_1$ | $R_2$ | $R_3$ | n | M.p. |
|---|---|---|---|---|---|---|---|
| 16.318 | H | F | Me | $CHF_2$ | Me | 2 | |
| 16.319 | O-propargyl | Cl | Me | $CHF_2$ | Me | 0 | |
| 16.320 | O-propargyl | Cl | Me | $CHF_2$ | Me | 1 | |
| 16.321 | O-propargyl | Cl | Me | $CHF_2$ | Me | 2 | |
| 16.322 | O-propargyl | F | Me | $CHF_2$ | Me | 0 | |
| 16.323 | O-propargyl | F | Me | $CHF_2$ | Me | 1 | |
| 16.324 | O-propargyl | F | Me | $CHF_2$ | Me | 2 | |
| 16.325 | $COOC_3H_7$(iso) | Cl | Me | $CHF_2$ | Me | 0 | |
| 16.326 | $COOC_3H_7$(iso) | Cl | Me | $CHF_2$ | Me | 1 | |
| 16.327 | $COOC_3H_7$(iso) | Cl | Me | $CHF_2$ | Me | 2 | |
| 16.328 | $COOC_3H_7$(iso) | F | Me | $CHF_2$ | Me | 0 | |
| 16.329 | $COOC_3H_7$(iso) | F | Me | $CHF_2$ | Me | 1 | |
| 16.330 | $COOC_3H_7$(iso) | F | Me | $CHF_2$ | Me | 2 | |
| 16.331 | $COOC_3H_7$(iso) | H | Me | $CHF_2$ | Me | 0 | |
| 16.332 | $COOC_3H_7$(iso) | H | Me | $CHF_2$ | Me | 1 | |
| 16.333 | $COOC_3H_7$(iso) | H | Me | $CHF_2$ | Me | 2 | |
| 16.334 | $COOC(CH_3)_2COOCH_3$ | Cl | Me | $CHF_2$ | Me | 0 | |
| 16.335 | $COOC(CH_3)_2COOCH_3$ | Cl | Me | $CHF_2$ | Me | 1 | |
| 16.336 | $COOC(CH_3)_2COOCH_3$ | Cl | Me | $CHF_2$ | Me | 2 | |
| 16.337 | $COOC(CH_3)_2COOCH_3$ | F | Me | $CHF_2$ | Me | 0 | |
| 16.338 | $COOC(CH_3)_2COOCH_3$ | F | Me | $CHF_2$ | Me | 1 | |
| 16.339 | $COOC(CH_3)_2COOCH_3$ | F | Me | $CHF_2$ | Me | 2 | |
| 16.340 | $COOC(CH_3)_2COOCH_3$ | H | Me | $CHF_2$ | Me | 0 | |
| 16.341 | $COOC(CH_3)_2COOCH_3$ | H | Me | $CHF_2$ | Me | 1 | |
| 16.342 | $COOC(CH_3)_2COOCH_3$ | H | Me | $CHF_2$ | Me | 2 | |
| 16.343 | $CH_2CHClCOOH$ | Cl | Me | $CHF_2$ | Me | 0 | |
| 16.344 | $CH_2CHClCOOH$ | Cl | Me | $CHF_2$ | Me | 1 | |
| 16.345 | $CH_2CHClCOOH$ | Cl | Me | $CHF_2$ | Me | 2 | |
| 16.346 | $CH_2CHClCOOH$ | F | Me | $CHF_2$ | Me | 0 | |
| 16.347 | $CH_2CHClCOOH$ | F | Me | $CHF_2$ | Me | 1 | |
| 16.348 | $CH_2CHClCOOH$ | F | Me | $CHF_2$ | Me | 2 | |
| 16.349 | $CH_2CHClCOOH$ | H | Me | $CHF_2$ | Me | 0 | |
| 16.350 | $CH_2CHClCOOH$ | H | Me | $CHF_2$ | Me | 1 | |
| 16.351 | $CH_2CHClCOOH$ | H | Me | $CHF_2$ | Me | 2 | |
| 16.352 | $CH_2CHClCOOEt$ | Cl | Me | $CHF_2$ | Me | 0 | |
| 16.353 | $CH_2CHClCOOEt$ | Cl | Me | $CHF_2$ | Me | 1 | |
| 16.354 | $CH_2CHClCOOEt$ | Cl | Me | $CHF_2$ | Me | 2 | |
| 16.355 | $CH_2CHClCOOEt$ | F | Me | $CHF_2$ | Me | 0 | |
| 16.356 | $CH_2CHClCOOEt$ | F | Me | $CHF_2$ | Me | 1 | |
| 16.357 | $CH_2CHClCOOEt$ | F | Me | $CHF_2$ | Me | 2 | |
| 16.358 | $CH_2CHClCOOEt$ | H | Me | $CHF_2$ | Me | 0 | |
| 16.359 | $CH_2CHClCOOEt$ | H | Me | $CHF_2$ | Me | 1 | |
| 16.360 | $CH_2CHClCOOEt$ | H | Me | $CHF_2$ | Me | 2 | |
| 16.361 | $SCH_2COOCH_3$ | Cl | Me | $CHF_2$ | Me | 0 | |
| 16.362 | $SCH_2COOCH_3$ | Cl | Me | $CHF_2$ | Me | 1 | |
| 16.363 | $SCH_2COOCH_3$ | Cl | Me | $CHF_2$ | Me | 2 | |
| 16.364 | $SCH_2COOCH_3$ | F | Me | $CHF_2$ | Me | 0 | |
| 16.365 | $SCH_2COOCH_3$ | F | Me | $CHF_2$ | Me | 1 | |
| 16.366 | $SCH_2COOCH_3$ | F | Me | $CHF_2$ | Me | 2 | |
| 16.367 | $SCH_2COOCH_3$ | H | Me | $CHF_2$ | Me | 0 | |
| 16.368 | $SCH_2COOCH_3$ | H | Me | $CHF_2$ | Me | 1 | |
| 16.369 | $SCH_2COOCH_3$ | H | Me | $CHF_2$ | Me | 2 | |
| 16.370 | $OCH_3$ | Cl | Me | $CF_3$ | Me | 0 | |
| 16.371 | $OCH_3$ | Cl | Me | $CF_3$ | Me | 1 | |
| 16.372 | $OCH_3$ | Cl | Me | $CF_3$ | Me | 2 | |
| 16.373 | $OCH_3$ | F | Me | $CF_3$ | Me | 0 | |
| 16.374 | $OCH_3$ | F | Me | $CF_3$ | Me | 1 | |
| 16.375 | $OCH_3$ | F | Me | $CF_3$ | Me | 2 | |
| 16.376 | H | Cl | Me | $CF_3$ | Me | 0 | |
| 16.377 | H | Cl | Me | $CF_3$ | Me | 1 | |
| 16.378 | H | Cl | Me | $CF_3$ | Me | 2 | |
| 16.379 | H | F | Me | $CF_3$ | Me | 0 | |
| 16.380 | H | F | Me | $CF_3$ | Me | 1 | |

TABLE 16-continued

Compounds of formula Iq

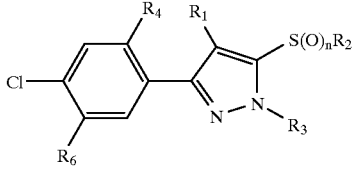

(Iq)

| Comp. No. | R₆ | R₄ | R₁ | R₂ | R₃ | n | M.p. |
|---|---|---|---|---|---|---|---|
| 16.381 | H | F | Me | CF₃ | Me | 2 | |
| 16.382 | O-propargyl | Cl | Me | CF₃ | Me | 0 | |
| 16.383 | O-propargyl | Cl | Me | CF₃ | Me | 1 | |
| 16.384 | O-propargyl | Cl | Me | CF₃ | Me | 2 | |
| 16.385 | O-propargyl | F | Me | CF₃ | Me | 0 | |
| 16.386 | O-propargyl | F | Me | CF₃ | Me | 1 | |
| 16.387 | O-propargyl | F | Me | CF₃ | Me | 2 | |
| 16.388 | COOC₃H₇(iso) | Cl | Me | CF₃ | Me | 0 | |
| 16.389 | COOC₃H₇(iso) | Cl | Me | CF₃ | Me | 1 | |
| 16.390 | COOC₃H₇(iso) | Cl | Me | CF₃ | Me | 2 | |
| 16.391 | COOC₃H₇(iso) | F | Me | CF₃ | Me | 0 | |
| 16.392 | COOC₃H₇(iso) | F | Me | CF₃ | Me | 1 | |
| 16.393 | COOC₃H₇(iso) | F | Me | CF₃ | Me | 2 | |
| 16.394 | COOC₃H₇(iso) | H | Me | CF₃ | Me | 0 | |
| 16.395 | COOC₃H₇(iso) | H | Me | CF₃ | Me | 1 | |
| 16.396 | COOC₃H₇(iso) | H | Me | CF₃ | Me | 2 | |
| 16.397 | COOC(CH₃)₂COOCH₃ | Cl | Me | CF₃ | Me | 0 | |
| 16.398 | COOC(CH₃)₂COOCH₃ | Cl | Me | CF₃ | Me | 1 | |
| 16.399 | COOC(CH₃)₂COOCH₃ | Cl | Me | CF₃ | Me | 2 | |
| 16.400 | COOC(CH₃)₂COOCH₃ | F | Me | CF₃ | Me | 0 | |
| 16.401 | COOC(CH₃)₂COOCH₃ | F | Me | CF₃ | Me | 1 | |
| 16.402 | COOC(CH₃)₂COOCH₃ | F | Me | CF₃ | Me | 2 | |
| 16.403 | COOC(CH₃)₂COOCH₃ | H | Me | CF₃ | Me | 0 | |
| 16.404 | COOC(CH₃)₂COOCH₃ | H | Me | CF₃ | Me | 1 | |
| 16.405 | COOC(CH₃)₂COOCH₃ | H | Me | CF₃ | Me | 2 | |
| 16.406 | CH₂CHClCOOH | Cl | Me | CF₃ | Me | 0 | |
| 16.407 | CH₂CHClCOOH | Cl | Me | CF₃ | Me | 1 | |
| 16.408 | CH₂CHClCOOH | Cl | Me | CF₃ | Me | 2 | |
| 16.409 | CH₂CHClCOOH | F | Me | CF₃ | Me | 0 | |
| 16.410 | CH₂CHClCOOH | F | Me | CF₃ | Me | 1 | |
| 16.411 | CH₂CHClCOOH | F | Me | CF₃ | Me | 2 | |
| 16.412 | CH₂CHClCOOH | H | Me | CF₃ | Me | 0 | |
| 16.413 | CH₂CHClCOOH | H | Me | CF₃ | Me | 1 | |
| 16.414 | CH₂CHClCOOH | H | Me | CF₃ | Me | 2 | |
| 16.415 | CH₂CHClCOOEt | Cl | Me | CF₃ | Me | 0 | |
| 16.416 | CH₂CHClCOOEt | Cl | Me | CF₃ | Me | 1 | |
| 16.417 | CH₂CHClCOOEt | Cl | Me | CF₃ | Me | 2 | |
| 16.418 | CH₂CHClCOOEt | F | Me | CF₃ | Me | 0 | |
| 16.419 | CH₂CHClCOOEt | F | Me | CF₃ | Me | 1 | |
| 16.420 | CH₂CHClCOOEt | F | Me | CF₃ | Me | 2 | |
| 16.421 | CH₂CHClCOOEt | H | Me | CF₃ | Me | 0 | |
| 16.422 | CH₂CHClCOOEt | H | Me | CF₃ | Me | 1 | |
| 16.423 | CH₂CHClCOOEt | H | Me | CF₃ | Me | 2 | |
| 16.424 | SCH₂COOCH₃ | Cl | Me | CF₃ | Me | 0 | |
| 16.425 | SCH₂COOCH₃ | Cl | Me | CF₃ | Me | 1 | |
| 16.426 | SCH₂COOCH₃ | Cl | Me | CF₃ | Me | 2 | |
| 16.427 | SCH₂COOCH₃ | F | Me | CF₃ | Me | 0 | |
| 16.428 | SCH₂COOCH₃ | F | Me | CF₃ | Me | 1 | |
| 16.429 | SCH₂COOCH₃ | F | Me | CF₃ | Me | 2 | |
| 16.430 | SCH₂COOCH₃ | H | Me | CF₃ | Me | 0 | |
| 16.431 | SCH₂COOCH₃ | H | Me | CF₃ | Me | 1 | |
| 16.432 | SCH₂COOCH₃ | H | Me | CF₃ | Me | 2 | |
| 16.433 | H | H | Et | Me | Me | 0 | 35–38 |
| 16.434 | NH₂ | Cl | Me | Me | Et | 0 | 82–83 |
| 16.435 | I | H | Et | Me | Me | 0 | 78–80 |

TABLE 17

Compounds of formula Ir

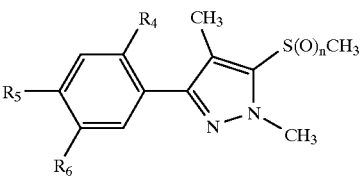

(Ir)

| Comp. No. | R6 | R4 | R5 | n | M.p. |
|---|---|---|---|---|---|
| 17.1 | H | CH3 | CH3 | 0 | |
| 17.2 | H | CH3 | CH3 | 1 | |
| 17.3 | H | CH3 | CH3 | 2 | |
| 17.4 | H | F | CF3 | 0 | oil |
| 17.5 | H | F | CF3 | 1 | 112–120 |
| 17.6 | H | F | CF3 | 2 | 121–123 |
| 17.7 | H | Cl | F | 0 | oil |
| 17.8 | H | Cl | F | 1 | 99–101 |
| 17.9 | H | Cl | F | 2 | 85–87 |
| 17.10 | H | F | F | 0 | solid |
| 17.11 | H | F | F | 1 | solid |
| 17.12 | H | F | F | 2 | |
| 17.13 | COOC(CH3)2COOH | H | H | 0 | |
| 17.14 | COOC(CH3)2COOH | H | H | 1 | |
| 17.15 | COOC(CH3)2COOH | H | H | 2 | 139–143 |
| 17.16 | COOC(CH3)2COOCH3 | H | H | 0 | |
| 17.17 | COOC(CH3)2COOCH3 | H | H | 1 | |
| 17.18 | COOC(CH3)2COOCH3 | H | H | 2 | oil |
| 17.19 | H | Br | Cl | 0 | 84–88 |
| 17.20 | H | Br | Cl | 1 | 91–93 |
| 17.21 | H | Br | Cl | 2 | 123–124 |

TABLE 18

Compounds of formula Is

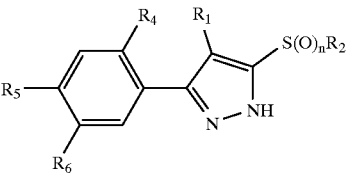

(Is)

| Comp. No. | R6 | R5 | R4 | R1 | R2 | M.p. |
|---|---|---|---|---|---|---|
| 18.1 | H | F | Cl | CH3 | SCH3 | oil |
| 18.2 | H | Cl | F | CH3 | SCH3 | 88–90 |
| 18.3 | OCH3 | Cl | F | CH3 | SCH3 | 98–100 |
| 18.4 | H | Cl | Cl | CH3 | SCH3 | oil |
| 18.5 | OCH3 | Cl | F | CH3 | SOCH3 | 171–173 |
| 18.6 | NO2 | Cl | F | CH3 | SOCH3 | solid |
| 18.7 | H | Cl | F | CH3 | SOCH3 | solid |
| 18.8 | H | CF3 | F | CH3 | SCH3 | solid |

TABLE 19

Compounds of formula It

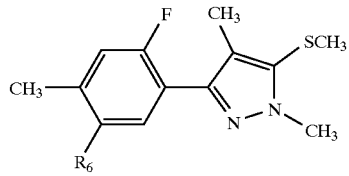

(It)

| Comp. No. | R6 | M.p. |
|---|---|---|
| 19.1 | H | |
| 19.2 | CN | |
| 19.3 | OCH3 | |
| 19.4 | NHSO2CH3 | |
| 19.5 | OC3H7(iso) | |
| 19.6 | O-propargyl | |
| 19.7 | OCH(CH3)C≡CH | |
| 19.8 | OCH2COOCH2CH3 | |
| 19.9 | OCH2CH2OCH3 | |
| 19.10 | OCH2CH2SCH2CH3 | |
| 19.11 | OCH2COOCH3 | |
| 19.12 | OCH2COOC5H11(n) | |
| 19.13 | OCH2COO-benzyl | |
| 19.14 | OCH(CH3)COObenzyl | |
| 19.15 | SC3H7(iso) | |
| 19.16 | SCH2COOCH3 | |
| 19.17 | SCH2COOC2H5 | |
| 19.18 | SCH(CH3)COObenzyl | |
| 19.19 | SCH2COObenzyl | |
| 19.20 | COOCH3 | |
| 19.21 | COOC3H7(iso) | |
| 19.22 | COOC(CH3)2COOH | |
| 19.23 | COOC(CH3)2COO-allyl | |
| 19.24 | COOC(CH3)2COOCH3 | |
| 19.25 | COOC(CH3)2COOethyl | |
| 19.26 | COOC(CH3)2CONH-allyl | |
| 19.27 | CH2CHClCOOethyl | |
| 19.28 | CH2CH=CH2 | |
| 19.29 | CH2CH2CH3 | |
| 19.30 | CH2CH2CF3 | |
| 19.31 | OCH(CH3)COOC2H5(R) | |
| 19.32 | OCH(CH3)COOC2H5(S) | |
| 19.33 | OCH(CH3)COOC2H5(R,S) | |
| 19.34 | CH2CHClCOOH | |
| 19.35 | CH2CHClCOOCH3 | |
| 19.36 | CH2CHClCOOC3H7(iso) | |
| 19.37 | CH2CHClCONHallyl | |
| 19.38 | CH2C(CH3)ClCOOH | |
| 19.39 | CH2C(CH3)ClCOOCH3 | |
| 19.40 | CH2C(CH3)ClCOOEt | |
| 19.41 | CH2C(CH3)ClCONHEt | |
| 19.42 | CH2CH2COOH | |
| 19.43 | CH2CH2COOCH3 | |
| 19.44 | CH2CH2COOEt | |
| 19.45 | CHClCHClCOOH | |
| 19.46 | CHClCHClCOOCH3 | |
| 19.47 | CHClCHClCOOEt | |
| 19.48 | CH2CH(OCH3)COOH | |
| 19.49 | CH2CH(OCH3)COOCH3 | |
| 19.50 | CH2CH(OCH3)COOEt | |
| 19.51 | CH2CH(SCH3)COOH | |
| 19.52 | CH2CH(SCH3)COOCH3 | |
| 19.53 | CH2CH(SCH3)COOEt | |
| 19.54 | CH=CHCOOH | |
| 19.55 | CH=CHCOOCH3 | |
| 19.56 | CH=CHCOOEt | |
| 19.57 | CH=CClCOOH | |
| 19.58 | CH=CClCOOCH3 | |
| 19.59 | COOEt | |
| 19.60 | CONH2 | |
| 19.61 | 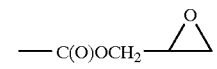 | |

TABLE 19-continued

Compounds of formula It (It)

[Structure: 3-(2-fluoro-4-methyl-5-R6-phenyl)-4-methyl-5-(methylthio)-1-methyl-1H-pyrazole]

| Comp. No. | R$_6$ | M.p. |
|---|---|---|
| 19.62 | CONHSO$_2$CH$_3$ | |
| 19.63 | COOCH$_2$COOH | |
| 19.64 | COOCH$_2$COOCH$_3$ | |
| 19.65 | COOCH(CH$_3$)COOH | |
| 19.66 | COOCH(CH$_3$)COOCH$_3$ | |
| 19.67 | COOCH(CH$_3$)CH$_2$COOH | |
| 19.68 | COOCH(CH$_3$)CH$_2$COOCH$_3$ | |
| 19.69 | COOC(CH$_3$)$_2$CN | |
| 19.70 | COOCH$_2$CH$_2$OCH$_3$ | |
| 19.71 | COOC(CH$_3$)$_2$COOCH$_2$CH$_2$OCH$_3$ | |
| 19.72 | COOC(CH$_3$)$_2$—C(O)O—CH$_2$-(epoxide) | |
| 19.73 | COOC(CH$_3$)$_2$COOCH$_2$PHENYL | |
| 19.74 | COOCH$_2$C≡CH | |
| 19.75 | COOC(CH$_3$)$_2$COOCH$_2$C≡CH | |
| 19.76 | COOCH(CH$_3$)C≡CH | |
| 19.77 | COOC(CH$_3$)$_2$COCH$_3$ | |
| 19.78 | NHallyl | |
| 19.79 | N(COCH$_3$)allyl | |
| 19.80 | N(Et)SO$_2$CH$_3$ | |
| 19.81 | N(allyl)SO$_2$CH$_3$ | |
| 19.82 | N(allyl)SO$_2$Et | |
| 19.83 | SO$_2$N(CH$_3$)$_2$ | |
| 19.84 | SO$_2$NH$_2$ | |
| 19.85 | SO$_2$NHCOCH$_3$ | |
| 19.86 | OH | |
| 19.87 | OEt | |
| 19.88 | Oallyl | |
| 19.89 | OCH$_2$C≡CCH$_3$ | |
| 19.90 | OCH(CH$_3$)CH=CH$_2$ | |
| 19.91 | OCH$_2$CH$_2$OCH$_2$CH$_3$ | |
| 19.92 | OCH$_2$CH$_2$OCH$_2$CH$_2$OCH$_3$ | |
| 19.93 | OCH$_2$-(epoxide) | |
| 19.94 | OCH$_2$CH$_2$NHCH$_3$ | |
| 19.95 | OCH$_2$CH$_2$N(CH$_3$)COCH$_3$ | |
| 19.96 | OCH$_2$CH$_2$COOH | |
| 19.97 | OC(CH$_3$)$_2$COOH | |
| 19.98 | OC(CH$_3$)$_2$COOCH$_3$ | |
| 19.99 | OC(CH$_3$)$_2$COOEt | |
| 19.100 | OCH$_2$COOH | |
| 19.101 | OSO$_2$CH$_3$ | |
| 19.102 | OSO$_2$CF$_3$ | |
| 19.103 | CH$_2$CHClCOOC$_2$H$_5$ | |
| 19.104 | CH$_2$CHClCON(C$_2$H$_5$)$_2$ | |
| 19.105 | CH$_2$CHClCONHOH | |
| 19.106 | CH$_2$CHClCOOCH$_2$C$_6$H$_5$ | |
| 19.107 | CH$_2$CH(CH$_3$)COOH | |
| 19.108 | CH$_2$CH(CH$_3$)COOC$_2$H$_5$ | |
| 19.109 | —COOCH$_2$-cyclopropyl | |
| 19.110 | COOC(CH$_3$)$_2$COOCH$_2$CH$_2$OC$_2$H$_5$ | |
| 19.111 | —COOC(CH$_3$)$_2$COOCH$_2$-cyclopropyl | |
| 19.112 | COOC(CH$_3$)$_2$CONHCH$_2$C≡CH | |
| 19.113 | COOC(CH$_3$)$_2$CON(CH$_2$CH$_3$)$_2$ | |
| 19.114 | OCH$_2$-cyclopropyl | |

TABLE 20

Compounds of formula Iu (Iu)

[Structure: 3-(2-fluoro-4-methyl-5-R6-phenyl)-4-methyl-5-(methylsulfinyl)-1-methyl-1H-pyrazole]

| Comp. No. | R$_6$ | M.p. |
|---|---|---|
| 20.1 | H | |
| 20.2 | CN | |
| 20.3 | OCH$_3$ | |
| 20.4 | NHSO$_2$CH$_3$ | |
| 20.5 | OC$_3$H$_7$(iso) | |
| 20.6 | O-propargyl | |
| 20.7 | OCH(CH$_3$)C≡CH | |
| 20.8 | OCH$_2$COOCH$_2$CH$_3$ | |
| 20.9 | OCH$_2$CH$_2$OCH$_3$ | |
| 20.10 | OCH$_2$CH$_2$SCH$_2$CH$_3$ | |
| 20.11 | OCH$_2$COOCH$_3$ | |
| 20.12 | OCH$_2$COOC$_5$H$_{11}$(n) | |
| 20.13 | OCH$_2$COO-benzyl | |
| 20.14 | OCH(CH$_3$)COObenzyl | |
| 20.15 | SC$_3$H$_7$(iso) | |
| 20.16 | SCH$_2$COOCH$_3$ | |
| 20.17 | SCH$_2$COOC$_2$H$_5$ | |
| 20.18 | SCH(CH$_3$)COObenzyl | |
| 20.19 | SCH$_2$COObenzyl | |
| 20.20 | COOCH$_3$ | |
| 20.21 | COOC$_3$H$_7$(iso) | |
| 20.22 | COOC(CH$_3$)$_2$COOH | |
| 20.23 | COOC(CH$_3$)$_2$COO-allyl | |
| 20.24 | COOC(CH$_3$)$_2$COOCH$_3$ | |
| 20.25 | COOC(CH$_3$)$_2$COOethyl | |
| 20.26 | COOC(CH$_3$)$_2$CONH-allyl | |
| 20.27 | CH$_2$CHClCOOethyl | |
| 20.28 | CH$_2$CH=CH$_2$ | |
| 20.29 | CH$_2$CH$_2$CH$_3$ | |
| 20.30 | CH$_2$CH$_2$CF$_3$ | |
| 20.31 | OCH(CH$_3$)COOC$_2$H$_5$(R) | |
| 20.32 | OCH(CH$_3$)COOC$_2$H$_5$(S) | |
| 20.33 | OCH(CH$_3$)COOC$_2$H$_5$(R,S) | |
| 20.34 | CH$_2$CHClCOOH | |

TABLE 20-continued

Compounds of formula Iu

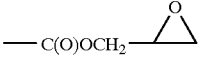

(Iu)

| Comp. No. | R6 | M.p. |
|---|---|---|
| 20.35 | CH2CHClCOOCH3 | |
| 20.36 | CH2CHClCOOC3H7(iso) | |
| 20.37 | CH2CHClCONHallyl | |
| 20.38 | CH2C(CH3)ClCOOH | |
| 20.39 | CH2C(CH3)ClCOOCH3 | |
| 20.40 | CH2C(CH3)ClCOOEt | |
| 20.41 | CH2C(CH3)ClCONHEt | |
| 20.42 | CH2CH2COOH | |
| 20.43 | CH2CH2COOCH3 | |
| 20.44 | CH2CH2COOEt | |
| 20.45 | CHClCHClCOOH | |
| 20.46 | CHClCHClCOOCH3 | |
| 20.47 | CHClCHClCOOEt | |
| 20.48 | CH2CH(OCH3)COOH | |
| 20.49 | CH2CH(OCH3)COOCH3 | |
| 20.50 | CH2CH(OCH3)COOEt | |
| 20.51 | CH2CH(SCH3)COOH | |
| 20.52 | CH2CH(SCH3)COOCH3 | |
| 20.53 | CH2CH(SCH3)COOEt | |
| 20.54 | CH=CHCOOH | |
| 20.55 | CH=CHCOOCH3 | |
| 20.56 | CH=CHCOOEt | |
| 20.57 | CH=CClCOOH | |
| 20.58 | CH=CClCOOCH3 | |
| 20.59 | COOEt | |
| 20.60 | CONH2 | |
| 20.61 | 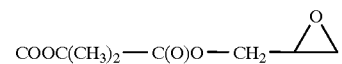 —C(O)OCH2— | |
| 20.62 | CONHSO2CH3 | |
| 20.63 | COOCH2COOH | |
| 20.64 | COOCH2COOCH3 | |
| 20.65 | COOCH(CH3)COOH | |
| 20.66 | COOCH(CH3)COOCH3 | |
| 20.67 | COOCH(CH3)CH2COOH | |
| 20.68 | COOCH(CH3)CH2COOCH3 | |
| 20.69 | COOC(CH3)2CN | |
| 20.70 | COOCH2CH2OCH3 | |
| 20.71 | COOC(CH3)2COOCH2CH2OCH3 | |
| 20.72 | COOC(CH3)2—C(O)O—CH2— 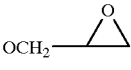 | |
| 20.73 | COOC(CH3)2COOCH2PHENYL | |
| 20.74 | COOCH2C≡CH | |
| 20.75 | COOC(CH3)2COOCH2C≡CH | |
| 20.76 | COOCH(CH3)C≡CH | |
| 20.77 | COOC(CH3)2COCH3 | |
| 20.78 | NHallyl | |
| 20.79 | N(COCH3)allyl | |
| 20.80 | N(Et)SO2CH3 | |
| 20.81 | N(allyl)SO2CH3 | |
| 20.82 | N(allyl)SO2Et | |
| 20.83 | SO2N(CH3)2 | |
| 20.84 | SO2NH2 | |
| 20.85 | SO2NHCOCH3 | |
| 20.86 | OH | |
| 20.87 | OEt | |
| 20.88 | Oallyl | |
| 20.89 | OCH2C≡CCH3 | |

TABLE 20-continued

Compounds of formula Iu

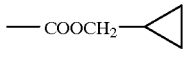

(Iu)

| Comp. No. | R6 | M.p. |
|---|---|---|
| 20.90 | OCH(CH3)CH=CH2 | |
| 20.91 | OCH2CH2OCH2CH3 | |
| 20.92 | OCH2CH2OCH2CH2OCH3 | |
| 20.93 | OCH2— 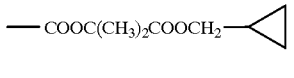 | |
| 20.94 | OCH2CH2NHCH3 | |
| 20.95 | OCH2CH2N(CH3)COCH3 | |
| 20.96 | OCH2CH2COOH | |
| 20.97 | OC(CH3)2COOH | |
| 20.98 | OC(CH3)2COOCH3 | |
| 20.99 | OC(CH3)2COOEt | |
| 20.100 | OCH2COOH | |
| 20.101 | OSO2CH3 | |
| 20.102 | OSO2CF3 | |
| 20.103 | CH2CHClCOOC2H5 | |
| 20.104 | CH2CHClCON(C2H5)2 | |
| 20.105 | CH2CHClCONHOH | |
| 20.106 | CH2CHClCOOCH2C6H5 | |
| 20.107 | CH2CH(CH3)COOH | |
| 20.108 | CH2CH(CH3)COOC2H5 | |
| 20.109 | —COOCH2— 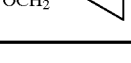 | |
| 20.110 | COOC(CH3)2COOCH2CH2OC2H5 | |
| 20.111 | —COOC(CH3)2COOCH2— 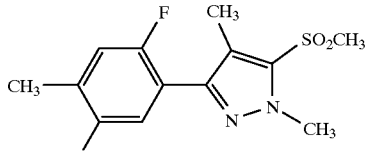 | |
| 20.112 | COOC(CH3)2CONHCH2C≡CH | |
| 20.113 | COOC(CH3)2CON(CH2CH3)2 | |
| 20.114 | OCH2— 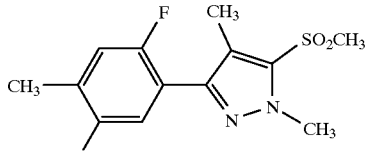 | |

TABLE 21

Compounds of formula Iv (Iv)

| Comp. No. | R6 | M.p. |
|---|---|---|
| 21.1 | H | |
| 21.2 | CN | |
| 21.3 | OCH3 | |
| 21.4 | NHSO2CH3 | |

TABLE 21-continued

Compounds of formula Iv (Iv)

| Comp. No. | $R_6$ | M.p. |
|---|---|---|
| 21.5 | $OC_3H_7(iso)$ | |
| 21.6 | O-propargyl | |
| 21.7 | $OCH(CH_3)C\equiv CH$ | |
| 21.8 | $OCH_2COOCH_2CH_3$ | |
| 21.9 | $OCH_2CH_2OCH_3$ | |
| 21.10 | $OCH_2CH_2SCH_2CH_3$ | |
| 21.11 | $OCH_2COOCH_3$ | |
| 21.12 | $OCH_2COOC_5H_{11}(n)$ | |
| 21.13 | $OCH_2COO$-benzyl | |
| 21.14 | $OCH(CH_3)COObenzyl$ | |
| 21.15 | $SC_3H_7(iso)$ | |
| 21.16 | $SCH_2COOCH_3$ | |
| 21.17 | $SCH_2COOC_2H_5$ | |
| 21.18 | $SCH(CH_3)COObenzyl$ | |
| 21.19 | $SCH_2COObenzyl$ | |
| 21.20 | $COOCH_3$ | |
| 21.21 | $COOC_3H_7(iso)$ | |
| 21.22 | $COOC(CH_3)_2COOH$ | |
| 21.23 | $COOC(CH_3)_2COO$-allyl | |
| 21.24 | $COOC(CH_3)_2COOCH_3$ | |
| 21.25 | $COOC(CH_3)_2COOethyl$ | |
| 21.26 | $COOC(CH_3)_2CONH$-allyl | |
| 21.27 | $CH_2CHClCOOethyl$ | |
| 21.28 | $CH_2CH=CH_2$ | |
| 21.29 | $CH_2CH_2CH_3$ | |
| 21.30 | $CH_2CH_2CF_3$ | |
| 21.31 | $OCH(CH_3)COOC_2H_5(R)$ | |
| 21.32 | $OCH(CH_3)COOC_2H_5(S)$ | |
| 21.33 | $OCH(CH_3)COOC_2H_5(R,S)$ | |
| 21.34 | $CH_2CHClCOOH$ | |
| 21.35 | $CH_2CHClCOOCH_3$ | |
| 21.36 | $CH_2CHClCOOC_3H_7(iso)$ | |
| 21.37 | $CH_2CHClCONHallyl$ | |
| 21.38 | $CH_2C(CH_3)ClCOOH$ | |
| 21.39 | $CH_2C(CH_3)ClCOOCH_3$ | |
| 21.40 | $CH_2C(CH_3)ClCOOEt$ | |
| 21.41 | $CH_2C(CH_3)ClCONHEt$ | |
| 21.42 | $CH_2CH_2COOH$ | |
| 21.43 | $CH_2CH_2COOCH_3$ | |
| 21.44 | $CH_2CH_2COOEt$ | |
| 21.45 | $CHClCHClCOOH$ | |
| 21.46 | $CHClCHClCOOCH_3$ | |
| 21.47 | $CHClCHClCOOEt$ | |
| 21.48 | $CH_2CH(OCH_3)COOH$ | |
| 21.49 | $CH_2CH(OCH_3)COOCH_3$ | |
| 21.50 | $CH_2CH(OCH_3)COOEt$ | |
| 21.51 | $CH_2CH(SCH_3)COOH$ | |
| 21.52 | $CH_2CH(SCH_3)COOCH_3$ | |
| 21.53 | $CH_2CH(SCH_3)COOEt$ | |
| 21.54 | $CH=CHCOOH$ | |
| 21.55 | $CH=CHCOOCH_3$ | |
| 21.56 | $CH=CHCOOEt$ | |
| 21.57 | $CH=CClCOOH$ | |
| 21.58 | $CH=CClCOOCH_3$ | |
| 21.59 | $COOEt$ | |
| 21.60 | $CONH_2$ | |
| 21.61 | —C(O)OCH$_2$—(epoxide) | |
| 21.62 | $CONHSO_2CH_3$ | |
| 21.63 | $COOCH_2COOH$ | |
| 21.64 | $COOCH_2COOCH_3$ | |
| 21.65 | $COOCH(CH_3)COOH$ | |
| 21.66 | $COOCH(CH_3)COOCH_3$ | |
| 21.67 | $COOCH(CH_3)CH_2COOH$ | |
| 21.68 | $COOCH(CH_3)CH_2COOCH_3$ | |
| 21.69 | $COOC(CH_3)_2CN$ | |
| 21.70 | $COOCH_2CH_2OCH_3$ | |
| 21.71 | $COOC(CH_3)_2COOCH_2CH_2OCH_3$ | |
| 21.72 | $COOC(CH_3)_2$—C(O)O—CH$_2$—(epoxide) | |
| 21.73 | $COOC(CH_3)_2COOCH_2PHENYL$ | |
| 21.74 | $COOCH_2C\equiv CH$ | |
| 21.75 | $COOC(CH_3)_2COOCH_2C\equiv CH$ | |
| 21.76 | $COOCH(CH_3)C\equiv CH$ | |
| 21.77 | $COOC(CH_3)_2COCH_3$ | |
| 21.78 | NHallyl | |
| 21.79 | $N(COCH_3)$allyl | |
| 21.80 | $N(Et)SO_2CH_3$ | |
| 21.81 | $N(allyl)SO_2CH_3$ | |
| 21.82 | $N(allyl)SO_2Et$ | |
| 21.83 | $SO_2N(CH_3)_2$ | |
| 21.84 | $SO_2NH_2$ | |
| 21.85 | $SO_2NHCOCH_3$ | |
| 21.86 | OH | |
| 21.87 | OEt | |
| 21.88 | Oallyl | |
| 21.89 | $OCH_2C\equiv CCH_3$ | |
| 21.90 | $OCH(CH_3)CH=CH_2$ | |
| 21.91 | $OCH_2CH_2OCH_2CH_3$ | |
| 21.92 | $OCH_2CH_2OCH_2CH_2OCH_3$ | |
| 21.93 | OCH$_2$—(epoxide) | |
| 21.94 | $OCH_2CH_2NHCH_3$ | |
| 21.95 | $OCH_2CH_2N(CH_3)COCH_3$ | |
| 21.96 | $OCH_2CH_2COOH$ | |
| 21.97 | $OC(CH_3)_2COOH$ | |
| 21.98 | $OC(CH_3)_2COOCH_3$ | |
| 21.99 | $OC(CH_3)_2COOEt$ | |
| 21.100 | $OCH_2COOH$ | |
| 21.101 | $OSO_2CH_3$ | |
| 21.102 | $OSO_2CF_3$ | |
| 21.103 | $CH_2CHClCOOC_2H_5$ | |
| 21.104 | $CH_2CHClCON(C_2H_5)_2$ | |
| 21.105 | $CH_2CHClCONHOH$ | |
| 21.106 | $CH_2CHClCOOCH_2C_6H_5$ | |
| 21.107 | $CH_2CH(CH_3)COOH$ | |
| 21.108 | $CH_2CH(CH_3)COOC_2H_5$ | |
| 21.109 | —COOCH$_2$—(cyclopropyl) | |
| 21.110 | $COOC(CH_3)_2COOCH_2CH_2OC_2H_5$ | |
| 21.111 | —COOC(CH$_3$)$_2$COOCH$_2$—(cyclopropyl) | |

TABLE 21-continued

Compounds of formula Iv (Iv)

| Comp. No. | R$_6$ | M.p. |
|---|---|---|
| 21.112 | COOC(CH$_3$)$_2$CONHCH$_2$C≡CH | |
| 21.113 | COOC(CH$_3$)$_2$CON(CH$_2$CH$_3$)$_2$ | |
| 21.114 | OCH$_2$—△ | |

TABLE 22

Compounds of formula lw (lw)

| Comp. No. | R$_6$ | M.p. |
|---|---|---|
| 22.1 | H | |
| 22.2 | CN | |
| 22.3 | OCH$_3$ | |
| 22.4 | NHSO$_2$CH$_3$ | |
| 22.5 | OC$_3$H$_7$(iso) | |
| 22.6 | O-propargyl | |
| 22.7 | OCH(CH$_3$)C≡CH | |
| 22.8 | OCH$_2$COOCH$_2$CH$_3$ | |
| 22.9 | OCH$_2$CH$_2$OCH$_3$ | |
| 22.10 | OCH$_2$CH$_2$SCH$_2$CH$_3$ | |
| 22.11 | OCH$_2$COOCH$_3$ | |
| 22.12 | OCH$_2$COOC$_5$H$_{11}$(n) | |
| 22.13 | OCH$_2$COO-benzyl | |
| 22.14 | OCH(CH$_3$)COObenzyl | |
| 22.15 | SC$_3$H$_7$(iso) | |
| 22.16 | SCH$_2$COOCH$_3$ | |
| 22.17 | SCH$_2$COOC$_2$H$_5$ | |
| 22.18 | SCH(CH$_3$)COObenzyl | |
| 22.19 | SCH$_2$COObenzyl | |
| 22.20 | COOCH$_3$ | |
| 22.21 | COOC$_3$H$_7$(iso) | |
| 22.22 | COO(CH$_3$)$_2$COOH | |
| 22.23 | COOC(CH$_3$)$_2$COO-allyl | |
| 22.24 | COOC(CH$_3$)$_2$COOCH$_3$ | |
| 22.25 | COO(CH$_3$)$_2$COOethyl | |
| 22.26 | COOC(CH$_3$)$_2$CONH-allyl | |
| 22.27 | CH$_2$CHClCOOethyl | |
| 22.28 | CH$_2$CH=CH$_2$ | |
| 22.29 | CH$_2$CH$_2$CH$_3$ | |
| 22.30 | CH$_2$CH$_2$CF$_3$ | |
| 22.31 | OCH(CH$_3$)COOC$_2$H$_5$(R) | |
| 22.32 | OCH(CH$_3$)COOC$_2$H$_5$(S) | |
| 22.33 | OCH(CH$_3$)COOC$_2$H$_5$(R,S) | |
| 22.34 | CH$_2$CHClCOOH | |
| 22.35 | CH$_2$CHClCOOCH$_3$ | |
| 22.36 | CH$_2$CHClCOOC$_3$H$_7$(iso) | |
| 22.37 | CH$_2$CHClCONHallyl | |
| 22.38 | CH$_2$C(CH$_3$)ClCOOH | |
| 22.39 | CH$_2$C(CH$_3$)ClCOOCH$_3$ | |
| 22.40 | CH$_2$C(CH$_3$)ClCOOEt | |

TABLE 22-continued

Compounds of formula lw (lw)

| Comp. No. | R$_6$ | M.p. |
|---|---|---|
| 22.41 | CH$_2$C(CH$_3$)ClCONHEt | |
| 22.42 | CH$_2$CH$_2$COOH | |
| 22.43 | CH$_2$CH$_2$COOCH$_3$ | |
| 22.44 | CH$_2$CH$_2$COOEt | |
| 22.45 | CHClCHClCOOH | |
| 22.46 | CHClCHClCOOCH$_3$ | |
| 22.47 | CHClCHClCOOEt | |
| 22.48 | CH$_2$CH(OCH$_3$)COOH | |
| 22.49 | CH$_2$CH(OCH$_3$)COOCH$_3$ | |
| 22.50 | CH$_2$CH(OCH$_3$)COOEt | |
| 22.51 | CH$_2$CH(SCH$_3$)COOH | |
| 22.52 | CH$_2$CH(SCH$_3$)COOCH$_3$ | |
| 22.53 | CH$_2$CH(SCH$_3$)COOEt | |
| 22.54 | CH=CHCOOH | |
| 22.55 | CH=CHCOOCH$_3$ | |
| 22.56 | CH=CHCOOEt | |
| 22.57 | CH=CClCOOH | |
| 22.58 | CH=CClCOOCH$_3$ | |
| 22.59 | COOEt | |
| 22.60 | CONH$_2$ | |
| 22.61 | —C(O)OCH$_2$—△(O) | |
| 22.62 | CONHSO$_2$CH$_3$ | |
| 22.63 | COOCH$_2$COOH | |
| 22.64 | COOCH$_2$COOCH$_3$ | |
| 22.65 | COOCH(CH$_3$)COOH | |
| 22.66 | COOCH(CH$_3$)COOCH$_3$ | |
| 22.67 | COOCH(CH$_3$)CH$_2$COOH | |
| 22.68 | COOCH(CH$_3$)CH$_2$COOCH$_3$ | |
| 22.69 | COOC(CH$_3$)$_2$CN | |
| 22.70 | COOCH$_2$CH$_2$OCH$_3$ | |
| 22.71 | COOC(CH$_3$)$_2$COOCH$_2$CH$_2$OCH$_3$ | |
| 22.72 | COOC(CH$_3$)$_2$—C(O)O—CH$_2$—△(O) | |
| 22.73 | COOC(CH$_3$)$_2$COOCH$_2$PHENYL | |
| 22.74 | COOCH$_2$C≡CH | |
| 22.75 | COOC(CH$_3$)$_2$COOCH$_2$C≡CH | |
| 22.76 | COOCH(CH$_3$)C≡CH | |
| 22.77 | COOC(CH$_3$)$_2$COCH$_3$ | |
| 22.78 | NHallyl | |
| 22.79 | N(COCH$_3$)allyl | |
| 22.80 | N(Et)SO$_2$CH$_3$ | |
| 22.81 | N(allyl)SO$_2$CH$_3$ | |
| 22.82 | N(allyl)SO$_2$Et | |
| 22.83 | SO$_2$N(CH$_3$)$_2$ | |
| 22.84 | SO$_2$NH$_2$ | |
| 22.85 | SO$_2$NHCOCH$_3$ | |
| 22.86 | OH | |
| 22.87 | OEt | |
| 22.88 | Oallyl | |
| 22.89 | OCH$_2$C≡CCH$_3$ | |
| 22.90 | OCH(CH$_3$)CH=CH$_2$ | |
| 22.91 | OCH$_2$CH$_2$OCH$_2$CH$_3$ | |
| 22.92 | OCH$_2$CH$_2$OCH$_2$CH$_2$OCH$_3$ | |
| 22.93 | OCH$_2$—△(O) | |

TABLE 22-continued

Compounds of formula lw

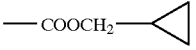
(lw)

| Comp. No. | R$_6$ | M.p. |
|---|---|---|
| 22.94 | OCH$_2$CH$_2$NHCH$_3$ | |
| 22.95 | OCH$_2$CH$_2$N(CH$_3$)COCH$_3$ | |
| 22.96 | OCH$_2$CH$_2$COOH | |
| 22.97 | OC(CH$_3$)$_2$COOH | |
| 22.98 | OC(CH$_3$)$_2$COOCH$_3$ | |
| 22.99 | OC(CH$_3$)$_2$COOEt | |
| 22.100 | OCH$_2$COOH | |
| 22.101 | OSO$_2$CH$_3$ | |
| 22.102 | OSO$_2$CF$_3$ | |
| 22.103 | CH$_2$CHClCOOC$_2$H$_5$ | |
| 22.104 | CH$_2$CHClCON(C$_2$H$_5$)$_2$ | |
| 22.105 | CH$_2$CHClCONHOH | |
| 22.106 | CH$_2$CHClCOOCH$_2$C$_6$H$_5$ | |
| 22.107 | CH$_2$CH(CH$_3$)COOH | |
| 22.108 | CH$_2$CH(CH$_3$)COOC$_2$H$_5$ | |
| 22.109 |  | |
| 22.110 | COOC(CH$_3$)$_2$COOCH$_2$CH$_2$OC$_2$H$_5$ | |
| 22.111 | 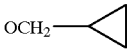 | |
| 22.112 | COOC(CH$_3$)$_2$CONHCH$_2$C≡CH | |
| 22.113 | COOC(CH$_3$)$_2$CON(CH$_2$CH$_3$)$_2$ | |
| 22.114 |  | |

TABLE 23

Compounds of formula lx

(lx)

| Comp. No. | R$_6$ | M.p. |
|---|---|---|
| 23.1 | H | |
| 23.2 | CN | |
| 23.3 | OCH$_3$ | |
| 23.4 | NHSO$_2$CH$_3$ | |
| 23.5 | OC$_3$H$_7$(iso) | |
| 23.6 | O-propargyl | |
| 23.7 | OCH(CH$_3$)C≡CH | |
| 23.8 | OCH$_2$COOCH$_2$CH$_3$ | |
| 23.9 | OCH$_2$CH$_2$OCH$_3$ | |
| 23.10 | OCH$_2$CH$_2$SCH$_2$CH$_3$ | |
| 23.11 | OCH$_2$COOCH$_3$ | |
| 23.12 | OCH$_2$COOC$_5$H$_{11}$(n) | |
| 23.13 | OCH$_2$COO-benzyl | |
| 23.14 | OCH(CH$_3$)COObenzyl | |
| 23.15 | SC$_3$H$_7$(iso) | |

TABLE 23-continued

Compounds of formula lx

| Comp. No. | R$_6$ | M.p. |
|---|---|---|
| 23.16 | SCH$_2$COOCH$_3$ | |
| 23.17 | SCH$_2$COOC$_2$H$_5$ | |
| 23.18 | SCH(CH$_3$)COObenzyl | |
| 23.19 | SCH$_2$COObenzyl | |
| 23.20 | COOCH$_3$ | |
| 23.21 | COOC$_3$H$_7$(iso) | |
| 23.22 | COO(CH$_3$)$_2$COOH | |
| 23.23 | COOC(CH$_3$)$_2$COO-allyl | |
| 23.24 | COOC(CH$_3$)$_2$COOCH$_3$ | |
| 23.25 | COO(CH$_3$)$_2$COOethyl | |
| 23.26 | COOC(CH$_3$)$_2$CONH-allyl | |
| 23.27 | CH$_2$CHClCOOethyl | |
| 23.28 | CH$_2$CH=CH$_2$ | |
| 23.29 | CH$_2$CH$_2$CH$_3$ | |
| 23.30 | CH$_2$CH$_2$CF$_3$ | |
| 23.31 | OCH(CH$_3$)COOC$_2$H$_5$(R) | |
| 23.32 | OCH(CH$_3$)COOC$_2$H$_5$(S) | |
| 23.33 | OCH(CH$_3$)COOC$_2$H$_5$(R,S) | |
| 23.34 | CH$_2$CHClCOOH | |
| 23.35 | CH$_2$CHClCOOCH$_3$ | |
| 23.36 | CH$_2$CHClCOOC$_3$H$_7$(iso) | |
| 23.37 | CH$_2$CHClCONHallyl | |
| 23.38 | CH$_2$C(CH$_3$)ClCOOH | |
| 23.39 | CH$_2$C(CH$_3$)ClCOOCH$_3$ | |
| 23.40 | CH$_2$C(CH$_3$)ClCOOEt | |
| 23.41 | CH$_2$C(CH$_3$)ClCONHEt | |
| 23.42 | CH$_2$CH$_2$COOH | |
| 23.43 | CH$_2$CH$_2$COOCH$_3$ | |
| 23.44 | CH$_2$CH$_2$COOEt | |
| 23.45 | CHClCHClCOOH | |
| 23.46 | CHClCHClCOOCH$_3$ | |
| 23.47 | CHClCHClCOOEt | |
| 23.48 | CH$_2$CH(OCH$_3$)COOH | |
| 23.49 | CH$_2$CH(OCH$_3$)COOCH$_3$ | |
| 23.50 | CH$_2$CH(OCH$_3$)COOEt | |
| 23.51 | CH$_2$CH(SCH$_3$)COOH | |
| 23.52 | CH$_2$CH(SCH$_3$)COOCH$_3$ | |
| 23.53 | CH$_2$CH(SCH$_3$)COOEt | |
| 23.54 | CH=CHCOOH | |
| 23.55 | CH=CHCOOCH$_3$ | |
| 23.56 | CH=CHCOOEt | |
| 23.57 | CH=CClCOOH | |
| 23.58 | CH=CClCOOCH$_3$ | |
| 23.59 | COOEt | |
| 23.60 | CONH$_2$ | |
| 23.61 | —C(O)OCH$_2$—⟨epoxide⟩ | |
| 23.62 | CONHSO$_2$CH$_3$ | |
| 23.63 | COOCH$_2$COOH | |
| 23.64 | COOCH$_2$COOCH$_3$ | |
| 23.65 | COOCH(CH$_3$)COOH | |
| 23.66 | COOCH(CH$_3$)COOCH$_3$ | |
| 23.67 | COOCH(CH$_3$)CH$_2$COOH | |
| 23.68 | COOCH(CH$_3$)CH$_2$COOCH$_3$ | |
| 23.69 | COOC(CH$_3$)$_2$CN | |
| 23.70 | COOCH$_2$CH$_2$OCH$_3$ | |
| 23.71 | COOC(CH$_3$)$_2$COOCH$_2$CH$_2$OCH$_3$ | |
| 23.72 | COOC(CH$_3$)$_2$—C(O)O—CH$_2$—⟨epoxide⟩ | |

TABLE 23-continued

Compounds of formula lx

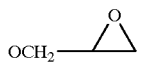
(lx)

| Comp. No. | R$_6$ | M.p. |
|---|---|---|
| 23.73 | COOC(CH$_3$)$_2$COOCH$_2$PHENYL | |
| 23.74 | COOCH$_2$C≡CH | |
| 23.75 | COOC(CH$_3$)$_2$COOCH$_2$C≡CH | |
| 23.76 | COOCH(CH$_3$)C≡CH | |
| 23.77 | COOC(CH$_3$)$_2$COCH$_3$ | |
| 23.78 | NHallyl | |
| 23.79 | N(COCH$_3$)allyl | |
| 23.80 | N(Et)SO$_2$CH$_3$ | |
| 23.81 | N(allyl)SO$_2$CH$_3$ | |
| 23.82 | N(allyl)SO$_2$Et | |
| 23.83 | SO$_2$N(CH$_3$)$_2$ | |
| 23.84 | SO$_2$NH$_2$ | |
| 23.85 | SO$_2$NHCOCH$_3$ | |
| 23.86 | OH | |
| 23.87 | OEt | |
| 23.88 | Oallyl | |
| 23.89 | OCH$_2$C≡CCH$_3$ | |
| 23.90 | OCH(CH$_3$)CH=CH$_2$ | |
| 23.91 | OCH$_2$CH$_2$OCH$_2$CH$_3$ | |
| 23.92 | OCH$_2$CH$_2$OCH$_2$CH$_2$OCH$_3$ | |
| 23.93 | 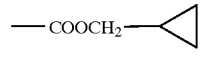 | |
| 23.94 | OCH$_2$CH$_2$NHCH$_3$ | |
| 23.95 | OCH$_2$CH$_2$N(CH$_3$)COCH$_3$ | |
| 23.96 | OCH$_2$CH$_2$COOH | |
| 23.97 | OC(CH$_3$)$_2$COOH | |
| 23.98 | OC(CH$_3$)$_2$COOCH$_3$ | |
| 23.99 | OC(CH$_3$)$_2$COOEt | |
| 23.100 | OCH$_2$COOH | |
| 23.101 | OSO$_2$CH$_3$ | |
| 23.102 | OSO$_2$CF$_3$ | |
| 23.103 | CH$_2$CHClCOOC$_2$H$_5$ | |
| 23.104 | CH$_2$CHClCON(C$_2$H$_5$)$_2$ | |
| 23.105 | CH$_2$CHClCONHOH | |
| 23.106 | CH$_2$CHClCOOCH$_2$C$_6$H$_5$ | |
| 23.107 | CH$_2$CH(CH$_3$)COOH | |
| 23.108 | CH$_2$CH(CH$_3$)COOC$_2$H$_5$ | |
| 23.109 | 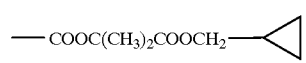 | |
| 23.110 | COOC(CH$_3$)$_2$COOCH$_2$CH$_2$OC$_2$H$_5$ | |
| 23.111 | 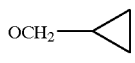 | |
| 23.112 | COOC(CH$_3$)$_2$CONHCH$_2$C≡CH | |
| 23.113 | COOC(CH$_3$)$_2$CON(CH$_2$CH$_3$)$_2$ | |
| 23.114 | OCH$_2$—△ | |

TABLE 24

Compounds of formula ly

(ly)

| Comp. No. | R$_6$ | M.p. |
|---|---|---|
| 24.1 | H | |
| 24.2 | CN | |
| 24.3 | OCH$_3$ | |
| 24.4 | NHSO$_2$CH$_3$ | |
| 24.5 | OC$_3$H$_7$(iso) | |
| 24.6 | O-propargyl | |
| 24.7 | OCH(CH$_3$)C≡CH | |
| 24.8 | OCH$_2$COOCH$_2$CH$_3$ | |
| 24.9 | OCH$_2$CH$_2$OCH$_3$ | |
| 24.10 | OCH$_2$CH$_2$SCH$_2$CH$_3$ | |
| 24.11 | OCH$_2$COOCH$_3$ | |
| 24.12 | OCH$_2$COOC$_5$H$_{11}$(n) | |
| 24.13 | OCH$_2$COO-benzyl | |
| 24.14 | OCH(CH$_3$)COObenzyl | |
| 24.15 | SC$_3$H$_7$(iso) | |
| 24.16 | SCH$_2$COOCH$_3$ | |
| 24.17 | SCH$_2$COOC$_2$H$_5$ | |
| 24.18 | SCH(CH$_3$)COObenzyl | |
| 24.19 | SCH$_2$COObenzyl | |
| 24.20 | COOCH$_3$ | |
| 24.21 | COOC$_3$H$_7$(iso) | |
| 24.22 | COO(CH$_3$)$_2$COOH | |
| 24.23 | COOC(CH$_3$)$_2$COO-allyl | |
| 24.24 | COOC(CH$_3$)$_2$COOCH$_3$ | |
| 24.25 | COO(CH$_3$)$_2$COOethyl | |
| 24.26 | COOC(CH$_3$)$_2$CONH-allyl | |
| 24.27 | CH$_2$CHClCOOethyl | |
| 24.28 | CH$_2$CH=CH$_2$ | |
| 24.29 | CH$_2$CH$_2$CH$_3$ | |
| 24.30 | CH$_2$CH$_2$CF$_3$ | |
| 24.31 | OCH(CH$_3$)COOC$_2$H$_5$(R) | |
| 24.32 | OCH(CH$_3$)COOC$_2$H$_5$(S) | |
| 24.33 | OCH(CH$_3$)COOC$_2$H$_5$(R,S) | |
| 24.34 | CH$_2$CHClCOOH | |
| 24.35 | CH$_2$CHClCOOCH$_3$ | |
| 24.36 | CH$_2$CHClCOOC$_3$H$_7$(iso) | |
| 24.37 | CH$_2$CHClCONHallyl | |
| 24.38 | CH$_2$C(CH$_3$)ClCOOH | |
| 24.39 | CH$_2$C(CH$_3$)ClCOOCH$_3$ | |
| 24.40 | CH$_2$C(CH$_3$)ClCOOEt | |
| 24.41 | CH$_2$C(CH$_3$)ClCONHEt | |
| 24.42 | CH$_2$CH$_2$COOH | |
| 24.43 | CH$_2$CH$_2$COOCH$_3$ | |
| 24.44 | CH$_2$CH$_2$COOEt | |
| 24.45 | CHClCHClCOOH | |
| 24.46 | CHClCHClCOOCH$_3$ | |
| 24.47 | CHClCHClCOOEt | |
| 24.48 | CH$_2$CH(OCH$_3$)COOH | |
| 24.49 | CH$_2$CH(OCH$_3$)COOCH$_3$ | |
| 24.50 | CH$_2$CH(OCH$_3$)COOEt | |
| 24.51 | CH$_2$CH(SCH$_3$)COOH | |
| 24.52 | CH$_2$CH(SCH$_3$)COOCH$_3$ | |
| 24.53 | CH$_2$CH(SCH$_3$)COOEt | |
| 24.54 | CH=CHCOOH | |
| 24.55 | CH=CHCOOCH$_3$ | |
| 24.56 | CH=CHCOOEt | |
| 24.57 | CH=CClCOOH | |
| 24.58 | CH=CClCOOCH$_3$ | |
| 24.59 | COOEt | |
| 24.60 | CONH$_2$ | |
| 24.61 | —C(O)OCH$_2$—△(O) | |
| 24.62 | CONHSO$_2$CH$_3$ | |

TABLE 24-continued

Compounds of formula ly $$\text{(ly)}$$

Structure: 3-(4-bromo-2-fluoro-5-R₆-phenyl)-4-methyl-5-(methylsulfonyl)-1-methyl-1H-pyrazole

| Comp. No. | R₆ | M.p. |
|---|---|---|
| 24.63 | COOCH₂COOH | |
| 24.64 | COOCH₂COOCH₃ | |
| 24.65 | COOCH(CH₃)COOH | |
| 24.66 | COOCH(CH₃)COOCH₃ | |
| 24.67 | COOCH(CH₃)CH₂COOH | |
| 24.68 | COOCH(CH₃)CH₂COOCH₃ | |
| 24.69 | COOC(CH₃)₂CN | |
| 24.70 | COOCH₂CH₂OCH₃ | |
| 24.71 | COOC(CH₃)₂COOCH₂CH₂OCH₃ | |
| 24.72 | COOC(CH₃)₂—C(O)O—CH₂—(epoxide) | |
| 24.73 | COOC(CH₃)₂COOCH₂PHENYL | |
| 24.74 | COOCH₂C≡CH | |
| 24.75 | COOC(CH₃)₂COOCH₂C≡CH | |
| 24.76 | COOCH(CH₃)C≡CH | |
| 24.77 | COOC(CH₃)₂COCH₃ | |
| 24.78 | NHallyl | |
| 24.79 | N(COCH₃)allyl | |
| 24.80 | N(Et)SO₂CH₃ | |
| 24.81 | N(allyl)SO₂CH₃ | |
| 24.82 | N(allyl)SO₂Et | |
| 24.83 | SO₂N(CH₃)₂ | |
| 24.84 | SO₂NH₂ | |
| 24.85 | SO₂NHCOCH₃ | |
| 24.86 | OH | |
| 24.87 | OEt | |
| 24.88 | Oallyl | |
| 24.89 | OCH₂C≡CCH₃ | |
| 24.90 | OCH(CH₃)CH=CH₂ | |
| 24.91 | OCH₂CH₂OCH₂CH₃ | |
| 24.92 | OCH₂CH₂OCH₂CH₂OCH₃ | |
| 24.93 | OCH₂—(epoxide) | |
| 24.94 | OCH₂CH₂NHCH₃ | |
| 24.95 | OCH₂CH₂N(CH₃)COCH₃ | |
| 24.96 | OCH₂CH₂COOH | |
| 24.97 | OC(CH₃)₂COOH | |
| 24.98 | OC(CH₃)₂COOCH₃ | |
| 24.99 | OC(CH₃)₂COOEt | |
| 24.100 | OCH₂COOH | |
| 24.101 | OSO₂CH₃ | |
| 24.102 | OSO₂CF₃ | |
| 24.103 | CH₂CHClCOOC₂H₅ | |
| 24.104 | CH₂CHClCON(C₂H₅)₂ | |
| 24.105 | CH₂CHClCONHOH | |
| 24.106 | CH₂CHClCOOCH₂C₆H₅ | |
| 24.107 | CH₂CH(CH₃)COOH | |
| 24.108 | CH₂CH(CH₃)COOC₂H₅ | |
| 24.109 | —COOCH₂—(cyclopropyl) | |
| 24.110 | COOC(CH₃)₂COOCH₂CH₂OC₂H₅ | |
| 24.111 | —COOC(CH₃)₂COOCH₂—(cyclopropyl) | |
| 24.112 | COOC(CH₃)₂CONHCH₂C≡CH | |
| 24.113 | COOC(CH₃)₂CON(CH₂CH₃)₂ | |
| 24.114 | OCH₂—(cyclopropyl) | |

TABLE 25

Compounds of formula Iz $$\text{(Iz)}$$

Structure: 3-(2-chloro-4-cyano-5-R₆-phenyl)-4-methyl-5-(methylthio)-1-methyl-1H-pyrazole

| Comp. No. | R₆ | M.p. |
|---|---|---|
| 25.1 | H | |
| 25.2 | CN | |
| 25.3 | OCH₃ | |
| 25.4 | NHSO₂CH₃ | |
| 25.5 | OC₃H₇(iso) | |
| 25.6 | O-propargyl | |
| 25.7 | OCH(CH₃)C≡CH | |
| 25.8 | OCH₂COOCH₂CH₃ | |
| 25.9 | OCH₂CH₂OCH₃ | |
| 25.10 | OCH₂CH₂SCH₂CH₃ | |
| 25.11 | OCH₂COOCH₃ | |
| 25.12 | OCH₂COOC₅H₁₁(n) | |
| 25.13 | OCH₂COO-benzyl | |
| 25.14 | OCH(CH₃)COObenzyl | |
| 25.15 | SC₃H₇(iso) | |
| 25.16 | SCH₂COOCH₃ | |
| 25.17 | SCH₂COOC₂H₅ | |
| 25.18 | SCH(CH₃)COObenzyl | |
| 25.19 | SCH₂COObenzyl | |
| 25.20 | COOCH₃ | |
| 25.21 | COOC₃H₇(iso) | |
| 25.22 | COOC(CH₃)₂COOH | |
| 25.23 | COOC(CH₃)₂COO-allyl | |
| 25.24 | COOC(CH₃)₂COOCH₃ | |
| 25.25 | COOC(CH₃)₂COOethyl | |
| 25.26 | COOC(CH₃)₂CONH-allyl | |
| 25.27 | CH₂CHClCOOethyl | |
| 25.28 | CH₂CH=CH₂ | |
| 25.29 | CH₂CH₂CH₃ | |
| 25.30 | CH₂CH₂CF₃ | |
| 25.31 | OCH(CH₃)COOC₂H₅(R) | |
| 25.32 | OCH(CH₃)COOC₂H₅(S) | |
| 25.33 | OCH(CH₃)COOC₂H₅(R,S) | |
| 25.34 | CH₂CHClCOOH | |
| 25.35 | CH₂CHClCOOCH₃ | |
| 25.36 | CH₂CHClCOOC₃H₇(iso) | |
| 25.37 | CH₂CHClCONHallyl | |
| 25.38 | CH₂C(CH₃)ClCOOH | |
| 25.39 | CH₂C(CH₃)ClCOOCH₃ | |
| 25.40 | CH₂C(CH₃)ClCOOEt | |
| 25.41 | CH₂C(CH₃)ClCONHEt | |

TABLE 25-continued

Compounds of formula Iz (Iz): 3-(2-chloro-4-cyano-phenyl substituted with R6)-1,4-dimethyl-5-methylthio-pyrazole

| Comp. No. | R$_6$ | M.p. |
|---|---|---|
| 25.42 | CH$_2$CH$_2$COOH | |
| 25.43 | CH$_2$CH$_2$COOCH$_3$ | |
| 25.44 | CH$_2$CH$_2$COOEt | |
| 25.45 | CHClCHClCOOH | |
| 25.46 | CHClCHClCOOCH$_3$ | |
| 25.47 | CHClCHClCOOEt | |
| 25.48 | CH$_2$CH(OCH$_3$)COOH | |
| 25.49 | CH$_2$CH(OCH$_3$)COOCH$_3$ | |
| 25.50 | CH$_2$CH(OCH$_3$)COOEt | |
| 25.51 | CH$_2$CH(SCH$_3$)COOH | |
| 25.52 | CH$_2$CH(SCH$_3$)COOCH$_3$ | |
| 25.53 | CH$_2$CH(SCH$_3$)COOEt | |
| 25.54 | CH=CHCOOH | |
| 25.55 | CH=CHCOOCH$_3$ | |
| 25.56 | CH=CHCOOEt | |
| 25.57 | CH=CClCOOH | |
| 25.58 | CH=CClCOOCH$_3$ | |
| 25.59 | COOEt | |
| 25.60 | CONH$_2$ | |
| 25.61 | —C(O)OCH$_2$-(oxiranyl) | |
| 25.62 | CONHSO$_2$CH$_3$ | |
| 25.63 | COOCH$_2$COOH | |
| 25.64 | COOCH$_2$COOCH$_3$ | |
| 25.65 | COOCH(CH$_3$)COOH | |
| 25.66 | COOCH(CH$_3$)COOCH$_3$ | |
| 25.67 | COOCH(CH$_3$)CH$_2$COOH | |
| 25.68 | COOCH(CH$_3$)CH$_2$COOCH$_3$ | |
| 25.69 | COOC(CH$_3$)$_2$CN | |
| 25.70 | COOCH$_2$CH$_2$OCH$_3$ | |
| 25.71 | COOC(CH$_3$)$_2$COOCH$_2$CH$_2$OCH$_3$ | |
| 25.72 | COOC(CH$_3$)$_2$—C(O)O—CH$_2$-(oxiranyl) | |
| 25.73 | COOC(CH$_3$)$_2$COOCH$_2$PHENYL | |
| 25.74 | COOCH$_2$C≡CH | |
| 25.75 | COOC(CH$_3$)$_2$COOCH$_2$C≡CH | |
| 25.76 | COOCH(CH$_3$)C≡CH | |
| 25.77 | COOC(CH$_3$)$_2$COCH$_3$ | |
| 25.78 | NHallyl | |
| 25.79 | N(COCH$_3$)allyl | |
| 25.80 | N(Et)SO$_2$CH$_3$ | |
| 25.81 | N(allyl)SO$_2$CH$_3$ | |
| 25.82 | N(allyl)SO$_2$Et | |
| 25.83 | SO$_2$N(CH$_3$)$_2$ | |
| 25.84 | SO$_2$NH$_2$ | |
| 25.85 | SO$_2$NHCOCH$_3$ | |
| 25.86 | OH | |
| 25.87 | OEt | |
| 25.88 | Oallyl | |
| 25.89 | OCH$_2$C≡CCH$_3$ | |
| 25.90 | OCH(CH$_3$)CH=CH$_2$ | |
| 25.91 | OCH$_2$CH$_2$OCH$_2$CH$_3$ | |
| 25.92 | OCH$_2$CH$_2$OCH$_2$CH$_2$OCH$_3$ | |
| 25.93 | OCH$_2$-(oxiranyl) | |
| 25.94 | OCH$_2$CH$_2$NHCH$_3$ | |
| 25.95 | OCH$_2$CH$_2$N(CH$_3$)COCH$_3$ | |
| 25.96 | OCH$_2$CH$_2$COOH | |
| 25.97 | OC(CH$_3$)$_2$COOH | |
| 25.98 | OC(CH$_3$)$_2$COOCH$_3$ | |
| 25.99 | OC(CH$_3$)$_2$COOEt | |
| 25.100 | OCH$_2$COOH | |
| 25.101 | OSO$_2$CH$_3$ | |
| 25.102 | OSO$_2$CF$_3$ | |
| 25.103 | CH$_2$CHClCOOC$_2$H$_5$ | |
| 25.104 | CH$_2$CHClCON(C$_2$H$_5$)$_2$ | |
| 25.105 | CH$_2$CHClCONHOH | |
| 25.106 | CH$_2$CHClCOOCH$_2$C$_6$H$_5$ | |
| 25.107 | CH$_2$CH(CH$_3$)COOH | |
| 25.108 | CH$_2$CH(CH$_3$)COOC$_2$H$_5$ | |
| 25.109 | —COOCH$_2$-(cyclopropyl) | |
| 25.110 | COOC(CH$_3$)$_2$COOCH$_2$CH$_2$OC$_2$H$_5$ | |
| 25.111 | —COOC(CH$_3$)$_2$COOCH$_2$-(cyclopropyl) | |
| 25.112 | COOC(CH$_3$)$_2$CONHCH$_2$C≡CH | |
| 25.113 | COOC(CH$_3$)$_2$CON(CH$_2$CH$_3$)$_2$ | |
| 25.114 | OCH$_2$-(cyclopropyl) | |

TABLE 26

Compounds of formula Izz (Izz): 3-(2-chloro-4-cyano-phenyl substituted with R6)-1,4-dimethyl-5-methylsulfinyl-pyrazole

| Comp. No. | R$_6$ | M.p. |
|---|---|---|
| 26.1 | H | |
| 26.2 | CN | |
| 26.3 | OCH$_3$ | |
| 26.4 | NHSO$_2$CH$_3$ | |
| 26.5 | OC$_3$H$_7$(iso) | |
| 26.6 | O-propargyl | |
| 26.7 | OCH(CH$_3$)C≡CH | |
| 26.8 | OCH$_2$COOCH$_2$CH$_3$ | |
| 26.9 | OCH$_2$CH$_2$OCH$_3$ | |
| 26.10 | OCH$_2$CH$_2$SCH$_2$CH$_3$ | |
| 26.11 | OCH$_2$COOCH$_3$ | |
| 26.12 | OCH$_2$COOC$_5$H$_{11}$(n) | |
| 26.13 | OCH$_2$COO-benzyl | |
| 26.14 | OCH(CH$_3$)COObenzyl | |
| 26.15 | SC$_3$H$_7$(iso) | |
| 26.16 | SCH$_2$COOCH$_3$ | |
| 26.17 | SCH$_2$COOC$_2$H$_5$ | |

TABLE 26-continued

Compounds of formula Izz

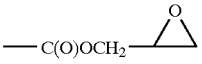

(Izz)

| Comp. No. | R₆ | M.p. |
|---|---|---|
| 26.18 | SCH(CH₃)COObenzyl | |
| 26.19 | SCH₂COObenzyl | |
| 26.20 | COOCH₃ | |
| 26.21 | COOC₃H₇(iso) | |
| 26.22 | COOC(CH₃)₂COOH | |
| 26.23 | COOC(CH₃)₂COO-allyl | |
| 26.24 | COOC(CH₃)₂COOCH₃ | |
| 26.25 | COOC(CH₃)₂COOethyl | |
| 26.26 | COOC(CH₃)₂CONH-allyl | |
| 26.27 | CH₂CHClCOOethyl | |
| 26.28 | CH₂CH=CH₂ | |
| 26.29 | CH₂CH₂CH₃ | |
| 26.30 | CH₂CH₂CF₃ | |
| 26.31 | OCH(CH₃)COOC₂H₅(R) | |
| 26.32 | OCH(CH₃)COOC₂H₅(S) | |
| 26.33 | OCH(CH₃)COOC₂H₅(R,S) | |
| 26.34 | CH₂CHClCOOH | |
| 26.35 | CH₂CHClCOOCH₃ | |
| 26.36 | CH₂CHClCOOC₃H₇(iso) | |
| 26.37 | CH₂CHClCONHallyl | |
| 26.38 | CH₂C(CH₃)ClCOOH | |
| 26.39 | CH₂C(CH₃)ClCOOCH₃ | |
| 26.40 | CH₂C(CH₃)ClCOOEt | |
| 26.41 | CH₂C(CH₃)ClCONHEt | |
| 26.42 | CH₂CH₂COOH | |
| 26.43 | CH₂CH₂COOCH₃ | |
| 26.44 | CH₂CH₂COOEt | |
| 26.45 | CHClCHClCOOH | |
| 26.46 | CHClCHClCOOCH₃ | |
| 26.47 | CHClCHClCOOEt | |
| 26.48 | CH₂CH(OCH₃)COOH | |
| 26.49 | CH₂CH(OCH₃)COOCH₃ | |
| 26.50 | CH₂CH(OCH₃)COOEt | |
| 26.51 | CH₂CH(SCH₃)COOH | |
| 26.52 | CH₂CH(SCH₃)COOCH₃ | |
| 26.53 | CH₂CH(SCH₃)COOEt | |
| 26.54 | CH=CHCOOH | |
| 26.55 | CH=CHCOOCH₃ | |
| 26.56 | CH=CHCOOEt | |
| 26.57 | CH=CClCOOH | |
| 26.58 | CH=CClCOOCH₃ | |
| 26.59 | COOEt | |
| 26.60 | CONH₂ | |
| 26.61 |  —C(O)OCH₂— | |
| 26.62 | CONHSO₂CH₃ | |
| 26.63 | COOCH₂COOH | |
| 26.64 | COOCH₂COOCH₃ | |
| 26.65 | COOCH(CH₃)COOH | |
| 26.66 | COOCH(CH₃)COOCH₃ | |
| 26.67 | COOCH(CH₃)CH₂COOH | |
| 26.68 | COOCH(CH₃)CH₂COOCH₃ | |
| 26.69 | COOC(CH₃)₂CN | |
| 26.70 | COOCH₂CH₂OCH₃ | |
| 26.71 | COOC(CH₃)₂COOCH₂CH₂OCH₃ | |
| 26.72 | 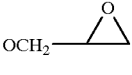 COOC(CH₃)₂—C(O)O—CH₂— | |
| 26.73 | COOC(CH₃)₂COOCH₂PHENYL | |
| 26.74 | COOCH₂C≡CH | |
| 26.75 | COOC(CH₃)₂COOCH₂C≡CH | |
| 26.76 | COOCH(CH₃)C≡CH | |
| 26.77 | COOC(CH₃)₂COCH₃ | |
| 26.78 | NHallyl | |
| 26.79 | N(COCH₃)allyl | |
| 26.80 | N(Et)SO₂CH₃ | |
| 26.81 | N(allyl)SO₂CH₃ | |
| 26.82 | N(allyl)SO₂Et | |
| 26.83 | SO₂N(CH₃)₂ | |
| 26.84 | SO₂NH₂ | |
| 26.85 | SO₂NHCOCH₃ | |
| 26.86 | OH | |
| 26.87 | OEt | |
| 26.88 | Oallyl | |
| 26.89 | OCH₂C≡CCH₃ | |
| 26.90 | OCH(CH₃)CH=CH₂ | |
| 26.91 | OCH₂CH₂OCH₂CH₃ | |
| 26.92 | OCH₂CH₂OCH₂CH₂OCH₃ | |
| 26.93 | 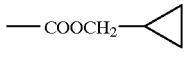 OCH₂— | |
| 26.94 | OCH₂CH₂NHCH₃ | |
| 26.95 | OCH₂CH₂N(CH₃)COCH₃ | |
| 26.96 | OCH₂CH₂COOH | |
| 26.97 | OC(CH₃)₂COOH | |
| 26.98 | OC(CH₃)₂COOCH₃ | |
| 26.99 | OC(CH₃)₂COOEt | |
| 26.100 | OCH₂COOH | |
| 26.101 | OSO₂CH₃ | |
| 26.102 | OSO₂CF₃ | |
| 26.103 | CH₂CHClCOOC₂H₅ | |
| 26.104 | CH₂CHClCON(C₂H₅)₂ | |
| 26.105 | CH₂CHClCONHOH | |
| 26.106 | CH₂CHClCOOCH₂C₆H₅ | |
| 26.107 | CH₂CH(CH₃)COOH | |
| 26.108 | CH₂CH(CH₃)COOC₂H₅ | |
| 26.109 | —COOCH₂— 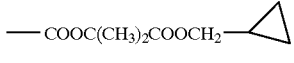 | |
| 26.110 | COOC(CH₃)₂COOCH₂CH₂OC₂H₅ | |
| 26.111 | —COOC(CH₃)₂COOCH₂— 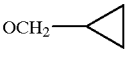 | |
| 26.112 | COOC(CH₃)₂CONHCH₂C≡CH | |
| 26.113 | COOC(CH₃)₂CON(CH₂CH₃)₂ | |
| 26.114 | OCH₂— | |

TABLE 27

Compounds of formula Iyy

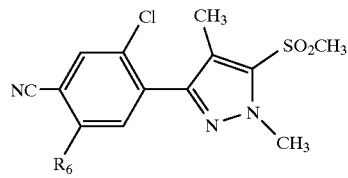

(Iyy)

| Comp. No. | R₆ | M.p. |
|---|---|---|
| 27.1 | H | |
| 27.2 | CN | |
| 27.3 | OCH₃ | |
| 27.4 | NHSO₂CH₃ | |
| 27.5 | OC₃H₇(iso) | |
| 27.6 | O-propargyl | |
| 27.7 | OCH(CH₃)C≡CH | |
| 27.8 | OCH₂COOCH₂CH₃ | |
| 27.9 | OCH₂CH₂OCH₃ | |
| 27.10 | OCH₂CH₂SCH₂CH₃ | |
| 27.11 | OCH₂COOCH₃ | |
| 27.12 | OCH₂COOC₅H₁₁(n) | |
| 27.13 | OCH₂COO-benzyl | |
| 27.14 | OCH(CH₃)COObenzyl | |
| 27.15 | SC₃H₇(iso) | |
| 27.16 | SCH₂COOCH₃ | |
| 27.17 | SCH₂COOC₂H₅ | |
| 27.18 | SCH(CH₃)COObenzyl | |
| 27.19 | SCH₂COObenzyl | |
| 27.20 | COOCH₃ | |
| 27.21 | COOC₃H₇(iso) | |
| 27.22 | COOC(CH₃)₂COOH | |
| 27.23 | COOC(CH₃)₂COO-allyl | |
| 27.24 | COOC(CH₃)₂COOCH₃ | |
| 27.25 | COOC(CH₃)₂COOethyl | |
| 27.26 | COOC(CH₃)₂CONH-allyl | |
| 27.27 | CH₂CHClCOOethyl | |
| 27.28 | CH₂CH=CH₂ | |
| 27.29 | CH₂CH₂CH₃ | |
| 27.30 | CH₂CH₂CF₃ | |
| 27.31 | OCH(CH₃)COOC₂H₅(R) | |
| 27.32 | OCH(CH₃)COOC₂H₅(S) | |
| 27.33 | OCH(CH₃)COOC₂H₅(R,S) | |
| 27.34 | CH₂CHClCOOH | |
| 27.35 | CH₂CHClCOOCH₃ | |
| 27.36 | CH₂CHClCOOC₃H₇(iso) | |
| 27.37 | CH₂CHClCONHallyl | |
| 27.38 | CH₂C(CH₃)ClCOOH | |
| 27.39 | CH₂C(CH₃)ClCOOCH₃ | |
| 27.40 | CH₂C(CH₃)ClCOOEt | |
| 27.41 | CH₂C(CH₃)ClCONHEt | |
| 27.42 | CH₂CH₂COOH | |
| 27.43 | CH₂CH₂COOCH₃ | |
| 27.44 | CH₂CH₂COOEt | |
| 27.45 | CHClCHClCOOH | |
| 27.46 | CHClCHClCOOCH₃ | |
| 27.47 | CHClCHClCOOEt | |
| 27.48 | CH₂CH(OCH₃)COOH | |
| 27.49 | CH₂CH(OCH₃)COOCH₃ | |
| 27.50 | CH₂CH(OCH₃)COOEt | |
| 27.51 | CH₂CH(SCH₃)COOH | |
| 27.52 | CH₂CH(SCH₃)COOCH₃ | |
| 27.53 | CH₂CH(SCH₃)COOEt | |
| 27.54 | CH=CHCOOH | |
| 27.55 | CH=CHCOOCH₃ | |
| 27.56 | CH=CHCOOEt | |
| 27.57 | CH=CClCOOH | |
| 27.58 | CH=CClCOOCH₃ | |
| 27.59 | COOEt | |
| 27.60 | CONH₂ | |
| 27.61 | —C(O)OCH₂— | |
| 27.62 | CONHSO₂CH₃ | |
| 27.63 | COOCH₂COOH | |
| 27.64 | COOCH₂COOCH₃ | |
| 27.65 | COOCH(CH₃)COOH | |
| 27.66 | COOCH(CH₃)COOCH₃ | |
| 27.67 | COOCH(CH₃)CH₂COOH | |
| 27.68 | COOCH(CH₃)CH₂COOCH₃ | |
| 27.69 | COOC(CH₃)₂CN | |
| 27.70 | COOCH₂CH₂OCH₃ | |
| 27.71 | COOC(CH₃)₂COOCH₂CH₂OCH₃ | |
| 27.72 | COOC(CH₃)₂—C(O)O—CH₂—▱ | |
| 27.73 | COOC(CH₃)₂COOCH₂PHENYL | |
| 27.74 | COOCH₂C≡CH | |
| 27.75 | COOC(CH₃)₂COOCH₂C≡CH | |
| 27.76 | COOCH(CH₃)C≡CH | |
| 27.77 | COOC(CH₃)₂COCH₃ | |
| 27.78 | NHallyl | |
| 27.79 | N(COCH₃)allyl | |
| 27.80 | N(Et)SO₂CH₃ | |
| 27.81 | N(allyl)SO₂CH₃ | |
| 27.82 | N(allyl)SO₂Et | |
| 27.83 | SO₂N(CH₃)₂ | |
| 27.84 | SO₂NH₂ | |
| 27.85 | SO₂NHCOCH₃ | |
| 27.86 | OH | |
| 27.87 | OEt | |
| 27.88 | Oallyl | |
| 27.89 | OCH₂C≡CCH₃ | |
| 27.90 | OCH(CH₃)CH=CH₂ | |
| 27.91 | OCH₂CH₂OCH₂CH₃ | |
| 27.92 | OCH₂CH₂OCH₂CH₂OCH₃ | |
| 27.93 | OCH₂—▱ | |
| 27.94 | OCH₂CH₂NHCH₃ | |
| 27.95 | OCH₂CH₂N(CH₃)COCH₃ | |
| 27.96 | OCH₂CH₂COOH | |
| 27.97 | OC(CH₃)₂COOH | |
| 27.98 | OC(CH₃)₂COOCH₃ | |
| 27.99 | OC(CH₃)₂COOEt | |
| 27.100 | OCH₂COOH | |
| 27.101 | OSO₂CH₃ | |
| 27.102 | OSO₂CF₃ | |
| 27.103 | CH₂CHClCOOC₂H₅ | |
| 27.104 | CH₂CHClCON(C₂H₅)₂ | |
| 27.105 | CH₂CHClCONHOH | |
| 27.106 | CH₂CHClCOOCH₂C₆H₅ | |
| 27.107 | CH₂CH(CH₃)COOH | |
| 27.108 | CH₂CH(CH₃)COOC₂H₅ | |
| 27.109 | —COOCH₂—△ | |
| 27.110 | COOC(CH₃)₂COOCH₂CH₂OC₂H₅ | |
| 27.111 | —COOC(CH₃)₂COOCH₂—△ | |

TABLE 27-continued

Compounds of formula Iyy

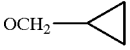

(Iyy)

| Comp. No. | R6 | M.p. |
|---|---|---|
| 27.112 | COOC(CH₃)₂CONHCH₂C≡CH | |
| 27.113 | COOC(CH₃)₂CON(CH₂CH₃)₂ | |
| 27.114 | OCH₂—△ | |

TABLE 28

Compounds of formula lww (lww)

| Comp. No. | R6 | M.p. |
|---|---|---|
| 28.1 | H | |
| 28.2 | CN | |
| 28.3 | OCH₃ | |
| 28.4 | NHSO₂CH₃ | |
| 28.5 | OC₃H₇(iso) | |
| 28.6 | O-propargyl | |
| 28.7 | OCH(CH₃)C≡CH | |
| 28.8 | OCH₂COOCH₂CH₃ | |
| 28.9 | OCH₂CH₂OCH₃ | |
| 28.10 | OCH₂CH₂SCH₂CH₃ | |
| 28.11 | OCH₂COOCH₃ | |
| 28.12 | OCH₂COOC₅H₁₁(n) | |
| 28.13 | OCH₂COO-benzyl | |
| 28.14 | OCH(CH₃)COObenzyl | |
| 28.15 | SC₃H₇(iso) | |
| 28.16 | SCH₂COOCH₃ | |
| 28.17 | SCH₂COOC₂H₅ | |
| 28.18 | SCH(CH₃)COObenzyl | |
| 28.19 | SCH₂COObenzyl | |
| 28.20 | COOCH₃ | |
| 28.21 | COOC₃H₇(iso) | |
| 28.22 | COOC(CH₃)₂COOH | |
| 28.23 | COOC(CH₃)₂COO-allyl | |
| 28.24 | COOC(CH₃)₂COOCH₃ | |
| 28.25 | COOC(CH₃)₂COOethyl | |
| 28.26 | COOC(CH₃)₂CONH-allyl | |
| 28.27 | CH₂CHClCOOethyl | |
| 28.28 | CH₂CH=CH₂ | |
| 28.29 | CH₂CH₂CH₃ | |
| 28.30 | CH₂CH₂CF₃ | |
| 28.31 | OCH(CH₃)COOC₂H₅(R) | |
| 28.32 | OCH(CH₃)COOC₂H₅(S) | |
| 28.33 | OCH(CH₃)COOC₂H₅(R,S) | |
| 28.34 | CH₂CHClCOOH | |
| 28.35 | CH₂CHClCOOCH₃ | |
| 28.36 | CH₂CHClCOOC₃H₇(iso) | |
| 28.37 | CH₂CHClCONHallyl | |
| 28.38 | CH₂C(CH₃)ClCOOH | |
| 28.39 | CH₂C(CH₃)ClCOOCH₃ | |
| 28.40 | CH₂C(CH₃)ClCOOEt | |
| 28.41 | CH₂C(CH₃)ClCONHEt | |
| 28.42 | CH₂CH₂COOH | |
| 28.43 | CH₂CH₂COOCH₃ | |
| 28.44 | CH₂CH₂COOEt | |
| 28.45 | CHClCHClCOOH | |
| 28.46 | CHClCHClCOOCH₃ | |
| 28.47 | CHClCHClCOOEt | |
| 28.48 | CH₂CH(OCH₃)COOH | |
| 28.49 | CH₂CH(OCH₃)COOCH₃ | |
| 28.50 | CH₂CH(OCH₃)COOEt | |
| 28.51 | CH₂CH(SCH₃)COOH | |
| 28.52 | CH₂CH(SCH₃)COOCH₃ | |
| 28.53 | CH₂CH(SCH₃)COOEt | |
| 28.54 | CH=CHCOOH | |
| 28.55 | CH=CHCOOCH₃ | |
| 28.56 | CH=CHCOOEt | |
| 28.57 | CH=CClCOOH | |
| 28.58 | CH=CClCOOCH₃ | |
| 28.59 | COOEt | |
| 28.60 | CONH₂ | |
| 28.61 | —C(O)OCH₂—△O | |
| 28.62 | CONHSO₂CH₃ | |
| 28.63 | COOCH₂COOH | |
| 28.64 | COOCH₂COOCH₃ | |
| 28.65 | COOCH(CH₃)COOH | |
| 28.66 | COOCH(CH₃)COOCH₃ | |
| 28.67 | COOCH(CH₃)CH₂COOH | |
| 28.68 | COOCH(CH₃)CH₂COOCH₃ | |
| 28.69 | COOC(CH₃)₂CN | |
| 28.70 | COOCH₂CH₂OCH₃ | |
| 28.71 | COOC(CH₃)₂COOCH₂CH₂OCH₃ | |
| 28.72 | COOC(CH₃)₂—C(O)O—CH₂—△O | |
| 28.73 | COOC(CH₃)₂COOCH₂PHENYL | |
| 28.74 | COOCH₂C≡CH | |
| 28.75 | COOC(CH₃)₂COOCH₂C≡CH | |
| 28.76 | COOCH(CH₃)C≡CH | |
| 28.77 | COOC(CH₃)₂COCH₃ | |
| 28.78 | NHallyl | |
| 28.79 | N(COCH₃)allyl | |
| 28.80 | N(Et)SO₂CH₃ | |
| 28.81 | N(allyl)SO₂CH₃ | |
| 28.82 | N(allyl)SO₂Et | |
| 28.83 | SO₂N(CH₃)₂ | |
| 28.84 | SO₂NH₂ | |
| 28.85 | SO₂NHCOCH₃ | |
| 28.86 | OH | |
| 28.87 | OEt | |
| 28.88 | Oallyl | |
| 28.89 | OCH₂C≡CCH₃ | |
| 28.90 | OCH(CH₃)CH=CH₂ | |
| 28.91 | OCH₂CH₂OCH₂CH₃ | |
| 28.92 | OCH₂CH₂OCH₂CH₂OCH₃ | |

TABLE 28-continued

Compounds of formula lww (lww)

[Structure: 4-fluoro-substituted benzonitrile with R6 group, connected to pyrazole bearing CH3, SCH3, and N-CH3 groups]

| Comp. No. | R6 | M.p. |
|---|---|---|
| 28.93 | OCH2—(oxirane) | |
| 28.94 | OCH$_2$CH$_2$NHCH$_3$ | |
| 28.95 | OCH$_2$CH$_2$N(CH$_3$)COCH$_3$ | |
| 28.96 | OCH$_2$CH$_2$COOH | |
| 28.97 | OC(CH$_3$)$_2$COOH | |
| 28.98 | OC(CH$_3$)$_2$COOCH$_3$ | |
| 28.99 | OC(CH$_3$)$_2$COOEt | |
| 28.100 | OCH$_2$COOH | |
| 28.101 | OSO$_2$CH$_3$ | |
| 28.102 | OSO$_2$CF$_3$ | |
| 28.103 | CH$_2$CHClCOOC$_2$H$_5$ | |
| 28.104 | CH$_2$CHClCON(C$_2$H$_5$)$_2$ | |
| 28.105 | CH$_2$CHClCONHOH | |
| 28.106 | CH$_2$CHClCOOCH$_2$C$_6$H$_5$ | |
| 28.107 | CH$_2$CH(CH$_3$)COOH | |
| 28.108 | CH$_2$CH(CH$_3$)COOC$_2$H$_5$ | |
| 28.109 | —COOCH$_2$—(cyclopropyl) | |
| 28.110 | COOC(CH$_3$)$_2$COOCH$_2$CH$_2$OC$_2$H$_5$ | |
| 28.111 | —COOC(CH$_3$)$_2$COOCH$_2$—(cyclopropyl) | |
| 28.112 | COOC(CH$_3$)$_2$CONHCH$_2$C≡CH | |
| 28.113 | COOC(CH$_3$)$_2$CON(CH$_2$CH$_3$)$_2$ | |
| 28.114 | OCH$_2$—(cyclopropyl) | |

TABLE 29

Compounds of formula lvv (lvv)

[Structure: 4-fluoro-substituted benzonitrile with R6 group, connected to pyrazole bearing CH3, SOCH3, and N-CH3 groups]

| Comp. No. | R6 | M.p. |
|---|---|---|
| 29.1 | H | |
| 29.2 | CN | |
| 29.3 | OCH$_3$ | |
| 29.4 | NHSO$_2$CH$_3$ | |
| 29.5 | OC$_3$H$_7$(iso) | |
| 29.6 | O-propargyl | |
| 29.7 | OCH(CH$_3$)C≡CH | |
| 29.8 | OCH$_2$COOCH$_2$CH$_3$ | |
| 29.9 | OCH$_2$CH$_2$OCH$_3$ | |
| 29.10 | OCH$_2$CH$_2$SCH$_2$CH$_3$ | |
| 29.11 | OCH$_2$COOCH$_3$ | |
| 29.12 | OCH$_2$COOC$_5$H$_{11}$(n) | |
| 29.13 | OCH$_2$COO-benzyl | |
| 29.14 | OCH(CH$_3$)COObenzyl | |
| 29.15 | SC$_3$H$_7$(iso) | |
| 29.16 | SCH$_2$COOCH$_3$ | |
| 29.17 | SCH$_2$COOC$_2$H$_5$ | |
| 29.18 | SCH(CH$_3$)COObenzyl | |
| 29.19 | SCH$_2$COObenzyl | |
| 29.20 | COOCH$_3$ | |
| 29.21 | COOC$_3$H$_7$(iso) | |
| 29.22 | COOC(CH$_3$)$_2$COOH | |
| 29.23 | COOC(CH$_3$)$_2$COO-allyl | |
| 29.24 | COOC(CH$_3$)$_2$COOCH$_3$ | |
| 29.25 | COOC(CH$_3$)$_2$COOethyl | |
| 29.26 | COOC(CH$_3$)$_2$CONH-allyl | |
| 29.27 | CH$_2$CHClCOOethyl | |
| 29.28 | CH$_2$CH=CH$_2$ | |
| 29.29 | CH$_2$CH$_2$CH$_3$ | |
| 29.30 | CH$_2$CH$_2$CF$_3$ | |
| 29.31 | OCH(CH$_3$)COOC$_2$H$_5$(R) | |
| 29.32 | OCH(CH$_3$)COOC$_2$H$_5$(S) | |
| 29.33 | OCH(CH$_3$)COOC$_2$H$_5$(R,S) | |
| 29.34 | CH$_2$CHClCOOH | |
| 29.35 | CH$_2$CHClCOOCH$_3$ | |
| 29.36 | CH$_2$CHClCOOC$_3$H$_7$(iso) | |
| 29.37 | CH$_2$CHClCONHallyl | |
| 29.38 | CH$_2$C(CH$_3$)ClCOOH | |
| 29.39 | CH$_2$C(CH$_3$)ClCOOCH$_3$ | |
| 29.40 | CH$_2$C(CH$_3$)ClCOOEt | |
| 29.41 | CH$_2$C(CH$_3$)ClCONHEt | |
| 29.42 | CH$_2$CH$_2$COOH | |
| 29.43 | CH$_2$CH$_2$COOCH$_3$ | |
| 29.44 | CH$_2$CH$_2$COOEt | |
| 29.45 | CHClCHClCOOH | |
| 29.46 | CHClCHClCOOCH$_3$ | |
| 29.47 | CHClCHClCOOEt | |
| 29.48 | CH$_2$CH(OCH$_3$)COOH | |
| 29.49 | CH$_2$CH(OCH$_3$)COOCH$_3$ | |
| 29.50 | CH$_2$CH(OCH$_3$)COOEt | |
| 29.51 | CH$_2$CH(SCH$_3$)COOH | |
| 29.52 | CH$_2$CH(SCH$_3$)COOCH$_3$ | |
| 29.53 | CH$_2$CH(SCH$_3$)COOEt | |
| 29.54 | CH=CHCOOH | |
| 29.55 | CH=CHCOOCH$_3$ | |
| 29.56 | CH=CHCOOEt | |
| 29.57 | CH=CClCOOH | |
| 29.58 | CH=CClCOOCH$_3$ | |
| 29.59 | COOEt | |
| 29.60 | CONH$_2$ | |
| 29.61 | —C(O)OCH$_2$—(oxirane) | |
| 29.62 | CONHSO$_2$CH$_3$ | |
| 29.63 | COOCH$_2$COOH | |
| 29.64 | COOCH$_2$COOCH$_3$ | |
| 29.65 | COOCH(CH$_3$)COOH | |
| 29.66 | COOCH(CH$_3$)COOCH$_3$ | |
| 29.67 | COOCH(CH$_3$)CH$_2$COOH | |
| 29.68 | COOCH(CH$_3$)CH$_2$COOCH$_3$ | |
| 29.69 | COOC(CH$_3$)$_2$CN | |
| 29.70 | COOCH$_2$COOCH$_3$ | |
| 29.71 | COOC(CH$_3$)$_2$COOCH$_2$CH$_2$OCH$_3$ | |

TABLE 29-continued

Compounds of formula lvv (lvv)

Structure: 4-fluoro-substituted benzene with NC group, $R_6$, connected to pyrazole ring bearing CH₃, SOCH₃, and N-CH₃ substituents.

| Comp. No. | $R_6$ | M.p. |
|---|---|---|
| 29.72 | COOC(CH₃)₂—C(O)O—CH₂—(oxiranyl) | |
| 29.73 | COOC(CH₃)₂COOCH₂PHENYL | |
| 29.74 | COOCH₂C≡CH | |
| 29.75 | COOC(CH₃)₂COOCH₂C≡CH | |
| 29.76 | COOCH(CH₃)C≡CH | |
| 29.77 | COOC(CH₃)₂COCH₃ | |
| 29.78 | NHallyl | |
| 29.79 | N(COCH₃)allyl | |
| 29.80 | N(Et)SO₂CH₃ | |
| 29.81 | N(allyl)SO₂CH₃ | |
| 29.82 | N(allyl)SO₂Et | |
| 29.83 | SO₂N(CH₃)₂ | |
| 29.84 | SO₂NH₂ | |
| 29.85 | SO₂NHCOCH₃ | |
| 29.86 | OH | |
| 29.87 | OEt | |
| 29.88 | Oallyl | |
| 29.89 | OCH₂C≡CCH₃ | |
| 29.90 | OCH(CH₃)CH=CH₂ | |
| 29.91 | OCH₂CH₂OCH₂CH₃ | |
| 29.92 | OCH₂CH₂OCH₂CH₂OCH₃ | |
| 29.93 | OCH₂—(oxiranyl) | |
| 29.94 | OCH₂CH₂NHCH₃ | |
| 29.95 | OCH₂CH₂N(CH₃)COCH₃ | |
| 29.96 | OCH₂CH₂COOH | |
| 29.97 | OC(CH₃)₂COOH | |
| 29.98 | OC(CH₃)₂COOCH₃ | |
| 29.99 | OC(CH₃)₂COOEt | |
| 29.100 | OCH₂COOH | |
| 29.101 | OSO₂CH₃ | |
| 29.102 | OSO₂CF₃ | |
| 29.103 | CH₂CHClCOOC₂H₅ | |
| 29.104 | CH₂CHClCON(C₂H₅)₂ | |
| 29.105 | CH₂CHClCONHOH | |
| 29.106 | CH₂CHClCOOCH₂C₆H₅ | |
| 29.107 | CH₂CH(CH₃)COOH | |
| 29.108 | CH₂CH(CH₃)COOC₂H₅ | |
| 29.109 | —COOCH₂—(cyclopropyl) | |
| 29.110 | COOC(CH₃)₂COOCH₂CH₂OC₂H₅ | |
| 29.111 | —COOC(CH₃)₂COOCH₂—(cyclopropyl) | |
| 29.112 | COOC(CH₃)₂CONHCH₂C≡CH | |
| 29.113 | COOC(CH₃)₂CON(CH₂CH₃)₂ | |
| 29.114 | OCH₂—(cyclopropyl) | |

TABLE 30

Compounds of formula luu (luu)

Structure: 4-fluoro-substituted benzene with NC group, $R_6$, connected to pyrazole ring bearing CH₃, SO₂CH₃, and N-CH₃ substituents.

| Comp. No. | $R_6$ | M.p. |
|---|---|---|
| 30.1 | H | |
| 30.2 | CN | |
| 30.3 | OCH₃ | |
| 30.4 | NHSO₂CH₃ | |
| 30.5 | OC₃H₇(iso) | |
| 30.6 | O-propargyl | |
| 30.7 | OCH(CH₃)C≡CH | |
| 30.8 | OCH₂COOCH₂CH₃ | |
| 30.9 | OCH₂CH₂OCH₃ | |
| 30.10 | OCH₂CH₂SCH₂CH₃ | |
| 30.11 | OCH₂COOCH₃ | |
| 30.12 | OCH₂COOC₅H₁₁(n) | |
| 30.13 | OCH₂COO-benzyl | |
| 30.14 | OCH(CH₃)COObenzyl | |
| 30.15 | SC₃H₇(iso) | |
| 30.16 | SCH₂COOCH₃ | |
| 30.17 | SCH₂COOC₂H₅ | |
| 30.18 | SCH(CH₃)COObenzyl | |
| 30.19 | SCH₂COObenzyl | |
| 30.20 | COOCH₃ | |
| 30.21 | COOC₃H₇(iso) | |
| 30.22 | COOC(CH₃)₂COOH | |
| 30.23 | COOC(CH₃)₂COO-allyl | |
| 30.24 | COOC(CH₃)₂COOCH₃ | |
| 30.25 | COOC(CH₃)₂COOethyl | |
| 30.26 | COOC(CH₃)₂CONH-allyl | |
| 30.27 | CH₂CHClCOOethyl | |
| 30.28 | CH₂CH=CH₂ | |
| 30.29 | CH₂CH₂CH₃ | |
| 30.30 | CH₂CH₂CF₃ | |
| 30.31 | OCH(CH₃)COOC₂H₅(R) | |
| 30.32 | OCH(CH₃)COOC₂H₅(S) | |
| 30.33 | OCH(CH₃)COOC₂H₅(R,S) | |
| 30.34 | CH₂CHClCOOH | |
| 30.35 | CH₂CHClCOOCH₃ | |
| 30.36 | CH₂CHClCOOC₃H₇(iso) | |
| 30.37 | CH₂CHClCONHallyl | |
| 30.38 | CH₂C(CH₃)ClCOOH | |
| 30.39 | CH₂C(CH₃)ClCOOCH₃ | |
| 30.40 | CH₂C(CH₃)ClCOOEt | |
| 30.41 | CH₂C(CH₃)ClCONHEt | |
| 30.42 | CH₂CH₂COOH | |
| 30.43 | CH₂CH₂COOCH₃ | |
| 30.44 | CH₂CH₂COOEt | |
| 30.45 | CHClCHClCOOH | |
| 30.46 | CHClCHClCOOCH₃ | |
| 30.47 | CHClCHClCOOEt | |
| 30.48 | CH₂CH(OCH₃)COOH | |
| 30.49 | CH₂CH(OCH₃)COOCH₃ | |
| 30.50 | CH₂CH(OCH₃)COOEt | |
| 30.51 | CH₂CH(SCH₃)COOH | |
| 30.52 | CH₂CH(SCH₃)COOCH₃ | |
| 30.53 | CH₂CH(SCH₃)COOEt | |
| 30.54 | CH=CHCOOH | |
| 30.55 | CH=CHCOOCH₃ | |
| 30.56 | CH=CHCOOEt | |
| 30.57 | CH=CClCOOH | |
| 30.58 | CH=CClCOOCH₃ | |
| 30.59 | COOEt | |
| 30.60 | CONH₂ | |
| 30.61 | —C(O)OCH₂—(oxiranyl) | |

TABLE 30-continued

Compounds of formula luu (luu)

| Comp. No. | R₆ | M.p. |
|---|---|---|
| 30.62 | CONHSO$_2$CH$_3$ | |
| 30.63 | COOCH$_2$COOH | |
| 30.64 | COOCH$_2$COOCH$_3$ | |
| 30.65 | COOCH(CH$_3$)COOH | |
| 30.66 | COOCH(CH$_3$)COOCH$_3$ | |
| 30.67 | COOCH(CH$_3$)CH$_2$COOH | |
| 30.68 | COOCH(CH$_3$)CH$_2$COOCH$_3$ | |
| 30.69 | COOC(CH$_3$)$_2$CN | |
| 30.70 | COOCH$_2$CH$_2$OCH$_3$ | |
| 30.71 | COOC(CH$_3$)$_2$COOCH$_2$CH$_2$OCH$_3$ | |
| 30.72 | COOC(CH$_3$)$_2$—C(O)O—CH$_2$— 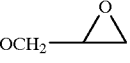 | |
| 30.73 | COOC(CH$_3$)$_2$COOCH$_2$PHENYL | |
| 30.74 | COOCH$_2$C≡CH | |
| 30.75 | COOC(CH$_3$)$_2$COOCH$_2$C≡CH | |
| 30.76 | COOCH(CH$_3$)C≡CH | |
| 30.77 | COOC(CH$_3$)$_2$COCH$_3$ | |
| 30.78 | NHallyl | |
| 30.79 | N(COCH$_3$)allyl | |
| 30.80 | N(Et)SO$_2$CH$_3$ | |
| 30.81 | N(allyl)SO$_2$CH$_3$ | |
| 30.82 | N(allyl)SO$_2$Et | |
| 30.83 | SO$_2$N(CH$_3$)$_2$ | |
| 30.84 | SO$_2$NH$_2$ | |
| 30.85 | SO$_2$NHCOCH$_3$ | |
| 30.86 | OH | |
| 30.87 | OEt | |
| 30.88 | Oallyl | |
| 30.89 | OCH$_2$C≡CCH$_3$ | |
| 30.90 | OCH(CH$_3$)CH=CH$_2$ | |
| 30.91 | OCH$_2$CH$_2$OCH$_2$CH$_3$ | |
| 30.92 | OCH$_2$CH$_2$OCH$_2$CH$_2$OCH$_3$ | |
| 30.93 | OCH$_2$— 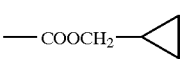 | |
| 30.94 | OCH$_2$CH$_2$NHCH$_3$ | |
| 30.95 | OCH$_2$CH$_2$N(CH$_3$)COCH$_3$ | |
| 30.96 | OCH$_2$CH$_2$COOH | |
| 30.97 | OC(CH$_3$)$_2$COOH | |
| 30.98 | OC(CH$_3$)$_2$COOCH$_3$ | |
| 30.99 | OC(CH$_3$)$_2$COOEt | |
| 30.100 | OCH$_2$COOH | |
| 30.101 | OSO$_2$CH$_3$ | |
| 30.102 | OSO$_2$CF$_3$ | |
| 30.103 | CH$_2$CHClCOOC$_2$H$_5$ | |
| 30.104 | CH$_2$CHClCON(C$_2$H$_5$)$_2$ | |
| 30.105 | CH$_2$CHClCONHOH | |
| 30.106 | CH$_2$CHClCOOCH$_2$C$_6$H$_5$ | |
| 30.107 | CH$_2$CH(CH$_3$)COOH | |
| 30.108 | CH$_2$CH(CH$_3$)COOC$_2$H$_5$ | |
| 30.109 | —COOCH$_2$—  | |
| 30.110 | COOC(CH$_3$)$_2$COOCH$_2$CH$_2$OC$_2$H$_5$ | |
| 30.111 | —COOC(CH$_3$)$_2$COOCH$_2$—  | |
| 30.112 | COOC(CH$_3$)$_2$CONHCH$_2$C≡CH | |
| 30.113 | COOC(CH$_3$)$_2$CON(CH$_2$CH$_3$)$_2$ | |
| 30.114 | OCH$_2$—▷ | |

Formulation Examples for active ingredients of formula I (throughout, percentages are by weight)

| F1. Emulsifiable concentrates | a) | b) | c) | d) |
|---|---|---|---|---|
| a compound of Tables 1–30 | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7–8 mol of ethylene oxide) | — | 4% | — | 2% |
| cylohexanone | — | — | 10% | 20% |
| aromatic hydrocarbon mixture C$_9$–C$_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| a compound of Tables 1–30 | 5% | 10% | 50% | 90% |
| 1-methoxy-3-(3-methoxy-propoxy)-propane | — | 20% | 20% | — |
| polyethylene glycol (mol. wt. 400) | 20% | 10% | — | — |
| N-methyl-2-pyrrolidone | — | — | 30% | 10% |
| aromatic hydrocarbon mixture C$_9$–C$_{12}$ | 75% | 60% | — | — |

The solutions are suitable for application in the form of micro-drops.

| F3. Wettable powders | a) | b) | c) | d) |
|---|---|---|---|---|
| a compound of Tables 1–30 | 5% | 25% | 50% | 80% |
| sodium lignosulfonate | 4% | — | 3% | — |
| sodium laurylsulfate | 2% | 3% | — | 4% |
| sodium diisobutylnaphthalenesulfonate | — | 6% | 5% | 6% |
| octylphenol polyglycol ether (7–8 mol of ethylene oxide) | — | 1% | 2% | — |
| highly dispersed silicic acid | 1% | 3% | 5% | 10% |
| kaolin | 88% | 62% | 35% | — |

The active ingredient is thoroughly mixed with the adjuvants and the mixture is thoroughly ground in a suitable mill, affording wettable powders which can be diluted with water to give suspensions of any desired concentration.

| F4. Coated granules | a) | b) | c) |
|---|---|---|---|
| a compound of Tables 1–30 | 0.1% | 5% | 15% |
| highly dispersed silicic acid | 0.9% | 2% | 2% |
| inorganic carrier (diameter 0.1–1 mm) e.g. CaCO$_3$ or SiO$_2$ | 99.0% | 93% | 83% |

The active ingredient is dissolved in methylene chloride, the solution is sprayed onto the carrier, and the solvent is subsequently evaporated off in vacuo.

| F5. Coated granules | a) | b) | c) |
|---|---|---|---|
| a compound of Tables 1–30 | 0.1% | 5% | 15% |
| polyethylene glycol (mol. wt. 200) | 1.0% | 2% | 3% |
| highly dispersed silicic acid | 0.9% | 1% | 2% |
| inorganic carrier (diameter 0.1–1 mm) e.g. CaCO$_3$ or SiO$_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| a compound of Tables 1–30 | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The mixture is extruded and then dried in a stream of air.

| F7. Dusts | a) | b) | c) |
|---|---|---|---|
| a compound of Tables 1–30 | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| a compound of Tables 1–30 | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension cencentrate from which suspensions of any desired concentration can be obtained by dilution with water.

BIOLOGICAL EXAMPLES

Example B1: Pre-emergence herbicidal action

Monocotyledonous and dicotyledonous test plants are sown in standard soil in plastic pots. Immediately after sowing, an aqueous suspension or emulsion of the test compounds prepared from a 25% wettable powder or emulsifiable concentrate (Example F3, b) or F1, c) is applied by spraying at a rate of application corresponding to 2000 g of active ingredient/hectare (500 l water/ha). The test plants are then cultivated in a greenhouse under optimum conditions. After 3 weeks the test is evaluated in accordance with a scale of nine ratings (1=total damage, 9=no action). Ratings of from 1 to 4 (especially from 1 to 3) indicate good to very good herbicidal action.

Test plants: Avena, Setaria, Sinapis, Stellaria

The compounds according to the invention exhibit good herbicidal action.

Examples of the good herbicidal action are given in Table B1.

TABLE B1

Pre-emergence action:

| | Test plant: | | | |
|---|---|---|---|---|
| Compound No. | Avena | Setaria | Sinapis | Stellaria |
| 1.001 | 1 | 1 | 1 | 1 |
| 1.007 | 1 | 1 | 2 | 1 |
| 1.010 | 2 | 1 | 2 | 1 |
| 2.007 | 2 | 1 | 2 | 1 |
| 2.035 | 2 | 1 | 2 | 1 |
| 2.037 | 2 | 1 | 1 | 1 |
| 3.001 | 1 | 1 | 1 | 1 |
| 3.010 | 3 | 1 | 1 | 1 |
| 3.011 | 2 | 1 | 1 | 1 |
| 3.035 | 2 | 2 | 1 | 1 |
| 7.001 | 5 | 1 | 1 | 3 |
| 8.001 | 5 | 1 | 4 | 3 |
| 8.009 | 3 | 1 | 2 | 2 |
| 9.007 | 3 | 1 | 2 | 1 |

The same results are obtained when compounds of formula I are formulated in accordance with Examples F2 and F4 to F8.

Example B2: Post-emergence herbicidal action (contact herbicide)

In a greenhouse, monocotyledonous and dicotyledonous test plants are raised in plastic pots, containing standard soil and at the 4- to 6-leaf stage are sprayed with an aqueous suspension or emulsion of the test compounds of formula I prepared from a 25% wettable powder or emulsifiable concentrate (Example F3, b) or F1, c)) at a rate of application corresponding to 2000 g of active ingredient/ha (500 l water/ha). The test plants are then grown on in the greenhouse under optimum conditions. After about 18 days the test is evaluated in accordance with a scale of nine ratings (1=total damage, 9=no action). Ratings of from 1 to 4 (especially from 1 to 3) indicate good to very good herbicidal action.

In this test too, the compounds of formula I according to the invention exhibit good herbicidal action.

Examples of the good herbicidal activity of the compounds of formula I are given in Table B2.

TABLE B2

Post-emergence action:

| Compound No. | Avena | Setaria | Sinapis | Stellaria |
|---|---|---|---|---|
| 1.001 | 1 | 1 | 1 | 1 |
| 1.007 | 1 | 1 | 1 | 1 |
| 1.010 | 2 | 1 | 1 | 1 |
| 1.042 | 1 | 1 | 1 | 1 |
| 1.044 | 5 | 2 | 1 | 1 |
| 2.001 | 1 | 1 | 1 | 1 |
| 2.007 | 2 | 1 | 1 | 1 |
| 2.037 | 1 | 1 | 1 | 1 |
| 2.038 | 1 | 1 | 1 | 1 |
| 2.039 | 1 | 1 | 1 | 1 |
| 2.041 | 5 | 2 | 1 | 1 |
| 3.001 | 1 | 1 | 1 | 1 |
| 3.010 | 2 | 1 | 1 | 1 |
| 3.011 | 1 | 1 | 1 | 1 |
| 3.035 | 1 | 1 | 1 | 1 |
| 3.037 | 1 | 1 | 1 | 1 |
| 3.039 | 1 | 1 | 1 | 1 |
| 3.041 | 6 | 2 | 1 | 1 |
| 7.001 | 6 | 2 | 2 | 2 |
| 7.034 | 2 | 1 | 1 | 1 |
| 7.040 | 6 | 2 | 1 | 1 |
| 8.001 | 5 | 1 | 1 | 1 |
| 8.009 | 2 | 1 | 1 | 1 |
| 8.035 | 1 | 1 | 1 | 1 |
| 8.073 | 1 | 1 | 1 | 1 |
| 9.007 | 2 | 1 | 1 | 3 |
| 9.041 | 6 | 3 | 1 | 1 |
| 9.073 | 2 | 2 | 1 | 1 |

The same results are obtained when compounds of formula I are formulated in accordance with Examples F2 and F4 to F8.

What is claimed is:

1. A compound of formula I

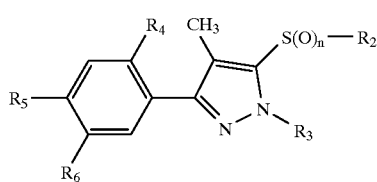

(I)

wherein $R_2$ is $C_1-C_2$alkyl;

n is 0, 1 or 2;

$R_3$ is $C_1-C_4$alkyl;

$R_4$ is hydrogen, fluorine, or chlorine;

$R_5$ is halogen, methyl or cyano;

$R_6$ is (i) hydrogen, (ii) $OR_{20}$ in which $R_{20}$ is hydrogen, $C_1-C_8$alkyl, $C_3-C_8$alkenyl, $C_3-C_8$alkynly, $C_1-C_8$haloalkyl, $C_3-C_6$cycloalkyl, $C_1-C_4$alkoxy-$C_1-C_4$alkyl, $C_1-C_4$alkylthio-$C_1-C_4$alkyl, $C_1-C_8$alkyl-COXR$_{21}$, phenyl, benzyl, those aromatic rings being unsubstituted or mono- to tri-substituted by $C_1-C_4$alkyl, $C_1-C_4$haloalkyl or by halogen, in which;

X is oxygen, sulfur or NR$_{22}$;

$R_{21}$ is hydrogen, $C_1-C_8$alkyl, $C_3-C_8$alkenyl, $C_3-C_8$alkynyl, $C_1-C_8$haloalkyl, $C_3-C_6$cycloalkyl, $C_1-C_4$alkoxy-$C_1-C_4$alkyl, $C_1-C_4$alkylthio-$C_1-C_4$alkyl, phenyl, phenyl mono- to tri-substituted by $C_1-C_4$alkyl, $C_1-C_4$haloalkyl or by halogen, benzyl, or benzyl mono- to tri-substituted by $C_1-C_4$alkyl or by halogen; and $R_{22}$ is hydrogen, $C_1-C_8$alkyl or $C_3-C_8$alkenyl;

(iii) COYR$_{50}$ in which

Y is oxygen, sulfur, NR$_{51}$ or NOR$_{54}$, and $R_{50}$ is hydrogen, $C_1-C_8$alkyl, $C_3-C_8$alkenyl, $C_3-C_8$alkynyl, $C_1-C_8$haloalkyl, $C_3-C_6$cycloalkyl, $C_1-C_4$alkoxy-$C_1-C_4$alkyl, $C_1-C_4$alkylthio-$C_1-C_4$alkyl, phenyl, phenyl mono- to tri-substituted by $C_1-C_4$alkyl, $C_1-C_4$haloalkyl or by halogen, benzyl, benzyl mono-to tri-substituted by $C_1-C_4$alkyl, $C_1-C_4$haloalkyl or by halogen, $C_1-C_4$alkyl-COZR$_{52}$, in which Z is oxygen, sulfur, NR$_{53}$ or NOR$_{56}$;

$R_{52}$ is hydrogen, $C_1-C_8$alkyl, $C_3-C_8$alkenyl, $C_3-C_8$alkynyl, $C_1-C_8$haloalkyl, $C_3-C_6$cycloalkyl, $C_1-C_4$alkoxy-$C_1-C_4$alkyl, $C_1-C_4$alkylthio-$C_1-C_4$alkyl, phenyl, phenyl mono- to tri-substituted by $C_1-C_4$alkyl, $C_1-C_4$haloalkyl or by halogen;

$R_{51}$ and $R_{53}$ are each independently of the other $C_1-C_8$alkyl, $C_3-C_8$alkenyl, $C_3-C_8$alkynyl, $C_1-C_8$haloalkyl, $C_1-C_4$alkylcarbonyl, $C_1-C_4$haloalkylcarbonyl, $C_1-C_4$alkylsulfonyl, $C_1-C_4$haloalkylsulfonyl, benzoyl, benzoyl mono-to tri-substituted by $C_1-C_4$alkyl, $C_1-C_4$haloalkyl or by halogen, benzyl, or benzyl mono- to tri-substituted by $C_1-C_4$alkyl, $C_1-C_4$haloalkyl or by halogen; and $R_{54}$ and $R_{55}$ are each independently of the other $C_1-C_4$alkyl; or (iv) $C_1-C_4$alkyl-COZR$_{52}$, $C_1-C_4$haloalkyl-COZR$_{52}$, $C_2-C_4$alkenyl-COZR$_{52}$, $C_3-C_8$alkynyl-COZR$_{52}$, or the salts or stereoisomers thereof.

2. A compound according to claim 1, wherein $R_5$ is chlorine, bromine, methyl or cyano.

3. A compound according to claim 1, wherein n is 0 or 2.

4. A compound according to claim 1, wherein $R_2$ is methyl.

5. A compound according to claim 1, wherein $R_3$ is methyl or ethyl.

6. A compound according to claim 1, wherein $R_3$ is methyl.

7. A compound according to claim 1, wherein $R_4$ is fluorine.

8. A compound according to claim 1, wherein $R_4$ is hydrogen.

9. A compound according to claim 1, wherein $R_4$ is chlorine.

10. A compound according to claim 1, wherein $R_4$ is chlorine; and $R_6$ is OR$_{20}$.

11. A compound according to claim 1, wherein $R_4$ is fluorine; and $R_6$ is OR$_{20}$.

12. A compound according to claim 1, wherein $R_4$ is chlorine; and $R_6$ is COYR$_{50}$, $C_1-C_4$alkylCOZR$_{52}$, $C_1-C_4$haloalkylCOZR$_{52}$, $C_2-C_4$alkenylCOZR$_{52}$, $C_3-C_8$alkynylCOZR$_{52}$ or $C_2-C_4$haloalkenylCOZR$_{52}$.

13. A compound according to claim 1, wherein $R_4$ is fluorine; and $R_6$ is COYR$_5$, $C_1-C_4$alkylCOZR$_{52}$, $C_1-C_4$haloalkylCOZR$_{52}$, $C_2-C_4$alkenylCOZR$_{52}$, $C_3-C_8$alkynylCOZR$_{52}$ or $C_2-C_4$haloalkenylCOZR$_{52}$.

14. A compound according to claim 1, wherein $R_5$ is chlorine; and $R_6$ is —COYR$_{50}$.

15. A herbicidal and plant growth-inhibiting composition comprising one or more compounds of formula I according to claim 1.

16. A composition according to claim 15, comprising from 0.1 to 95% of a compound of formula I.

17. A method of controlling undesired plant growth, which comprises applying an effective amount of a compound of formula I, according to claim 1, or of a composition comprising such a compound, to the plants or to the locus thereof.

18. A method according to claim 17, which comprises the application of a compound of formula I in an amount of from 0.001 to 2 kg per hectare.

19. A method of inhibiting plant growth, which comprises applying an effective amount of a compound of formula I, according to claim 1, or of a composition comprising such a compound, to the plants or to the locus thereof.

* * * * *